US010980836B1

(12) United States Patent
Getts et al.

(10) Patent No.: US 10,980,836 B1
(45) Date of Patent: Apr. 20, 2021

(54) THERAPEUTIC CELL COMPOSITIONS AND METHODS OF MANUFACTURING AND USE THEREOF

(71) Applicant: Myeloid Therapeutics, Inc., Boston, MA (US)

(72) Inventors: Daniel Getts, Westminster, MA (US); Yuxiao Wang, San Francisco, CA (US)

(73) Assignee: Myeloid Therapeutics, Inc., Boston, MA (US)

( * ) Notice: Subject to any disclaimer, the term of this patent is extended or adjusted under 35 U.S.C. 154(b) by 0 days.

(21) Appl. No.: 16/826,708

(22) Filed: Mar. 23, 2020

Related U.S. Application Data

(60) Provisional application No. 62/946,896, filed on Dec. 11, 2019.

(51) Int. Cl.

| | |
|---|---|
| ***A61K 35/15*** | (2015.01) |
| ***C07K 16/28*** | (2006.01) |
| ***C12N 9/12*** | (2006.01) |
| ***C07K 14/705*** | (2006.01) |
| ***C12N 15/87*** | (2006.01) |
| ***A61P 35/00*** | (2006.01) |
| ***C12N 5/0786*** | (2010.01) |

(52) U.S. Cl.
CPC .............. *A61K 35/15* (2013.01); *A61P 35/00* (2018.01); *C07K 14/70578* (2013.01); *C07K 16/2863* (2013.01); *C07K 16/2896* (2013.01); *C12N 5/0645* (2013.01); *C12N 9/1205* (2013.01); *C12N 15/87* (2013.01); *C07K 2317/52* (2013.01); *C07K 2317/622* (2013.01); *C07K 2319/03* (2013.01)

(58) Field of Classification Search
CPC .............................. A61K 35/15; C12N 5/0645
See application file for complete search history.

(56) References Cited

U.S. PATENT DOCUMENTS

| | | | | |
|---|---|---|---|---|
| 6,210,963 | B1 | 4/2001 | Haddada et al. | |
| 8,198,020 | B2 | 6/2012 | Francois et al. | |
| 8,709,412 | B2 | 4/2014 | Jones et al. | |
| 9,045,541 | B2 | 6/2015 | Eckelman et al. | |
| 9,149,519 | B2 | 10/2015 | Landau et al. | |
| 9,221,908 | B2 | 12/2015 | Frazier et al. | |
| 9,518,116 | B2 | 12/2016 | Frazier et al. | |
| 9,663,575 | B2 | 5/2017 | Eckelman et al. | |
| 9,745,368 | B2 | 8/2017 | Milone et al. | |
| 9,845,345 | B2 | 12/2017 | Ring et al. | |
| 10,034,900 | B2 | 7/2018 | Senju | |
| 10,081,680 | B2 | 9/2018 | Weiskopf et al. | |
| 10,106,609 | B2 | 10/2018 | Yang et al. | |
| 10,259,859 | B2 | 4/2019 | Pons et al. | |
| 10,259,873 | B2 | 4/2019 | Frazier et al. | |
| 10,415,017 | B2 | 9/2019 | O'Neill | |
| 10,428,143 | B2 | 10/2019 | Krummel et al. | |
| 2004/0053873 | A1 | 3/2004 | Barman et al. | |
| 2006/0018889 | A1 | 1/2006 | Li et al. | |
| 2008/0254027 | A1 | 10/2008 | Bernett et al. | |
| 2011/0250203 | A1 | 10/2011 | Klitgaard et al. | |
| 2014/0134142 | A1 | 5/2014 | Smith et al. | |
| 2014/0140989 | A1 | 5/2014 | Eckelman et al. | |
| 2014/0161805 | A1 | 6/2014 | Jamieson et al. | |
| 2014/0242701 | A1 | 8/2014 | Shiku et al. | |
| 2015/0057161 | A1 | 2/2015 | Schultze et al. | |
| 2015/0274826 | A1 | 10/2015 | Frazier et al. | |
| 2016/0137733 | A1 | 5/2016 | Frazier et al. | |
| 2016/0250258 | A1 | 9/2016 | Delaney et al. | |
| 2016/0251435 | A1 | 9/2016 | Eckelman et al. | |
| 2017/0087185 | A1 | 3/2017 | Crane et al. | |
| 2017/0151281 | A1* | 6/2017 | Wagner | A61K 38/177 |
| 2017/0151282 | A1 | 6/2017 | Discher et al. | |
| 2017/0166657 | A1 | 6/2017 | O'Neill et al. | |
| 2017/0226183 | A1 | 8/2017 | Schiffer-Mannioui | |
| 2017/0233452 | A1 | 8/2017 | McIvor et al. | |
| 2017/0246278 | A1 | 8/2017 | Vera Valdes et al. | |
| 2017/0283498 | A1 | 10/2017 | Frazier et al. | |
| 2017/0292118 | A1 | 10/2017 | Duchateau et al. | |
| 2018/0000899 | A1 | 1/2018 | Francois et al. | |
| 2018/0030553 | A1* | 2/2018 | Tang | A61K 35/15 |
| 2018/0057592 | A1 | 3/2018 | Frazier et al. | |
| 2018/0104308 | A1 | 4/2018 | Mamonkin et al. | |
| 2018/0105600 | A1 | 4/2018 | Pons et al. | |
| 2018/0133252 | A9 | 5/2018 | Wilson et al. | |
| 2018/0142019 | A1 | 5/2018 | Manning et al. | |
| 2018/0155405 | A1 | 6/2018 | Ring et al. | |

(Continued)

FOREIGN PATENT DOCUMENTS

| | | |
|---|---|---|
| CA | 2850380 C | 8/2015 |
| EP | 2626415 A2 | 8/2013 |

(Continued)

OTHER PUBLICATIONS

Auffray et al. (Annual Rev. Immunol. 2009 27:669-92) (Year: 2009).*
Ancuta et al. (BMC Genomics 2009 10:403, pp. 1-19) (Year: 2009).*
Laird et al. (J. Leukocyte Biology 2009, 85: 966-977) (Year: 2009).*
Tippet et al. (J. Leukocyte Biology 2013 93: 913-920) (Year: 2009).*
Soderberg et al. (J. Virology 1993 67(6): 3166-3175) (Year: 1993).*
Wilkinson et al. (Med. Microbiol. Immunol. 2015 204:273-284) (Year: 2015).*

(Continued)

*Primary Examiner* — Peter J Reddig
(74) *Attorney, Agent, or Firm* — Wilson Sonsini Goodrich & Rosati

(57) ABSTRACT

The present disclosure provides compositions and methods for making and using engineered killer phagocytic cells for immunotherapy in cancer or infection by expressing a chimeric antigen receptor having an enhanced phagocytic activity, the chimeric receptor is encoded by a recombinant nucleic acid.

21 Claims, 37 Drawing Sheets

Specification includes a Sequence Listing.

(56) References Cited

U.S. PATENT DOCUMENTS

| | | | |
|---|---|---|---|
| 2018/0171021 | A1 | 6/2018 | Karlsson et al. |
| 2018/0186878 | A1 | 7/2018 | Rosenthal |
| 2018/0221503 | A1 | 8/2018 | Kadiyala et al. |
| 2018/0244748 | A1 | 8/2018 | Gill et al. |
| 2018/0250395 | A1 | 9/2018 | Pietsch et al. |
| 2018/0319883 | A1 | 11/2018 | Weiskopf et al. |
| 2018/0325953 | A1 | 11/2018 | Poznansky et al. |
| 2019/0023761 | A1 | 1/2019 | Pule et al. |
| 2019/0038671 | A1 | 2/2019 | Fan et al. |
| 2019/0062450 | A1 | 2/2019 | De Palma |
| 2019/0070277 | A1 | 3/2019 | O'Neill et al. |
| 2019/0112373 | A1 | 4/2019 | Manning et al. |
| 2019/0119379 | A1 | 4/2019 | Gottschalk et al. |
| 2019/0119396 | A1 | 4/2019 | Liu et al. |
| 2019/0144522 | A1 | 5/2019 | Bari et al. |
| 2019/0169266 | A1 | 6/2019 | Pons et al. |
| 2019/0233496 | A1 | 8/2019 | Rosenthal |
| 2019/0240343 | A1 | 8/2019 | Ahmed et al. |
| 2019/0248892 | A1 | 8/2019 | Frazier et al. |
| 2019/0263928 | A1 | 8/2019 | Watanabe et al. |
| 2019/0275150 | A1 | 9/2019 | Pincetic et al. |
| 2019/0336615 | A1 | 11/2019 | Thompson et al. |
| 2019/0345217 | A1 | 11/2019 | Ma et al. |

FOREIGN PATENT DOCUMENTS

| | | | |
|---|---|---|---|
| EP | 2242512 | B1 | 4/2016 |
| EP | 2956343 | B1 | 12/2018 |
| EP | 3504244 | A1 | 7/2019 |
| EP | 3519441 | A1 | 8/2019 |
| GB | 2572005 | A | 9/2019 |
| WO | WO-1995005835 | A1 | 3/1995 |
| WO | WO-2004050855 | A2 | 6/2004 |
| WO | WO-2008011599 | A2 | 1/2008 |
| WO | WO-2017044487 | A1 | 3/2017 |
| WO | WO-2017136633 | A1 | 8/2017 |
| WO | WO-2018169948 | A1 | 9/2018 |
| WO | WO-2019005641 | A1 | 1/2019 |
| WO | WO-2019032624 | A1 | 2/2019 |
| WO | WO-2019067328 | A1 | 4/2019 |
| WO | WO-2019070704 | A1 | 4/2019 |
| WO | WO-2019086512 | A1 | 5/2019 |
| WO | WO-2019129146 | A1 | 7/2019 |
| WO | WO-2019191332 | A1 | 10/2019 |
| WO | WO-2019191334 | A1 | 10/2019 |
| WO | WO-2019191340 | A1 | 10/2019 |
| WO | WO-2020097193 | A1 | 5/2020 |

OTHER PUBLICATIONS

Ali, M. et al., "Induction of neoantigen-reactive T cells from healthy donors", Nature Protocols (2019).

Alvey C, Discher DE. 2017. Engineering macrophages to eat Cancer: from "marker of self" CD47 and phagocytosis to differentiation. Journal of Leukocyte Biology 102:31-40.

Alvey CM, Spinier KR, Irianto J, Pfeifer CR, Hayes B, Xia Y, Cho S, Dingal P, Hsu J, Smith L, Tewari M, Discher DE. 2017. SIRPA-Inhibited, Marrow-Derived macrophages engorge, accumulate, and differentiate in Antibody-Targeted regression of solid tumors. Current Biology 27:2065-2077.

Andreesen R, Scheibenbogen C, Brugger W, Krause S, Meerpohl HG, Leser HG, Engler H, Lo hr GW. 1990. Adoptive transfer of tumor cytotoxic macrophages generated in vitro from circulating blood monocytes: a new approach to Cancer immunotherapy. Cancer Research 50:7450-7456.

Andreu N, Phelan J, de Sessions PF, Cliff JM, Clark TG, Hibberd ML. 2017. Primary macrophages and J774 cells respond differently to infection with Mycobacterium tuberculosis. Scientific Reports 7:42225.

Batista FD, Iber D, Neuberger MS. 2001. B cells acquire antigen from target cells after synapse formation. Nature 411:489-494.

Beningo KA, Wang YL. 2002. Fc-receptor-mediated phagocytosis is regulated by mechanical properties of the target. Journal of Cell Science 115:849-856.

Berger, et al., "Efficient Elutriation of monocytes within a closed system (Elutra™) Journal of Immunological Methods 298 (2005) 61-72".

Bhattacharjee, J., et al., "Monocytes isolated by positive and negative magnetic sorting techniques show different molecular characteristics and immunophenotypic behaviour", F100Research (2018) pp. 1-13.

Biglari, A., et al. Human monocytes expressing a CEA-specific chimeric CD64 receptor specifically target CEA-expressing tumour cells in vitro and in vivo, Gene Therapy (2006) 13, 602-610.

Brooks SR, Kirkham PM, Freeberg L, Carter RH. 2004. Binding of cytoplasmic proteins to the CD19 intracellular domain is high affinity, competitive, and multimeric. The Journal of Immunology 172:7556-7564.

Bu JY, Shaw AS, Chan AC. 1995. Analysis of the interaction of ZAP-70 and syk protein-tyrosine kinases with the T-cell antigen receptor by plasmon resonance. PNAS 92:5106-5110.

Chao MP, Alizadeh AA, Tang C, Myklebust JH, Varghese B, Gill S, Jan M, Cha AC, Chan CK, Tan BT, Park CY,Zhao F, Kohrt HE, Malumbres R, Briones J, Gascoyne RD, Lossos IS, Levy R, Weissman IL, Majeti R. 2010. Anti-CD47 antibody synergizes with rituximab to promote phagocytosis and eradicate non-Hodgkin lymphoma. Cell 142:699-713.

Chen J, Zhong MC, Guo H, Davidson D, Mishel S, Lu Y, Rhee I, Pe' rez-Quintero LA, Zhang S, Cruz-Munoz ME, Wu N, Vinh DC, Sinha M, Calderon V, Lowell CA, Danska JS, Veillette A. 2017. SLAMF7 is critical for phagocytosis of haematopoietic tumour cells via Mac-1 integrin. Nature 544:493-497.

Corresponding PCT Application No. PCT/US2019/060052, filed Nov. 6, 2019.

"Cross, et al., "Human CD14dim) Monocytes Patrol and Sense Nucleic Acids and ciruses via TLR7 and TLR8 Receptors", Immunity 33, 375-386, Sep. 24, 2010".

Cross SE, Jin YS, Rao J, Gimzewski JK. 2007. Nanomechanical analysis of cells from cancer patients. Nature Nanotechnology 2:780-783.

Davis SJ, van der Merwe PA. 2006. The kinetic-segregation model: TCR triggering and beyond. Nature Immunology 7:803-809.

De Oliveria, S, et al., "Modification of Hematopoietic Stem/ Progenitor Cells with CD19-Specific Chimeric Antigen Receptros as a Novel Approach for Cancer Immunotherapy" Human Gene Therapy 24:824-839 (Oct. 2013).

Edelstein A, Amodaj N, Hoover K, Vale R, Stuurman N. 2010. Computer control of microscopes using mmanager. Current Protocols in Molecular Biology 14:Unit14.20.

Engel P, Zhou LJ, Ord DC, Sato S, Koller B, Tedder TF. 1995. Abnormal B lymphocyte development, activation, and differentiation in mice that lack or overexpress the CD19 signal transduction molecule. Immunity 3:39-50.

"Senju, Satoru, et al., "Generation and genetic modification of dendritic cells derived from mouse embryonic stem cells derived from mouse embryonics stem cells", BLOOD, May 1, 2003, vol. 101, No. 9, pp. 3501-3508".

Fesnak AD, June CH, Levine BL. 2016. Engineered T cells: the promise and challenges of cancer immunotherapy. Nature Reviews Cancer 16:566-581.

Fraser, A., et al, "Development, functional characterization and validation of methodology for GMP-compliant manufacture of phagocytic macrophages: A novel cellular therapeutic for liver cirrhosis", Cyotherapy, 2017, ISSN 1465-3249.

Freeman SA, Goyette J, Furuya W, Woods EC, Bertozzi CR, Bergmeier W, Hinz B, van der Merwe PA, Das R, Grinstein S. 2016. Integrins Form an Expanding Diffusional Barrier that Coordinates Phagocytosis. Cell 164: 128-140.

Freeman SA, Grinstein S. 2014. Phagocytosis: receptors, signal integration, and the cytoskeleton. Immunological Reviews 262:193-215.

Gardai SJ, McPhillips KA, Frasch SC, Janssen WJ, Starefeldt A, Murphy-Ullrich JE, Bratton DL, Oldenborg PA, Michalak M,

(56) References Cited

OTHER PUBLICATIONS

Henson PM. 2005. Cell-surface calreticulin initiates clearance of viable or apoptotic cells through trans-activation of LRP on the phagocyte. Cell 123:321-334.

"Geissmann, et al., "Blood Monocytes Consist of Two Principal Subsets with Distinct Migratory Properties", Immunity, vol. 19, pp. 71-82, Jul. 2003".

"Getts, Daniel R., "Microparticles bearing encephalitogenic peptides induce T-cell tolerance and ameliorate experimental autoimmune encephalomyelitis", Nat Biotechnol. Dec. 2012; 30(12): 1217-1224".

Goudot, C. et al., "Aryl Hydrocarbon Receptro Controls Monocyte Differentiation into Dendritic Cells versus Macrophages", Sep. 19, 2017 Immunity 47, 582-596.

Harshyne LA, Zimmer MI, Watkins SC, Barratt-Boyes SM. 2003. A Role for Class A Scavenger Receptor in Dendritic Cell Nibbling from Live Cells. The Journal of Immunology 170:2302-2309.

Harshyne LA, Watkins SC, Gambotto A, Barratt-Boyes SM. 2001. Dendritic cells acquire antigens from live cells for Cross-Presentation to CTL. The Journal of Immunology 166:3717-3723.

Haso W, Lee DW, Shah NN, Stetler-Stevenson M, Yuan CM, Pastan IH, Dimitrov DS, Morgan RA, FitzGerald DJ, Barrett DM, Wayne AS, Mackall CL, Orentas RJ. 2013. Anti-CD22-chimeric antigen receptors targeting B-cell precursor acute lymphoblastic leukemia. Blood 121:1165-1174.

Huang, Min-Nung, et al., "Antigen-loaded monocyte administration induces potent therapeutic antitumor T cell responses", J. Clin Invest, 2020, 130(2): 774-778.

Hui E, Vale RD. 2014. In vitro membrane reconstitution of the T-cell receptor proximal signaling network. Nature Structural & Molecular Biology 21:133-142.

"Ingersoll, Ph.D., Brooke, "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160".

Jadus MR, Irwin MC, Irwin MR, Horansky RD, Sekhon S, Pepper KA, Kohn DB, Wepsic HT. 1996. Macrophages can recognize and kill tumor cells bearing the membrane isoform of macrophage colony-stimulating factor. Blood 87:5232-5241.

Jaiswal S, Jamieson CH, Pang WW, Park CY, Chao MP, Majeti R, Traver D, van Rooijen N, Weissman IL. 2009. CD47 is upregulated on circulating hematopoietic stem cells and leukemia cells to avoid phagocytosis. Cell 138:271-285.

James JR, Vale RD. 2012. Biophysical mechanism of T-cell receptor triggering in a reconstituted system. Nature 487:64-69.

Joly E, Hudrisier D. 2003. What is trogocytosis and what is its purpose? Nature Immunology 4:815.

Kao G, Huang CC, Hedgecock EM, Hall DH, Wadsworth WG. 2006. The role of the laminin beta subunit in laminin heterotrimer assembly and basement membrane function and development in C. elegans. Developmental Biology 290:211-219.

"Kim, et al., "Monocyte Enrichment from Leukapheresis productws by using the Elutra cell separator" Transfusion, vol. 47, Dec. 2007 pp. 2290-2296".

Kochenderfer JN, Feldman SA, Zhao Y, Xu H, Black MA, Morgan RA, Wilson WH, Rosenberg SA. 2009. Construction and preclinical evaluation of an anti-CD19 chimeric antigen receptor. Journal of Immunotherapy 32:689-702.

Lacerna LV, Stevenson GW, Stevenson HC. 1988. Adoptive cancer immunotherapy utilizing lymphokine activated killer cells and gamma interferon activated killer monocytes. Pharmacology & Therapeutics 38:453-465.

Lee S, Kivimae S, Dolor A, Szoka FC. 2016. Macrophage-based cell therapies: the long and winding road. Journal of Controlled Release 240:527-540.

Lim WA, June CH, Huang J, Hodes RJ. 2017. The Principles of Engineering Immune Cells to Treat Cancer. Cell 168:724-740.

Liu X, Pu Y, Cron K, Deng L, Kline J, Frazier WA, Xu H, Peng H, Fu YX, Xu MM. 2015. CD47 blockade triggers T cell-mediated destruction of immunogenic tumors. Nature Medicine 21:1209-1215.

Majeti R, Chao MP, Alizadeh AA, Pang WW, Jaiswal S, Gibbs KD, van Rooijen N, Weissman IL. 2009. CD47 is an adverse prognostic factor and therapeutic antibody target on human acute myeloid leukemia stem cells. Cell 138:286-299.

"Matsuyoshi, Hidetake, et al., "Enchanced Priming of Antigen-Specific CTL's In Vivo by Embryonic Stem Cell-Derived Dendritic Cells Expressing Chemokine Along with Antigenic Protein: Application to Antitumor Vaccination", The Journal of Immunology (2004) 172:776-786".

Mayordomo JI, Zorina T, Storkus WJ, Zitvogel L, Celluzzi C, Falo LD, Melief CJ, Ildstad ST, Kast WM, Deleo AB. 1995. Bone marrow-derived dendritic cells pulsed with synthetic tumour peptides elicit protective and therapeutic antitumour immunity. Nature Medicine 1:1297-1302.

"Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171".

Morrissey, M., et al., "Chimeric antigen receptors that trigger phagocytosis", eLife 2018, pp. 1/21.

Mukherjee, R. et al., "Non-Classical monocytes display inflammatory features: Validation in Sepsis and Systemic Lupus Erythematous", Scientific Reports, (2015) pp. 1-14.

"Murshid, Ayesha, et al, "Hsp90-peptide complexes stimulate antigen presentation through the class II pathway after binding scavenger receptor SREC-1", Immunobiology, Dec. 2014; 219(12); 924-931".

"Paslick, et al., "Identification and Characterization of a Novel Monocyte Subpopulation in Human Peripheral Blood", Article in Blood, Dec. 1989, 74: 2527-2534".

Penberthy KK, Ravichandran KS. 2016. Apoptotic cell recognition receptors and scavenger receptors. Immunological Reviews 269:44-59.

Ralston KS, Solga MD, Mackey-Lawrence NM, Somlata , Bhattacharya A, Petri WA. 2014. Trogocytosis by Entamoeba histolytica contributes to cell killing and tissue invasion. Nature 508:526-530.

Roberts EW, Broz ML, Binnewies M, Headley MB, Nelson AE, Wolf DM, Kaisho T, Bogunovic D, Bhardwaj N, Krummel MF. 2016. Critical Role for CD103(+)/CD141(+) Dendritic Cells Bearing CCR7 for Tumor Antigen Trafficking and Priming of T Cell Immunity in Melanoma. Cancer Cell 30:324-336.

Roberts, Margo R., et al."Antigen-Specific Cytolysis by Neutrophils and NK Cells Expressing Chimeric Immune Receptros Bearing xx Signaling Domains", J Immunol 1998; 161:375-384.

Rosales, C. et al, "Phagocytosis: A Fundamental Process in Immunity", BioMed Research International, vol. 2017, Article ID 9042851, 18 pages.

Aguilar-Ruiz, S., et al., "Human CD16+ and CD16+ monocyte subsets display unique effector properties in inflammatory conditions in vivo", Journal of Leukocyte Biology, (2011) vol. 90, pp. 1119-1131.

Schlam D, Bagshaw RD, Freeman SA, Collins RF, Pawson T, Fairn GD, Grinstein S. 2015. Phosphoinositide 3-kinase enables phagocytosis of large particles by terminating actin assembly through Rac/Cdc42 GTPase-activating proteins. Nature Communications 6:8623.

Schlam, et al., "Phosphoinositide 3-kinase enables phagocytosis of large particles by terminating actin assembly through Rac/Cdc42 GRPase-activating proteins" (2015) Nature Communications.

Tseng D, Volkmer JP, Willingham SB, Contreras-Trujillo H, Fathman JW, Fernhoff NB, Seita J, Inlay MA, Weiskopf K, Miyanishi M, Weissman IL. 2013. Anti-CD47 antibody-mediated phagocytosis of cancer by macrophages primes an effective antitumor T-cell response. PNAS 110:11103-11108.

Tsutsui, et al. "The use of microbubbles to target drug delivery" Cardiovascular Ultrasound (2004) 2:23.

Tuveson DA, Carter RH, Soltoff SP, Fearon DT. 1993. CD19 of B cells as a surrogate kinase insert region to bindphosphatidylinositol 3-kinase. Science 260:986-989.

(56) References Cited

OTHER PUBLICATIONS

Weischenfeldt J, Porse B. 2008. Bone Marrow-Derived Macrophages (BMM): Isolation and Applications. Cold Spring Harbor Protocols 2008:pdb.prot5080.
Xiao X, Ho M, Zhu Z, Pastan I, Dimitrov DS. 2009. Identification and characterization of fully human anti-CD22 monoclonal antibodies. mAbs 1:297-303.
Yong, C., et al, "A role for multiple chimeric antigen receptor-expressing leukocytes in antigen-specific responses to cancer" (2016) Oncotarget, vol. 7, No. 23 pp. 34582-34598.

* cited by examiner

Before Isolation of Monocytes:

| Donor | Leukopak Size | Monocyte Yield (Spec Sheet) | Total PBMCs | Column Type | Number of Columns Used | CD3+ % | CD19+ % | CD56+ % | CD14+% |
|---|---|---|---|---|---|---|---|---|---|
| 1 | Full, 291mL | 2.28e9 | 5.5e9 | LS | 8 | 57.8 % | 11.4 % | 13% | 15.2% |

After Isolation of Monocytes (Positive Selection):

| Donor | Monocytes Isolated | Viability % | CD3+ % | CD19+ % | CD56+ % | CD14+/ CD16(-)% | CD14- /CD16+% | CD14+/ CD16+% |
|---|---|---|---|---|---|---|---|---|
| 1 | *9.3e8 | >95% | 2% | 0.29% | 2.53% | 66.9% | 6% | 22% |

FIG. 4

Process Developed For CD14+CD16- Cell Isolation

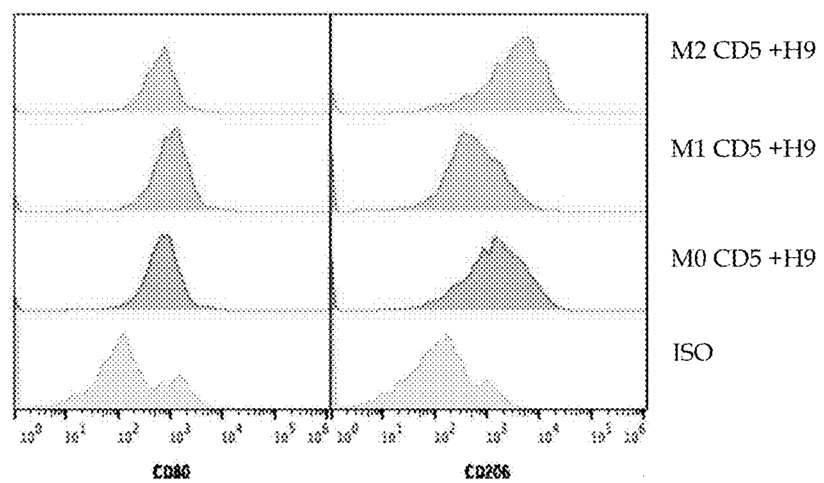
FIG. 15Bii

PBMC

Monocytes (Protocol 1)

PBMC

Monocytes (Protocol 2)

THERAPEUTIC CELL COMPOSITIONS AND METHODS OF MANUFACTURING AND USE THEREOF

CROSS REFERENCE

This application claims the benefit of U.S. Provisional Application No. 62/946,896, filed Dec. 27, 2019; which application is incorporated herein by reference in their entirety.

SEQUENCE LISTING

The instant application contains a Sequence Listing which has been filed electronically in ASCII format and is hereby incorporated by reference in its entirety. Said ASCII copy, created on Mar. 29, 2020, is named 56371-708_201_SL.txt and is 12,017 bytes in size.

BACKGROUND

Circulating monocytes represent a versatile and dynamic cell population, composed of multiple subsets which differ in phenotype, size, morphology, and transcriptional profiles and are defined by their location in the blood (Geissmann et al., 2003; Cros et al., 2010; Ingersoll et al., 2010; Wong et al., 2011; Mildner et al., 2013a). These discrete monocyte subsets can be distinguished by the expression of CD14 and CD16 in humans and Ly6C, CCR2, and CX3CR1 in mice. In humans, CD14+ CD16− (classical) monocytes make up ~85% of the circulating monocyte pool, whereas the remaining ~15% consist of CD14+ CD16+ (intermediate) and CD14lo CD16+ (nonclassical) monocytes (Passlick et al., 1989; Wong et al., 2011). Similarly, in mice, two populations of monocytes have been described: Ly6Chi CCR2+ CX3CR1int and Ly6Clo CCR2− CX3CR1hi, representing classical and nonclassical monocytes, respectively (Geissmann et al., 2003). Monocyte egression from the bone marrow requires expression of the chemokine receptor CCR2, which is restricted to CD14+ CD16− classical monocytes.

Classical monocytes are rapidly recruited to sites of cancer, infection, autoimmunity and injury, where they exhibit considerable functional plasticity, differentiating into a number of downstream cells such as dendritic cells and macrophages. Classical monocytes replenish resident peripheral monocyte-derived cells under steady-state conditions.

SUMMARY

The development of cell therapies using myeloid cells, including macrophages and dendritic cells is appealing as these cells act as the bridge between innate an adaptive immunity. On one hand, harnessing the inflammatory abilities of these cells including, for example, phagocytosis, cytokine production, chemokine production, antigen presentation/cross-presentation, and T cell activation has the potential to revolutionize treatment for cancer. Harnessing the immune regulatory abilities of these cells also have the potential to treat numerous autoimmune disorders as well as neurodegenerative disease such as Alzheimers and other protein accumulation disorders.

Historically the production of macrophages and dendritic cells has relied on the positive selection of CD14+ monocytes from the blood and subsequent culture in MCSF (macrophage) or GMCSF+IL4 (or other factors) for greater than 5 days. This process results in the maturation of the monocytes into macrophages or dendritic cells respectively. This process results in changes to these cells that reduces many of the key functions needed to be able to migrate to sites of disease. Such cells have been used for tumor vaccine and other purposes. While these cells appear to have strong functional capabilities in vitro, upon infusion into hosts they have many issues including: a short life span upon re-infusion into humans; downregulation of critical chemokine receptors needed to be able to traffic into sites of inflammation/tumors—resulting in poor trafficking; the need to culture for more than 5 days (usually at least 7 days) to prepare them for in vivo application.

These issues have potentially resulted in suboptimal outcomes in clinical studies whereby using macrophages and DC's has been tested. This is not because the original cells were not capable of having an impact, but because the processes used to generate these cell reduced their abilities. The processes described herein focuses on harnessing the power of CD14+ monocytes without altering their intrinsic abilities.

In consideration of the above, provided herein is a method and compositions to generate a population of myeloid cells from blood (without the requirement for any form of stem cell mobilization) that shows the ability to differentiate into downstream precursor cells, the ability to track into sites of cancer, infection, inflammation, neurodegeneration and autoimmunity and the ability to differentiate into a number of downstream effector cells. These cells can be engineered with a Chimeric Antigen Receptor and/or to express soluble factors and/or to present molecules and antigens to other arms of the immune system.

Also provided herein are methods and compositions to generate a pool of myeloid cells that can be engineered or modified for therapeutic purposes (e.g. loading with antigen, engineered with CAR's, etc)

Further, provided herein are methods to generate a pool of myeloid cells that can be frozen and thawed for future use (e.g. above).

Provided herein are methods for generation of mRNA construct with modified LTR for longer expression in myeloid cells.

A composition is provided herein, comprising a population of CD14+/CD16− cells, wherein the population of CD14+/CD16− cells is an engineered population of cells and/or comprises an exogenous agent.

A composition comprising a population of cells is hereby disclosed, wherein the population of cells is an engineered population of cells and/or comprises an exogenous agent, wherein the population of cells is CD14+ and/or CD16−, and wherein (a) the population of cells expresses CCR2 and/or CCR5; (b) the population of cells is CD63+; (c) the population of cells is CD56−, CD3−, and/or CD19−; (d) the population of myeloid cells comprises less than 40% macrophage cells and/or less than 10% dendritic cells (DCs); and/or (e) the exogenous agent comprises a recombinant nucleic acid comprising a sequence encoding a chimeric antigen receptor (CAR) and (f) the population of cells lacks tonic signaling through the CAR.

A composition comprising a population of cells is hereby disclosed, wherein the population of cells is an engineered population of cells and/or comprises an exogenous agent, wherein the population of cells is CD14+ and/or CD16−, and wherein (a) the population of cells is unpolarized myeloid cells; (b) the population of cells differentiates into effector cells in the subject after administration; (c) the population of cells infiltrates into a diseased site of the subject after administration or migrates to a diseased site of the subject after administration; or (d) the population of cells have a life-span of at least 5 days in the subject after administration.

Provided herein is a pharmaceutical composition comprising the composition of any one of the embodiments described above and a pharmaceutically acceptable excipient.

Also provided herein is a method of treating a disease or condition in a subject in need thereof, comprising: administering the pharmaceutical composition of the embodiment described above to the subject.

Provided herein is a method of treating a disease or condition in a subject in need thereof, comprising: administering to the subject a pharmaceutical composition comprising a population of cells, wherein the population of cells is an engineered population of cells and/or comprises an exogenous agent, wherein the population of cells is CD14+ and/or CD16−, and wherein (a) the pharmaceutical composition is administered to the subject within 72 hours after (i) the exogenous agent has been introduced into the population of cells or (ii) the population of cells has been engineered; (b) the population of myeloid cells has been cultured for less than 48 days ex vivo prior to administration; (c) the population of cells is obtained by a method that does not comprise stem cell mobilization; and/or (d) the population of cells is obtained by negative selection.

Provided herein is a method of treating a disease or condition in a subject in need thereof, comprising: administering to the subject a composition comprising a myeloid cell, wherein the myeloid cell (a) is characterized by one or more of: (i) having a strong CD14 expression; (ii) having a low or undetectable CD16 expression; (iii) expressing CCR2 and/or CCR5; (iv) having an ability to differentiate into multiple myeloid lineage subtypes upon receiving one or more suitable stimuli; and, (b) comprises an exogenous agent, wherein when modified by the exogenous agent ex vivo, the exogenous agent does not alter differentiation or polarization state of the myeloid cell.

In some embodiments, the myeloid cell is CD16− (CD16 negative) or CD16low (CD16 low).

In some embodiments, the myeloid cell is CD14+ (CD14 positive).

In some embodiments, the myeloid cell is CCR2+ (CCR2 positive) and/or CCR5+ (CCR5 positive).

In some embodiments, the myeloid cell is capable of differentiating into an effector cell in the subject after administering the pharmaceutical composition. In some embodiments, the myeloid cell is capable of migrating to a diseased site of the subject after administering the pharmaceutical composition. In some embodiments, the myeloid cell is capable of infiltrating into a diseased site of the subject after administering the pharmaceutical composition.

In some embodiments, the myeloid cell is CD14+/CCR2+.

In some embodiments, the myeloid cell is CD14+/CCR5+.

In some embodiments, the myeloid cell is CD14+/CCR2+/CCR5+.

In some embodiments, the myeloid cell is CD63+.

In some embodiments, the exogenous agent is a recombinant nucleic acid, a peptide, a carbohydrate, a lipid or a small molecule. In some embodiments, the exogenous agent comprises a recombinant nucleic acid comprising a sequence encoding a peptide, wherein the peptide is a chimeric antigen receptor (CAR).

In some embodiments, the myeloid cell has been cultured for less than 2 days in vitro at the time of administering the pharmaceutical composition.

In some embodiments, the myeloid cell retains cellular plasticity at the time of administering the pharmaceutical composition.

In some embodiments, at the time of administering, the myeloid cell expresses a CAR.

In some embodiments, at the time of administering the pharmaceutical composition, the myeloid cell does not exhibit a tonic signaling by the CAR.

In some embodiments, the population of myeloid cells is obtained by a method comprising subjecting an isolated plurality of myeloid cells to a manipulation in vitro.

In some embodiments, the population of myeloid cells is obtained by a method that does not comprise stem cell mobilization.

In some embodiments, the plurality of myeloid cells are isolated from a biological sample by a negative selection using antibody-mediated binding of one or more myeloid cells in the biological sample. In some embodiments, the negative selection is performed using flow cytometry. In some embodiments, the plurality of isolated myeloid cells are (i) CD3− (negative), (ii) CD16− (negative) or CD16low, (iii) CD19− (negative); (iv) CD56− (negative); and (v) CD14+ (positive).

In some embodiments, the population of myeloid cells are CD16−CD56−CD3−CD19− cells that are obtained by a negative selection of a plurality of myeloid cells isolated from a biological sample.

In some embodiments, the biological sample is a peripheral blood sample. In some embodiments, the biological sample is an apheresis sample. In some embodiments, the biological sample is heterologous or autologous to the subject to whom the pharmaceutical composition comprising the myeloid cell is administered.

In some embodiments, at least 50% of myeloid cells of the population of myeloid cells is undifferentiated. In some embodiments, the population of myeloid cells comprises M0 monocytes. In some embodiments, the population of myeloid cells comprises M1 monocytes. In some embodiments, the population of myeloid cells comprises M2 monocytes.

In some embodiments, at least 50% of myeloid cells of the population of myeloid cells are unpolarized.

In some embodiments, the subject is human. In some embodiments, the disease or condition is selected from a cancer, an infection, an autoimmune disease, an inflammatory disease, a metabolic disease, a neurodegenerative disease and a monogenic, polygenic or multifactorial disease or disorder. In some embodiments, the disease or condition is a cancer. In some embodiments, the disease or condition is a bacterial, viral, mycological or parasitic infection. In some embodiments, the disease or condition is neurodegeneration.

Provided herein is a method for isolating therapeutically effective myeloid cells, comprising: (a) negatively selecting therapeutically effective myeloid cells from a biological sample comprising myeloid cells, by (i) contacting the biological sample with one or more antibodies comprising anti-CD16 antibody, anti-CD56 antibody, anti-CD3 antibody, or anti-CD19 antibody, and (ii) eliminating the cells in the biological sample that are bound by the one or more antibodies, thereby isolating therapeutically effective myeloid cells that are relatively unperturbed in the process.

In some embodiments, the therapeutically effective myeloid cells are isolated from a biological sample by positive selection. For example, the therapeutically effective myeloid cells are isolated from a biological sample by binding the cells with an anti-CD14 antibody.

In some embodiments, the isolated therapeutically effective myeloid cells are CD14+.

In some embodiments, the isolated therapeutically effective myeloid cells are CD14hi.

In some embodiments, the isolated therapeutically effective myeloid cells are CD16− or CD16low.

In some embodiments, the isolated therapeutically effective myeloid cells retain the ability to differentiate into myeloid lineage subsets in response to a suitable stimulus.

In some embodiments, the isolated therapeutically effective myeloid cells are capable of further differentiating into polarized monocytes, macrophages, DC1, DC2, DC3, DC4, DC5 DC6 dendritic cells, or any combination thereof.

In some embodiments, the isolated therapeutically effective myeloid cells retain the ability to polarize towards M1 and M2 phenotypes in response to a suitable stimulus.

Provided herein is a method for generating a population of myeloid cells for treating a subject in need thereof, the method comprising: (i) isolating a plurality of myeloid cells from a biological sample, wherein the plurality of myeloid cells exhibits cellular plasticity; (ii) subjecting the plurality of myeloid cells isolated from the biological sample to a manipulation in vitro using an exogenous agent, and obtaining the population of myeloid cells; wherein the manipulation in vitro does not alter the cellular plasticity of the plurality of myeloid cells; and (iii) preparing a therapeutic composition comprising the population of myeloid cells and an acceptable excipient.

In some embodiments, the subject is human.

In some embodiments, the biological sample is a peripheral blood sample, an apheresis sample, a leukapheresis sample, or an umbilical cord blood sample. In some embodiments, the biological sample is derived from the subject. In some embodiments, the biological sample is derived from a suitable human donor.

In some embodiments, isolating a plurality of myeloid cells from a biological sample comprises isolating CD14+ cells by a negative selection.

In some embodiments, the negative selection is achieved by contacting cells in the human sample with one or more antibodies selected from a group consisting of anti-CD16 antibody, anti-CD56 antibody, anti-CD3 antibody, and anti-CD19 antibody and immobilizing or eliminating the cells in the human sample that are bound by the one or more antibodies.

In some embodiments, the negative selection is performed by flow cytometry.

In some embodiments, the plurality of myeloid cells isolated from the biological sample are CD14+, and do not express CD3, CD19, CD56 and/or CD16.

In some embodiments, the myeloid cells are undifferentiated, or unpolarized.

In some embodiments, the exogenous agent is a recombinant nucleic acid, a peptide, a carbohydrate, a lipid or a small molecule.

In some embodiments, the manipulation comprises genetically engineering the plurality of myeloid cells. In some embodiments, the manipulation comprises introducing a recombinant nucleic acid comprising a sequence encoding a peptide to the plurality of myeloid cells.

In some embodiments, the recombinant nucleic acid is an RNA.

In some embodiments, the recombinant nucleic acid is an mRNA.

In some embodiments, the population of myeloid cells, upon introduction of the nucleic acid comprising a sequence encoding a peptide, expresses the peptide.

In some embodiments, the peptide is a chimeric antigen receptor (CAR).

In some embodiments, the peptide comprises: (i) a transmembrane domain; (ii) an extracellular region comprising at least a target-binding domain that binds to a surface component of a second cell; and (iii) an intracellular region comprising one or more signaling domains.

In some embodiments, the second cell is a diseased cell or a cancer cell.

In some embodiments, the peptide comprises at least one intracellular phagocytosis signaling domain.

In some embodiments, the intracellular phagocytic signaling domain is operably linked to the extracellular target-binding domain and is configured to be activated upon binding of the extracellular target-binding domain to the surface component of the second cell.

In some embodiments, the introducing a recombinant nucleic acid comprises introducing via electroporation or nucleoporation.

In some embodiments, the introducing a recombinant nucleic acid comprises introducing via chemical delivery.

In some embodiments, the recombinant nucleic acid is stably incorporated into the genome of the cell. In some embodiments, the incorporating is via activation of one or more of a transposase, an integrase, an endonuclease, a recombinase, and a reverse transcriptase.

In some embodiments, preparing of the composition comprises suspending the cells in a pharmaceutically acceptable excipient.

In some embodiments, the population of myeloid cells retain cellular plasticity and ability to differentiate into multiple myeloid lineages following suitable stimuli.

In some embodiments, the population of myeloid cells do not exhibit a tonic signaling by the CAR. The population of myeloid cells described above can express a functional CAR, and are capable of exhibiting CAR-mediated antigen specific response. In some embodiments, the acceptable excipient is a buffer, a cell culture medium comprising nutrients, DMSO, glycerol, or a combination thereof.

In some embodiments, the composition is frozen until further use. In some embodiments, the method is able to be conducted in less than 12 hours, less than 10 hours, less than 8 hours, less than 6 hours, less than 4 hours, or less than 2 hours.

In some embodiments, the method is completed in 2 hours or less.

In some embodiments, the plurality of myeloid cells is subjected to gene modification and/or editing, thereby obtaining the population of myeloid cells. In some embodiments, the plurality of myeloid cells is subjected contacting with one or more antigenic peptides, thereby obtaining the population of myeloid cells that are antigen-loaded. The method of manufacturing a population of myeloid cells as provided herein is able to be conducted in about 6 hours or less; and wherein the population of myeloid cells are undifferentiated or unpolarized, exhibit cellular plasticity and lack tonic signaling.

In some embodiments, the population of myeloid cells for cell therapy comprises any one or more of: (a) greater than about 50% of live cells in the population that are CD14+ CD16−; (b) greater than about 50% of live cells in the population that are CCR2+ and/or CCR5+; (c) less than at least 50% of live cells in the population that express one or more of CD64, CD68, CD80, CD86, CD163, CD206, CD200R, CD31, CD71, CLEC9A, CD1C, and AXL/SIGLEC6; (d) an M0 monocyte, (e) an M1 monocyte, (f) an M2 monocyte, (g) a dendritic cell, and (h) a pre-dendritic cells or a dendritic precursor cell.

Provided herein is a population of myeloid cells for use in cell therapy comprising undifferentiated or unpolarized cells, that have been isolated from a biological sample, and further manipulated in vitro using an external agent selected from a recombinant nucleic acid, a peptide, a carbohydrate, a compound and a small molecule, wherein, a myeloid cell in the population of myeloid cells are CD14+ CD16−; or are CD14hi and CD16lo; and exhibit one or more of the following: (i) a cellular plasticity, (ii) an ability to differentiate into multiple myeloid lineages, (iii) an ability to migrate in vivo to a diseased tissue, (iv) an ability to infiltrate a diseased tissue, and (v) an ability sequester and/or destroy a disease-causing cell, tissue or organism.

In some embodiments, the population of myeloid cells are isolated via negative selection. In some embodiments, the exogenous agent is a recombinant nucleic acid, a peptide, a carbohydrate, a lipid or a small molecule.

In some embodiments, a cell of the population of myeloid cells comprises a recombinant nucleic acid having a sequence encoding a peptide.

In some embodiments, a cell of the population of myeloid cells comprises a recombinant nucleic acid having a sequence encoding a CAR.

In some embodiments, a cell of the population of myeloid cells expresses a CAR that exhibits CAR mediated activation.

In some embodiments, a cell of the population of myeloid cells expresses a CAR, and does not exhibit tonic signaling by the CAR.

In some embodiments, a cell of the population of myeloid cells is CD14+. In some embodiments, a cell of the population of myeloid cells is CD16−. In some embodiments, a cell of the population of myeloid cells is CD14highCD16low. In some embodiments, a cell of the population of myeloid cells is CD56−. In some embodiments, a cell of the population of myeloid cells is CD3−. In some embodiments, a cell of the population of myeloid cells is CD19−. In some embodiments, a cell of the population of myeloid cells expresses one or more chemokine receptors. In some embodiments, a cell of the population of myeloid cells expresses CCR2. In some embodiments, a cell of the population of myeloid cells expresses CCR5. In some embodiments, a cell of the population of myeloid cells expresses CCR2 and CCR5. In some embodiments, a cell of the population of myeloid cells is CD16−CD56−CD3−CD19−.

Provided herein is a pharmaceutical composition comprising the population of myeloid cells.

Provided herein is a population of myeloid cells for use in a cancer therapy.

In some embodiments, provided herein the population of myeloid cells, for use in a therapy for neurodegeneration. In some embodiments, a cell in the population exhibit enhanced immunogenicity following administration as a cell therapy, compared to a cell that has not been manipulated in vitro. In some embodiments, a cell in the population exhibit enhanced cellular migration to a diseased tissue following administration as a cell therapy, compared to a cell that has not been manipulated in vitro. In some embodiments, a cell in the population exhibit enhanced phagocytic ability following administration as a cell therapy, compared to a cell that has not been manipulated in vitro. In some embodiments, a cell in the population exhibit enhanced cytotoxicity following administration as a cell therapy, compared to a cell that has not been manipulated in vitro.

In some embodiments, the population of myeloid cells, for use as a monotherapy. In some embodiments, the population of myeloid cells, for use as a combination therapy.

Provided herein is a method for making a human myeloid cell for treating a human subject in need thereof, comprising: (i) obtaining a plurality of myeloid cells comprising undifferentiated or unpolarized myeloid cells from an allogeneic or autologous biological sample via a negative selection using a plurality of antibodies comprising at least anti-CD16 antibody, anti-CD3 antibody, anti-CD56 antibody and anti-CD19 antibody; (ii) engineering, culturing, stabilizing, activating, enriching and/or expanding the cells from step (i); and (iii) administering the cells from step (ii) to the subject; wherein the time lapse from obtaining in (i) to administering in (iii) is less than about 3 days.

In some embodiments, the biological sample is a peripheral blood sample.

In some embodiments, the biological sample is an apheresis sample.

In some embodiments, the cells from step (ii) are CD14+ CD16− or CD14hi and CD16lo.

In one aspect, provided herein is a pharmaceutical composition comprising (a) a population of cells comprising a recombinant polynucleic acid, wherein the recombinant polynucleic acid comprises a sequence encoding a chimeric fusion protein (CFP) or a sequence encoding an antigenic peptide, wherein: (i) at least 50% of the cells in the population of cells are CD14+ and CD16−, and (ii) less than 10% of the cells in the population of cells are dendritic cells; and (b) a pharmaceutically acceptable excipient.

In some embodiments, at least 50% of the cells in the population of cells are CCR2+ and/or CCR5+. In some embodiments, at least 50% of the cells in the population of cells are CD63+. In some embodiments, at least 50% of the cells in the population of cells are CD56−, CD3−, and/or CD19−.

In some embodiments, less than 40% of the cells in the population of cells are macrophage cells. In some embodiments, the composition comprises: (a) at least 50% of the cells in the population of cells are CCR2+ and/or CCR5+; (b) at least 50% of the cells in the population of cells are CD63+; (c) at least 50% of the cells in the population of cells are CD56−, CD3−, and/or CD19−; and (d) less than 40% of the cells in the population of cells are macrophage cells.

In some embodiments, the population of cells is a population of unpolarized or undifferentiated myeloid cells.

In some embodiments, the recombinant polynucleic acid comprises a sequence encoding a CFP, and the population of cells lacks tonic signaling through the CFP.

In some embodiments, recombinant polynucleic acid comprises a sequence encoding a CFP, wherein the CFP comprises: (a) an extracellular domain comprising an antigen binding domain, and (b) a transmembrane domain operatively linked to the extracellular domain. In some embodiments, the antigen binding domain is a CD5 binding domain or a HER2 binding domain. In some embodiments the CFP further comprises an intracellular domain derived from a phagocytic receptor or a scavenger receptor. In some embodiments, the CFP comprises: (a) an extracellular domain comprising: (i) a scFv that specifically binds CD5 or HER2, and (ii) a hinge domain derived from CD8, or CD28 or an extracellular domain of CD68 or a portion thereof; (b) a CD8 transmembrane domain, a CD28 transmembrane domain or a CD68 transmembrane domain; and (c) an intracellular domain comprising at least two intracellular signaling domains, wherein the at least two intracellular signaling domains comprise (i) a first intracellular signaling domain derived from FcγR or FcεR, an (ii) a second intracellular signaling domain that: (A) comprises a PI3-kinase (PI3K) recruitment domain, or (B) is derived from CD40. In some embodiments, the recombinant polynucleic acid comprises a sequence encoding an antigenic peptide, wherein the antigenic peptide is a CMVpp65 peptide.

In one aspect, provided herein is a method of treating a disease or condition in a subject in need thereof, comprising: administering the pharmaceutical composition described above, to the subject.

In some embodiments, the cells of the population of cells: (a) differentiate into effector cells in the subject after administration; (b) infiltrate into a diseased site of the subject after administration or migrate to a diseased site of the subject after administration; or (c) have a life-span of at least 5 days in the subject after administration. In some embodiments, the population of cells is from the subject. In some embodiments, the pharmaceutical composition is administered to the subject within 72 hours after the recombinant polynucleic acid has been introduced into the population of cells. In some embodiments, the population of cells has been cultured for less than 48 hours ex vivo prior to administration.

In one aspect, provided herein is a method of negatively selecting cells for preparing the pharmaceutical composition of claim 1, the method comprising: (a) contacting a biological sample from a human subject with an anti-CD16 antibody and one or more antibodies selected from anti-CD56 antibody, anti-CD3 antibody and anti-CD19 antibody, and (b) collecting cells in the biological sample that are not bound by the anti-CD16 antibody and not bound by the one or more antibodies, (c) introducing a recombinant polynucleic acid comprising a sequence encoding a CFP into cells collected from (b), thereby forming a population of cells, wherein: (i) at least 50% of the cells in the population of cells are CD14+ and CD16−, and (ii) less than 10% of the cells in the population of cells are dendritic cells. In some embodiments, the method comprises flow cytometry.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

FIG. 4 shows tables indicating total cell numbers used and recovered by antibody mediated selection and isolation of CD14+ cells from apheresis product, and percentages of the indicated cellular subtypes. Upper panel, before selection; lower panel, after selection.

FIG. 15Bii shows data indicating that the CD80 or CD206 levels are not altered with the treatments indicated in FIG. 15A.

FIG. 18A (lower panel) shows cell population expressing CD14, CD3, CD19 and CD56 following isolation of monocytes (Protocol 1).

FIG. 19A (lower panel) shows cell population expressing CD14, CD3, CD19 and CD56 following isolation of monocytes (Protocol 2).

DETAILED DESCRIPTION

Figure 1:
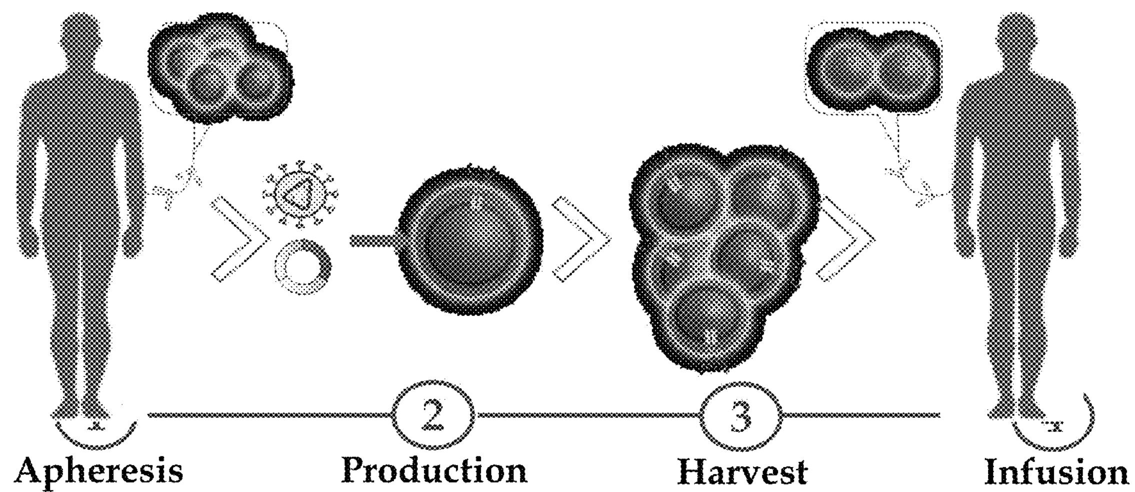
FIG. 1 depicts a schematic overview of the clinical process of isolated myeloid cells.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. The details of one or more particular embodiments are set forth in the description below.

Throughout the specification, the term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

An "agent" is any small molecule chemical compound, antibody, nucleic acid molecule, or polypeptide, or fragments thereof.

An "alteration" or "change" is an increase or decrease. An alteration can be by as little as 1%, 2%, 3%, 4%, 5%, 10%, 20%, 30%, or by 40%, 50%, 60%, or even by as much as 70%, 75%, 80%, 90%, or 100%.

An "antigen" is a molecule capable of stimulating an immune response. Antigens recognized by T cells, whether helper T lymphocytes (T helper (TH) cells) or cytotoxic T lymphocytes (CTLs), are not recognized as intact proteins, but rather as small peptides that associate with class I or class II MHC proteins on the surface of cells. During the course of a naturally occurring immune response, antigens that are recognized in association with class II MHC molecules on antigen presenting cells (APCs) are acquired from outside the cell, internalized, and processed into small peptides that associate with the class II MHC molecules.

A "biologic sample" is any tissue, cell, fluid, or other material derived from an organism. As used herein, the term "sample" includes a biologic sample such as any tissue, cell, fluid, or other material derived from an organism.

"Specifically binds" refers to a compound (e.g., peptide) that recognizes and binds a molecule (e.g., polypeptide), but does not substantially recognize and bind other molecules in a sample, for example, a biological sample.

The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

"Phagocytosis" as used herein can be used interchangeably with "engulfment." The process of phagocytosis is closely coupled with immune response, and most importantly, is the first step of the immune response, which is antigen presentation. The processing of exogenous antigens follows their uptake into professional antigen presenting cells by some type of endocytic event. Phagocytosis also facilitates antigen presentation: antigens from the phagocytosed cells or pathogen, including cancer antigens are processed and presented on the cell surface of APCs.

"Antigen presenting cell" or "APC" includes professional antigen presenting cells (e.g., B lymphocytes, macrophages, monocytes, dendritic cells, Langerhans cells), as well as other antigen presenting cells (e.g., keratinocytes, endothelial cells, astrocytes, fibroblasts, oligodendrocytes, thymic epithelial cells, thyroid epithelial cells, glial cells (brain), pancreatic beta cells, and vascular endothelial cells). These cells are phagocytes. An APC further expresses the Major Histocompatibility complex (MHC) molecules and can display foreign antigen complexed with MHC on its surface to be contacted and recognized by T cells, which triggers T cell activation and immune response. Professional antigen-presenting cells, notably dendritic cells, play a key role in stimulating naive T cells—but nonprofessional antigen-presenting cells, such as fibroblasts, may also contribute to this process. APCs can also cross-present peptide antigens by processing exogenous antigens and presenting the processed antigens on class I MHC molecules. Antigens that give rise to proteins that are recognized in association with class I MHC molecules are generally proteins that are produced within the cells, and these antigens are processed and associate with class I MHC molecules.

A phagocytic cell of the present disclosure that expresses a recombinant nucleic acid encoding that binds to an antigen or an epitope on a cancer cell, engulfs the cancer cell to remove it from the body, The term "epitope" includes any protein determinant capable of specific binding to an antibody, antibody peptide, and/or antibody-like molecule (including but not limited to a T cell receptor) as defined herein.

An engineered cell is a cell, as described herein that has been manipulated to enhance a function, for example by a genetic engineering method, to express one or more exogenous proteins, such as a fusion protein, for example, a CAR. In some embodiments, an engineered cell as used herein refers to a myeloid cell that expresses a transgene, or that has been gene edited. In some embodiments, engineered cell or engineered myeloid cell is a myeloid cell that expresses a recombinant fusion protein, such as a phagocytic receptor fusion protein. In some embodiments, the phagocytic receptor fusion protein, as used herein, (CAR) comprises an extracellular antigen binding domain specific to an antigen of a target cell, fused to the phagocytic receptor. A target cell is, for example, a cancer cell. In some embodiments, the engineered phagocytic cell, after engulfment of the cancer cell may present the cancer antigen on its cell surface to activate a T cell.

An effector myeloid cell, as used herein cell is a myeloid cell or a myeloid progenitor cell, that is functionally competent to be further formulated into a pharmaceutical composition for cellular therapy by administering the pharmaceutical composition to a subject in need thereof. In some embodiments, an effector myeloid cell is isolated (and/or enriched) from a biological sample, for example, peripheral blood mononuclear cells, and may be further manipulated for example, to express a transgene, or comprises an exogenously edited genome, and exhibit characteristics that may include but are not limited to: ability to specifically phagocytose and eliminate target cells or pathogens; ability to further differentiated in response to a differentiation-triggering signal, ability to be further activated in response to an activation signal, is relatively long-lasting, has longer lifespan compared to a terminally differentiated myeloid cells; can migrate to lymph nodes when administered in vivo.

A "receptor" is to be understood as meaning a biological molecule or a molecule grouping capable of binding a ligand. A receptor can serve to transmit information in a cell, a cell formation or an organism. The receptor comprises at least one receptor unit and can contain two or more receptor units, where each receptor unit can consist of a protein molecule, e.g., a glycoprotein molecule. The receptor has a structure that complements the structure of a ligand and can complex the ligand as a binding partner. Signaling information can be transmitted by conformational changes of the receptor following binding with the ligand on the surface of a cell. According to the present disclosure, a receptor can refer to proteins of MHC classes I and II capable of forming a receptor/ligand complex with a ligand, e.g., a peptide or peptide fragment of suitable length.

A "ligand" is a molecule which is capable of forming a complex with a receptor. According to the present disclosure, a ligand is to be understood as meaning, for example, a protein, a glycoprotein, carbohydrate, lipoprotein, or any component that binds to a receptor. In some embodiments, a receptor has a specific ligand. In some embodiments, a receptor may have promiscuous binding to a its ligand, in which case it can bind to several ligands that share at least a similarity in structural configuration, charge distribution or any other physicochemical characteristic. A ligand may be a biomolecule. A ligand may be an abiotic material, for example, $TiO_2$ is the ligand for a scavenger receptor SRA1.

In some embodiments, the phagocytic receptor fusion protein may comprise an extracellular domain, which comprises an antibody or a portion thereof that can bind to a cancer antigen or a cell surface molecule on a cancer cell. The term "antibody" as used herein includes IgG (including IgG1, IgG2, IgG3, and IgG4), IgA (including IgA1 and IgA2), IgD, IgE, IgM, and IgY, and is meant to include whole antibodies, including single-chain whole antibodies, and antigen-binding (Fab) fragments thereof. Antigen-binding antibody fragments include, but are not limited to, Fab, Fab' and F(ab')2, Fd (consisting of VH and CH1), single-chain variable fragment (scFv), single-chain antibodies, disulfide-linked variable fragment (dsFv) and fragments comprising either a VL or VH domain. The antibodies can be from any animal origin. Antigen-binding antibody fragments, including single-chain antibodies, can comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies can be monoclonal, polyclonal, chimeric, humanized, and human monoclonal and polyclonal antibodies which, e.g., specifically bind an HLA-associated polypeptide or an HLA-peptide complex. A person of skill in the art will recognize that a variety of immunoaffinity techniques are suitable to enrich soluble proteins, such as soluble HLA-peptide complexes or membrane bound HLA-associated polypeptides, e.g., which have been proteolytically cleaved from the membrane. These include techniques in which (1) one or more antibodies capable of specifically binding to the soluble protein are immobilized to a fixed or mobile substrate (e.g., plastic wells or resin, latex or paramagnetic beads), and (2) a solution containing the soluble protein from a biological sample is passed over the antibody coated substrate, allowing the soluble protein to bind to the antibodies. The substrate with the antibody and bound soluble protein is separated from the solution, and optionally the antibody and soluble protein are disassociated, for example by varying the pH and/or the ionic strength and/or ionic composition of the solution bathing the antibodies. Alternatively, immunoprecipitation techniques in which the antibody and soluble protein are combined and allowed to form macromolecular aggregates can be used. The macromolecular aggregates can be separated from the solution by size exclusion techniques or by centrifugation.

A peptide or polypeptide may be used interchangeably, and as used herein can be a "protein", including but not limited to a glycoprotein, a lipoprotein, a cellular protein or a membrane protein. A polypeptide may comprise one or more subunits of a protein. A polypeptide may be encoded by a recombinant nucleic acid. In some embodiments, polypeptide may comprise more than one peptides in a single amino acid chain, which may be separated by a spacer, a linker or peptide cleavage sequence. A polypeptide may be a fused polypeptide. A polypeptide or a protein may comprise one or more domains. A domain is a structural portion of a protein with a defined function, a polypeptide or a protein may comprise one or more modules. A module is domain or a portion of the domain or portion of a protein with a specific function. A module may be a structural module of a protein, designated by its structural embodiments. A moiety is a portion of polypeptide, a protein or a nucleic acid, having a specific structure or perform a specific function. For example, a signaling moiety is a specific unit within the larger structure of the polypeptide or protein or a recombinant nucleic acid, which (or the protein portion encoded by it in case of a nucleic acid) engages in a signal transduction process, for example a phosphorylation. A module, a domain and a moiety, as used herein, can be used interchangeably, unless a specific structural or functional orientation is otherwise defined in the text. A motif is a structural entity in a biomolecule. A signaling motif in a protein or polypeptide, for example, refers to a stretch of amino acids on the protein or polypeptide which contain an amino acid which may be phosphorylated, dephosphorylated or can serve as a binding site of another signaling molecule. Similarly, in case of nucleic acids, for example, TNF mRNA has a conserved motif, UUAUUUAUU, in the 3'UTR to which mRNA destabilizing enzymes such as zinc-finger binding protein 36 family members bind.

The term "recombinant nucleic acid" refers to synthetic nucleic acid having a nucleotide sequence that is not naturally occurring. A recombinant nucleic acid may be synthesized in the laboratory. A recombinant nucleic acid is prepared by using recombinant DNA technology by using enzymatic modification of DNA, such as enzymatic restriction digestion, ligation, and DNA cloning. A recombinant nucleic acid as used herein can be DNA, or RNA. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell.

The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

The term "vectors" refers to a nucleic acid molecule capable of transporting or mediating expression of a heterologous nucleic acid. A plasmid is a species of the genus encompassed by the term "vector." A vector typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

As used herein, the terms "determining", "assessing", "assaying", "measuring", "detecting" and their grammatical equivalents refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

The terms "isolated," "purified", "biologically pure" and their grammatical equivalents refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of the present disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications can give rise to different isolated proteins, which can be separately purified.

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three dimensional structure, and may perform any function, known or unknown. A polynucleotide may comprise one or more analogs (e.g. altered backbone, sugar, or nucleobase). If present, modifications to the nucleotide structure may be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, eDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

The terms "target polynucleotide" and "target nucleic acid," as used herein, refer to a nucleic acid or polynucleotide which is targeted by a nucleic acid editing moiety present disclosure. For example, the "target nucleic acid," may be targeted by a nucleic acid integration moiety comprising a nucleic acid cleavage moiety as described herein. A target nucleic acid can be DNA. A target nucleic acid can be RNA. A target nucleic acid may refer to a chromosomal sequence or an extrachromosomal sequence (e.g., an episomal sequence, a minicircle sequence, a mitochondrial sequence, a chloroplast sequence, etc.). A target nucleic acid may be a nucleic acid sequence that may not be related to any other sequence in a nucleic acid sample by a single nucleotide substitution. A target nucleic acid may be a nucleic acid sequence that may not be related to any other sequence in a nucleic acid sample by a 2, 3, 4, 5, 6, 7, 8, 9, or 10 nucleotide substitutions. In some embodiments, the substitution may not occur within 5, 10, 15, 20, 25, 30, or 35 nucleotides of the 5' end of a target nucleic acid. In some embodiments, the substitution may not occur within 5, 10, 15, 20, 25, 30, 35 nucleotides of the 3' end of a target nucleic acid. In general, the term "target sequence" refers to a nucleic acid sequence on a single strand of a target nucleic acid. The target sequence may be a portion of a gene, a regulatory sequence, genomic DNA, cell free nucleic acid including cfDNA and/or cfRNA, cDNA, a fusion gene, and RNA including mRNA, miRNA, rRNA, and others.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and may include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene may refer to an "endogenous gene" or a native gene in its natural location in the genome of an organism. A gene may refer to an "exogenous gene" or a non-native gene. A non-native gene may refer to a gene not normally found in the host organism, but which is introduced into the host organism by gene transfer. A non-native gene may also refer to a gene not in its natural location in the genome of an organism. A non-native gene may also refer to a naturally occurring nucleic acid or polypeptide sequence that comprises mutations, insertions and/or deletions (e.g., non-native sequence).

The term genome editing, as used herein refers to altering one or more nucleotides within the genome of a cell. The cell may be in vivo. The cell may be ex vivo or in vitro. Non-limiting examples of genome editing methods include CRISPR-mediated genetic modification polypeptides such as Cas9, Cas12a (Cpf1), or other CRISPR endonucleases, Argonaute endonucleases, transcription activator-like (TAL) effector and nucleases (TALEN), zinc finger nucleases (ZFN), expression vectors, transposon systems (e.g., PiggyBac transposase), or any combination thereof. Designer zinc fingers, transcription activator-like effectors (TALEs), or homing meganucleases are available for producing targeted genome perturbations.

Targeted genome editing is possible via CRISPR-mediated genetic modification using a Cas or Cas-like endonuclease. CRISPR (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli*, and associated genes.

The term "transgene" refers to any nucleic acid molecule that is introduced into a cell. The resultant cell after receiving a transgene is referred to a transgenic cell. A transgene may include a gene that is partly or entirely heterologous (i.e., foreign) to the transgenic organism or cell, or may represent a gene homologous to an endogenous gene of the organism or cell. In some cases, transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). In some embodiments, the transgene or a foreign polynucleotide may be introduced into a cell for stable incorporation within the genome by a site specific recombination process. The term "recombination" or "DNA recombination," as used interchangeably herein, generally refers to a process by which nucleic acid fragments from two different polynucleotide sequences are exchanged. Recombination may involve breakage and exchange of DNA segments between two strands of DNA. Recombination may be regulated by a recombination moiety, e.g., a small molecule or a polypeptide such as an enzyme. In an example, the recombination may be regulated by at least 1, 2, 3, 4, 5 or more enzymes. The recombination may be regulated by at most 5, 4, 3, 2, or 1 enzyme. One or more enzymes that perform or facilitate DNA recombination may be a single, or multiple enzymes performing the steps of creating the breaks (excision), bringing the exchange strand in proximity to the breakage sites and removing the pre-existing strand, and sealing the broken ends or ligation. The one or more enzymes may comprise, for example, one or more of endonucleases for creating the breaks; and one or more ligases, for ligation. DNA recombination may be performed by recombinases. The terms "sequence-specific recombination" and "site-specific recombination," as used interchangeably herein, refer to a function performed by a recombination moiety (e.g., enzymes), for example, recombinases that recognize and bind to a short nucleic acid site or "sequence-specific recombinase target site", i.e., a recombinase recognition site, and catalyze the recombination of nucleic acid in relation to these sites. These enzymes may include recombinases, transposases and integrases. The terms "sequence-specific recombinase target site", "site-specific recombinase target site", "sequence-specific target site" and "site-specific target site" refer to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites. The Cre/lox system is frequently used in sequence specific recombination of DNA. The Cre recombinase is a regulator of the Cre/lox system that catalyzes site-specific recombination by crossover between two distant Cre recognition sequences, i.e., loxP sites. The loxP site refers to a nucleotide sequence at which the product of the cre gene of bacteriophage P1, the Cre recombinase, can catalyze a site-specific recombination event. The loxP sites include two 13-bp inverted repeats separated by an 8-bp spacer sequence. Any DNA sequence introduced between the two 34-bp loxP sequences (termed "foxed" DNA) is excised because of Cre-mediated recombination. The presence of the Cre recombinase is necessary for the exchange of the first and the second polynucleotide sequences.

Transposons, or transposable elements (TEs), are genetic elements that have the capability to transpose genetic material into the genome by use of an enzyme known as transposase. Mammalian genomes contain a high number of transposable element (TE)-derived sequences, and up to 70% of our genome represents TE-derived sequences (de Koning et al. 2011; Richardson et al. 2015). These elements could be exploited to introduce genetic material into the genome of a cell. The TE elements are capable of mobilization, often termed as "jumping" genetic material within the genome. TEs generally exist in eukaryotic genomes in a reversibly inactive, epigenetically silenced form.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "expression" refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. "Up-regulated," with reference to expression, refers to an increased expression level of a polynucleotide (e.g., RNA such as mRNA) and/or polypeptide sequence relative to its expression level in a wild-type state while "down-regulated" refers to a decreased expression level of a polynucleotide (e.g., RNA such as mRNA) and/or polypeptide sequence relative to its expression in a wild-type state. Expression of a transfected gene may occur transiently or stably in a cell. During "transient expression" the transfected gene is not transferred to the daughter cell during cell division. Since its expression is restricted to the transfected cell, expression of the gene is lost over time. In contrast, stable expression of a transfected gene may occur when the gene is co-transfected with another gene that confers a selection advantage to the transfected cell. Such a selection advantage may be a resistance towards a certain toxin that is presented to the cell. Where a transfected gene is required to be expressed, the application envisages the use of codon-optimized sequences. An example of a codon optimized sequence may be a sequence optimized for expression in a eukaryote, e.g., humans (i.e. being optimized for expression in humans), or for another eukaryote, animal or mammal. Codon optimization for a host species other than human, or for codon optimization for specific organs is known. In some embodiments, the coding sequence encoding a protein may be codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. Codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell may generally be a reflection of the codons used most frequently in peptide synthesis. Accordingly, genes may be tailored for optimal gene expression in a given organism based on codon optimization. Codon usage tables are readily available, for example, at the "Codon Usage Database" available at www.kazusa.orjp/codon/ and these tables may be adapted in a number of ways. Computer algorithms for codon optimizing a particular sequence for expression in a particular host cell are also available, such as Gene Forge (Aptagen; Jacobus, Pa.), are also available.

The term "expression cassette," "expression construct," or "expression vector" refers to a nucleic acid that includes a nucleotide sequence such as a coding sequence and a template sequence, and sequences necessary for expression of the coding sequence. The expression cassette may be viral or non-viral. For instance, an expression cassette includes a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

A "plasmid," as used herein, refers to a non-viral expression vector, e.g., a nucleic acid molecule that encodes for genes and/or regulatory elements necessary for the expression of genes. A "viral vector," as used herein, refers to a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

The term "promoter," as used herein, refers to a polynucleotide sequence capable of driving transcription of a coding sequence in a cell. Thus, promoters used in the polynucleotide constructs of the disclosure include cis-acting transcriptional control elements and regulatory sequences that are involved in regulating or modulating the timing and/or rate of transcription of a gene. For example, a promoter may be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions, developmental conditions, or drug or chemical conditions. Exemplary inducible promoter may be a doxycycline or a tetracycline inducible promoter. Tetracycline regulated promoters may be both tetracycline inducible or tetracycline repressible, called the tet-on and tet-off systems. The tet regulated systems rely on two components, i.e., a tetracycline-controlled regulator (also referred to as transactivator) (tTA or rtTA) and a tTA/rtTA-dependent promoter that controls expression of a downstream cDNA, in a tetracycline-dependent manner. tTA is a fusion protein containing the repressor of the Tn10 tetracycline-resistance operon of *Escherichia coli* and a carboxyl-terminal portion of protein 16 of herpes simplex virus (VP16). The tTA-dependent promoter consists of a minimal RNA polymerase II promoter fused to tet operator (tetO) sequences (an array of seven cognate operator sequences). This fusion converts the tet repressor into a strong transcriptional activator in eukaryotic cells. In the absence of tetracycline or its derivatives (such as doxycycline), tTA binds to the tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. In contrast, in the tet-ON system, a mutant form of tTA, termed rtTA, has been isolated using random mutagenesis. In contrast to tTA, rtTA is not functional in the absence of doxycycline but requires the presence of the ligand for transactivation.

The term "pharmaceutically acceptable" refers to approved or approvable by a regulatory agency of the Federal or a state government or listed in the U.S. Pharmacopeia or other generally recognized pharmacopeia for use in animals, including humans. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent. A "pharmaceutically acceptable salt" of pooled disease specific antigens as recited herein can be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluene sulfonic, methane sulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled disease specific antigens provided herein, including those listed by Remington's Pharmaceutical Sciences, 17th ed., Mack Publishing Company, Easton, Pa., p. 1418 (1985).

In some cases, manipulating a cell with an exogenous agent, may refer to incorporating a heterologous gene or nucleic acid into the cell. In some cases, manipulating may refer to adding an agent, such as a peptide or a small molecule to activate the cell.

"Substantially" as used herein may refer to "considerably" or "completely," and may be set in a quantifiable context only relative to a known, a comparable or an expected outcome. For example, a sample substantially less T cell may refer to the sample as comprising less than 20%, relative to a compared sample that comprises 80% or more T cells. "Substantially devoid of" in a similar context may be less than 10% or less than 5% or about 0% T cells.

The terms "treat," "treated," "treating," "treatment," and the like are meant to refer to reducing, preventing, or ameliorating a disorder and/or symptoms associated therewith (e.g., a neoplasia or tumor or infectious agent or an autoimmune disease). "Treating" can refer to administration of the therapy to a subject after the onset, or suspected onset, of a disease (e.g., cancer or infection by an infectious agent or an autoimmune disease). "Treating" includes the concepts of "alleviating", which refers to lessening the frequency of occurrence or recurrence, or the severity, of any symptoms or other ill effects related to the disease and/or the side effects associated with therapy. The term "treating" also encompasses the concept of "managing" which refers to reducing the severity of a disease or disorder in a patient, e.g., extending the life or prolonging the survivability of a patient with the disease, or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "prevent", "preventing", "prevention" and their grammatical equivalents as used herein, means avoiding or delaying the onset of symptoms associated with a disease or condition in a subject that has not developed such symptoms at the time the administering of an agent or compound commences.

The term "therapeutic effect" refers to some extent of relief of one or more of the symptoms of a disorder (e.g., a neoplasia, tumor, or infection by an infectious agent or an autoimmune disease) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required.

While cancer is one exemplary embodiment described in exclusive detail in the instant disclosure, the methods and technologies described herein are contemplated to be useful in targeting an infected or otherwise diseased cell inside the body. Similarly, therapeutic and vaccine compositions using the engineered cells are described herein.

Myeloid Cells for Immunotherapy

In one aspect, the instant application focuses on a subset of myeloid cell that can be used for effective immunotherapy, for example, for effective vaccination. Provided herein is a method of isolating, selecting, enriching, and validating by functional assay a subset of myeloid cell that can be used for effective immunotherapy. In one aspect, a method is provided herein for identification and isolation of a subset of myeloid cells that can be further modified suitably for generating effector myeloid cells.

Myeloid cells currently used extensively in immunotherapy are antigen presenting dendritic cells, or activated mature macrophages. Antigen presenting DCs or activated macrophages often fail to be therapeutically effective for in vivo transfer as the cells are terminal, have reached their propagation limit and fail to divide further, have short life span, are exhausted, are poorly excitable in circulation in vivo. In some instances, such cells poorly express any transgenes when operating within a tissue environment or they may lose transgene expression altogether. In some instances, DCs or activated macrophages may show poor migration, and cannot access the lymph nodes and therefore are less effective in activating the adaptive immune sequelae that can be triggered by activating naïve T cells in the lymph node.

On the other hand, effective immunotherapy requires that the cells, preferably myeloid cells for the subject of the application, should be pliable, can be engineered, e.g., express a transgene in the cell, without compromising plasticity, may not exhibit tonic signaling, and can be activated only in a tissue microenvironment, may exhibit effective migration in vivo and can access the lymph nodes and activate lymphocyte to generate an active adaptive immune response.

For the above, it is important to identify the correct population of cells to further manipulate and generate a myeloid cell that can be used for effective immunotherapy.

In some embodiments, the myeloid cell is a progenitor cell.

In some embodiments, the myeloid cell is not transformed or activated prior to administering to a subject in need thereof.

In some embodiments, the myeloid does not exhibit tonic signaling at the time of administering to the subject. In some embodiments, the cells can differentiate into effector cells; and infiltrate into a diseased site of the subject after administration or migrate to a diseased site of the subject after administration; or have a life-span of at least 5 days in the subject after administration.

In some embodiments, the myeloid cell exhibits low phagocytosis prior to administering to a subject, or prior to activating ex vivo by an external stimulus, such as, with a cytokine, or a growth factor, or in presence of a target for phagocytosis. In some embodiments, the myeloid cell exhibits moderate phagocytosis prior to administering to a subject, or prior to activating ex vivo by an external stimulus, such as, with a cytokine, or a growth factor, or in presence of a target for phagocytosis. In some embodiments, the myeloid cell exhibits responsiveness to any one or more of: GMCSF, GCSF, IL-4, IL-1b, IL-6, TNF, CCL2, CCL5, CXCL1 or a combination thereof.

In some embodiments, the myeloid cell exhibits enhanced phagocytosis upon being activated ex vivo by an external stimulus, such as, with a cytokine, or a growth factor, or in presence of a target for phagocytosis. In some embodiments, the myeloid cell exhibits about 1.1 fold, 1.2 fold, 1.5 fold, 1.7 fold, 2 fold, 3 fold, 4 fold, 5 fold, 6 fold, 7 fold, 8 fold, 9 fold, 10 fold, 11 fold, 12 fold, 13 fold, 14 fold, 14 fold, 17 fold, 20 fold or more enhanced phagocytosis upon activating ex vivo by an external stimulus, such as, with a cytokine, or a growth factor, or in presence of a target for phagocytosis, compared to an activated terminally differentiated myeloid cell such as mature post activation macrophage. In some embodiments, the myeloid cell exhibits responsiveness to cytokines or chemokines, exemplified by any one or more of: GMCSF, GCSF, IL-4, IL-1b, IL-6, TNF, CCL2, CCL5, CXCL1 or a combination thereof.

In some embodiments, the myeloid cell can be manipulated ex vivo. Manipulating ex vivo may include but is not limited to: genetically engineering of a myeloid cell, expressing a transgene in a myeloid cell, contacting a myeloid cell with a nucleic acid, contacting a myeloid cell with a chemical or a small molecule, activating a myeloid cell with a cytokine, a growth factor, a chemokine, a tactile stimulus, a thermal stimulus or a combination thereof.

In some embodiments, the myeloid cell exhibits a longer life span after manipulating ex vivo, in comparison to that of an pre-activated and pre-differentiated myeloid cell, for example a mature macrophage cell under similar circumstances, which may be, for example, at least longer than 24 hours, longer than 48 hours, longer than 50 hours, longer than 55 hours, longer than 60 hours, longer than 70 hours, longer than 80 hours, longer than 90 hours, longer than 100 hours, longer than 110 hours, longer than 120 hours, longer than 130 hours, longer than 140 hours, longer than 150 hours, longer than 160 hours, longer than 170 hours, longer than 180 hours, longer than 190 hours, longer than 200 hours, longer than 210 hours, longer than 220 hours, longer than 230 hours, longer than 240 hours, longer than 250 hours, longer than 300 hours, longer than 350 longer than 400 hours, longer than 500 hours, longer than 1000 hours.

In some embodiments, the myeloid cell exhibits cytological plasticity prior to administering to a subject in need thereof. In some embodiments, the myeloid cell is not spontaneously transformed into an activated and/or matured cell, or is not altered in morphology or physiology, or does not exhibit advanced aging prior to administering into a subject in need thereof. In some embodiments the myeloid cell may be capable of cell division.

In some embodiments, the myeloid cell is a primary cell.

In some embodiments, the myeloid cell is a transformed cell, which is transformed ex vivo.

In some embodiments, the myeloid cell is not a stem cell.

In some embodiments, the myeloid cell can be engineered ex vivo.

In some embodiments, the myeloid cell exhibits higher chemotaxis in response to a chemotaxis stimulus, for example a chemotactic agent, a chemokine compared to an activated macrophage, as determine by a chemotaxis assay. In some embodiments, the myeloid cell exhibits at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold or at least 10 fold, at least 15 fold, at least 20 fold, at least 30 fold, at least 40 fold, at least 50 fold higher chemotaxis in response to a chemotaxis stimulus, for example a chemotactic agent, a chemokine compared to an activated terminally differentiated myeloid cell, such as an activated macrophage, as determine by a chemotaxis assay.

In some embodiments, the myeloid cell is isolated from a human subject, such as a donor.

In some embodiments, the myeloid cell is enriched to raise the proportion of the myeloid cell within a population of cells.

In some embodiments, the myeloid cell is autologous.

In some embodiments, the myeloid cell is allogeneic.

In one aspect, provided herein is a population of cells isolated from a human peripheral blood, that is further enriched for myeloid cells suitable for generation of therapeutically effective myeloid cells, wherein the population of cells comprise less than 5% CD3+ cells. In some embodiments, the enriched population of myeloid cells comprise less than 4% CD3+ cells. In some embodiments, the enriched population of myeloid cells comprise less than 3% CD3+ cells. In some embodiments, the enriched population of myeloid cells comprise less than 5% CD19+ cells. In some embodiments, the enriched population of myeloid cells comprise less than 4% CD19+ cells. In some embodiments, the enriched population of myeloid cells comprise less than 3% CD19+ cells. In some embodiments, the enriched population of myeloid cells comprise less than 5% CD56+ cells. In some embodiments, the enriched population of myeloid cells comprise less than 4% CD56+ cells. In some embodiments, the enriched population of myeloid cells comprise less than 3% CD56+ cells.

In some embodiments, the myeloid cell is enriched, and modified ex vivo to generate therapeutically effective myeloid cells. Modifying a myeloid cell ex vivo as used herein can mean manipulating the cell ex vivo. Manipulating ex vivo as used herein may include but is not limited to: genetically engineering of a myeloid cell, expressing a transgene in a myeloid cell, contacting a myeloid cell with a nucleic acid, contacting a myeloid cell with a chemical or a small molecule, activating a myeloid cell with a cytokine, a growth factor, a chemokine, a tactile stimulus, a thermal stimulus or a combination thereof.

In some embodiments, the myeloid cell is manipulated for generating a therapeutic for cancer. In some embodiments, the myeloid cell is manipulated for generating a cancer vaccine. In some embodiments, the myeloid cell is manipulated for generating a therapeutic for an infectious disease, such as a viral, bacterial, fungal, plasmodial or parasitic infection. In some embodiments, the myeloid cell is manipulated for generating a therapeutic for tuberculosis. In some embodiments, the myeloid cell is manipulated for generating a therapeutic for an inflammatory disease. In some embodiments, the myeloid cell is manipulated for generating a therapeutic for an autoimmune disease.

CD14+ CD16− Monocyte Key "Progenitor" Cell

Early monocytes or monocyte progenitor cell have not been well-investigated for their potential in cell therapy. Monocytes make up a large proportion of circulating blood population, as well as by far the most abundant cell in an immunologically active site in a tissue, including a tumor. These cells migrate into almost all pathologic tissues and can differentiate into any number of downstream myeloid effector cells. By harnessing these cells and combining them with engineering these myeloid cells can be designed for effective cell therapy tools with wide-spread application as therapeutic in cancer, neurodegeneration, cardiological and infectious diseases, to name a few.

A candidate for a therapeutically effective myeloid cells may be a progenitor cell that have the potential for a longer life span compared to mature myeloid cells, e.g. macrophages; they have the potential to mature or differentiate into myeloid lineages such as macrophages, or dendritic cell lineages, have the potential to be stimulated by a large variety of stimuli, have the potential to migrate readily to an immunologically active tissue location and can activate the adaptive tissue system. Myeloid progenitor cells described in the application may not refer to myeloid progenitor stem cells. The methods described in the disclosure do not correspond to a stem cell mobilization process.

The present application is based at least in part on the finding that phenotype of the myeloid cells of therapeutic interest as described herein may be a monocytic progenitor lineage, especially, that have plasticity to differentiate into monocyte, dendritic cells, or polarize into M0, M1 or M2 macrophage subtypes. In one aspect, such a cell may be CD14+. In one aspect, such a cell may be CD16−. In some embodiments, a therapeutically effective myeloid cell lineage may express high levels of CD14(CD14$^{hi}$, or CD14 high), and express low levels of CD16, or do not express detectable CD16. In one embodiment, the myeloid cells of therapeutic interest as described herein may express high levels of CCR2 and/or CCR5, and/or chemokines for migration to a diseased site in a subject. In one embodiment, the cells express low levels of CD206, CD163, CD80, CD86, and/or CD63.

In one embodiment, the myeloid cells may be phenotypically distinguishable from mature macrophage cells in that the cells are more spherical than a mature macrophage cell, lacks pseudopodia and may express or can be induced to express high levels of chemokines and cytokines and can actively migrate to immunologically active tissue location. In one embodiment, the myeloid cells of the disclosure may be antigen naïve.

Myeloid cells of high therapeutic potential as described herein may be normally present in the peripheral blood at a level greater than 20% of total peripheral blood mononuclear cells (PMBC) in a healthy human.

Little is yet known about isolating and using this specific cell for clinical purposes. In some cases, related to dendritic cell (DC) therapy, DCs can be generated in vitro from isolated monocytes by a process which involves culturing the monocytes and stimulating the cells ex vivo for at least a week for generating effective cells that are ready for infusion into a subject. Such a process requires not less than about 10 days from the time of isolation of the cells (or thawing from frozen state) to the point of administration. In one aspect, provided herein is a method of preparing myeloid cells by isolating the cells from a biological sample of a subject, manipulating the cell with an exogenous agent and be able to administer to the subject in need thereof, wherein the method may be completed within 3 days (FIG. 1). In some embodiments, manipulating the cell can be performed by activating the cell with antigens or peptides to generate antigen presenting cells. In some embodiments, manipulating may including activating the cell with one or more therapeutic agent. In some embodiments, manipulating may refer to genetic manipulation or incorporation of a heterologous nucleic acid.

In some embodiments, the method may be completed in 72 hours or less, 70 hours or less, 65 hours or less, 60 hours or less, 55 hours or less, 50 hours or less, 45 hours or less, 40 hours or less, or 35 hours or less.

In some embodiments, the myeloid cells are manipulated by incorporating a heterologous nucleic acid in vitro. In some embodiments, the cells are cultured briefly after manipulation. In some embodiments, the manipulation is such that the manipulation does not alter the plasticity of the cell. The manipulated cells retain high CD14 expression, The manipulated cells do not express CD16 at a higher level. The manipulated cells express CCR2 and or CCR5 in presence of a stimulus. In some embodiments the manipulated cell may be cultured for less than 48 hours (h), or less than 36 h, or less than 24 h or less than 20, 18, 16, 14 12, 10, 8, 6 or less than 4 h. In some embodiments, the cells may be obtained as frozen and thawed at one or more occasions prior to or after manipulation or both. In some embodiments, the freezing and thawing is done with caution such that the processes do not alter the plasticity of the cell.

Figure 2:
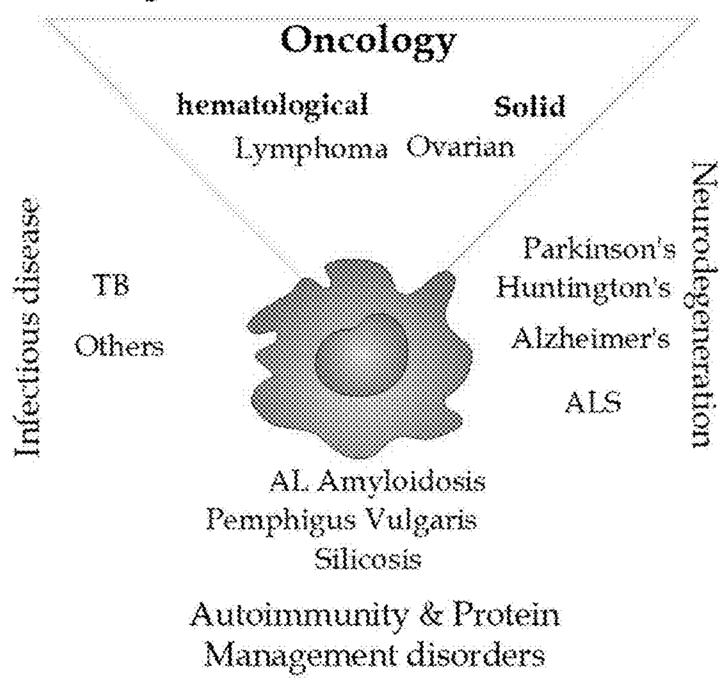
FIG. 2 depicts a schematic diagram showing exemplary applications of the myeloid effector cells described herein.

In one aspect, the myeloid cells of therapeutic interest as described herein have high plasticity to be effectively used as therapeutic cells in cell therapy in neurodegenerative diseases. Isolated CD14+/CD16− myeloid cells may be used to express chimeric antigen receptors (e.g. having an scFv) that can bind to and remove amyloid beta cells from neurodegenerative plaques and promote amyloid clearance as a therapeutic strategy for Alzheimer's disease. In another aspect, such cells may be manipulated to express anti-VEGF antibody; or be used to generate better vaccines and sentinel cells against pathogenic infection (FIG. 2).

Figure 3:
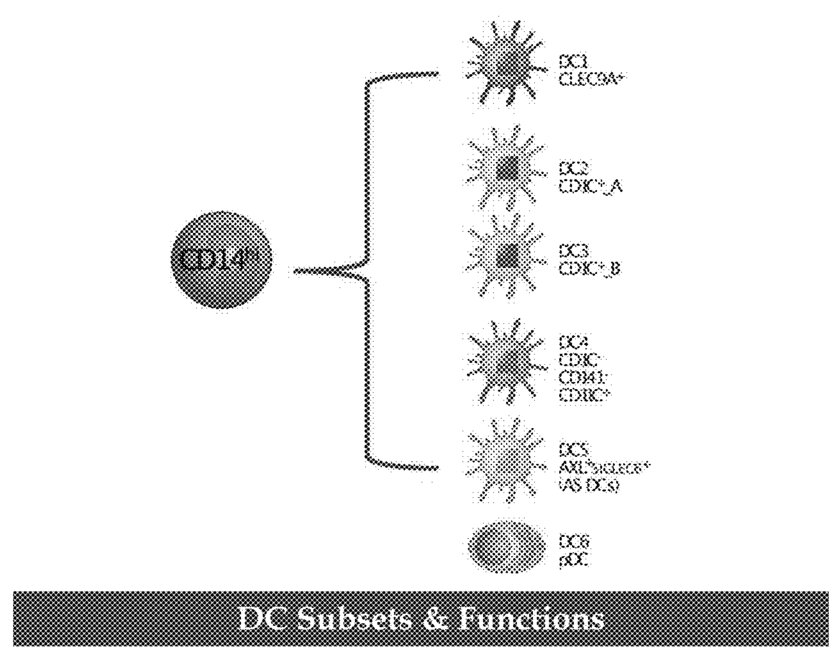
FIG. 3 is a diagrammatic representation of differentiation potential of cells expressing high levels of CD14 ($CD14^{hi}$ cells).

In one aspect, the myeloid cells of therapeutic interest is characterized by high level of plasticity and can differentiate or be stimulated to differentiate into a number of cellular subtypes that are highly effective in immune response when the cells encounter a suitable stimulus in vivo. For example, as shown in FIG. 3, a CD14 expressing myeloid cell as described herein may be suitably differentiated into multiple dendritic cell subtype at the site of a tissue inflammation or immune response. In an embodiment, the myeloid cells of therapeutic interest can be activated, differentiated and/or polarized to generate the effector cells in vivo, for example, can migrate to the site of infection or inflammation when administered systemically, can infiltrate an immunologically active site, or, for example a tumor and can effectively perform immunological function at the immunologically active site, for example, at the site of a tumor microenvironment.

In one aspect, the methods provided herein are scalable, and can be used to manufacture myeloid cells that are therapeutically effective in a clinical scale. In some embodiments, CD14+/CD16− myeloid cells can be isolated and purified by negative selection and using commercially available columns, and processed at a clinical scale; as needed, manipulating the isolated cells, and preparing a therapeutically effective composition.

Myeloid Cells in Cancer Immunotherapy

In one aspect, provided herein are compositions and method to utilize myeloid cells of therapeutic interest as described herein in cancer immunotherapy. Myeloid effector cells may be generated from the isolated myeloid cells of therapeutic interest using methods that do not alter the plasticity of these cells. Monocytic lineage cells are phagocytic and are efficient antigen presenter cells. Phagocytes are the natural sentinels of the immune system and form the first line of defense in the body. They engulf a pathogen, a pathogen infected cell a foreign body or a cancerous cell and remove it from the body. Most potential pathogens are rapidly neutralized by this system before they can cause, for example, a noticeable infection. This can involve receptor-mediated uptake through the clathrin coated pit system, pinocytosis, particularly macropinocytosis as a consequence of membrane ruffling and phagocytosis. The phagocytes therefore can be activated by a variety of non-self (and self) elements and exhibit a level of plasticity in recognition of their “targets”. Most phagocytes express scavenger receptors on their surface which are pattern recognition molecules and can bind to a wide range of foreign particles as well as dead cell, debris and unwanted particles within the body. In one aspect, recombinant nucleic acids encoding chimeric antigen receptors (CAR) may be expressed in the cells. The CARs may be variously designed to attack specific tumor cells, and myeloid effector cells expressing CARs can be activated to phagocytose and kill tumor cells. The CARs may be designed to generate phagocytic receptors that are activated specifically in response to the target engagement, and the phagocytic potential of a macrophage is enhanced by specifically engineered intracellular domains of the receptor. In addition, CAR-expressing myeloid effector cells can migrate to lymph nodes and cross-present antigens to naïve T cells in the lymph node thereby activating the adaptive response.

In one embodiment the recombinant nucleic acid used to manipulate a myeloid cell is an mRNA. In some embodiments the mRNA is reverse transcribed and purified. In some embodiments, the mRNA is incorporated into the cell by electroporation. In some embodiments, the mRNA is designed to have a long half-life. In some embodiments the mRNA comprises a long poly A tail. In some embodiments, the mRNA 3'UTR comprises a region from the beta globin mRNA 3'-UTR.

In some embodiment, the recombinant nucleic acid is a circRNA.

In some embodiments the mRNA encoding a recombinant nucleic acid comprises a retrotransposon sequence. In some embodiments, a nucleic acid sequence encoding a recombinant CAR is placed within a retrotransposon element. In some embodiments, the retrotransposon comprises an Alu element.

In some embodiment the method provided herein comprises stably integrating a transgene into the genome of a cell, the method comprising: introducing into a cell an mRNA comprising: (a) a sequence encoding a transgene; (b) a 5' UTR nucleic acid sequence and a 3' UTR nucleic acid sequence flanking the sequence encoding the transgene; wherein the 5' UTR nucleic acid sequence or the 3' UTR nucleic acid sequence comprises one or more of: (i) an endonuclease binding site, (ii) a reverse transcriptase binding site, (iii) a ribosome binding site, (iv) a retrotransposase binding site, and (v) a poly A sequence; wherein the sequence encoding the transgene is in a sense or antisense directionality, and wherein the transgene is stably incorporated into the genome of the cell. In some embodiments, the method further comprising introducing into the cells a sequence encoding an endonuclease and/or a reverse transcriptase. In some embodiments, the mRNA comprises a sequence encoding an endonuclease and/or a reverse transcriptase.

In some embodiments, the endonuclease and/or a reverse transcriptase is ORF2p.

In some embodiments, the retrotransposase is an L1 ORF protein. In some embodiments, the retrotransposase is an L1 ORF2p protein. In some embodiments, the retrotransposase is an L1 ORF1p protein. In some embodiments, the poly A sequence is a genomic DNA priming sequence. In some embodiments, the poly A sequence is a target-site primer for reverse transcription.

In some embodiments, the genomic DNA priming sequence comprises at least one, at least two, at least three, at least four or at least five nucleotides adjacent to the poly A sequence. In some embodiments, the at least one, at least two, at least three, at least four or at least five nucleotides adjacent to the poly A sequence forms a target-site primer for reverse transcription. In some embodiments, the genomic DNA priming sequence comprises specific genome targetable sequence. In some embodiments, the 5' UTR or a 3' UTR comprises a SINE sequence. In some embodiments, the 5' UTR comprises a comprises an Alu sequence. In some embodiments, the 3' UTR comprises an Alu sequence. In some embodiments, the 5' UTR comprises an L1 sequence. In some embodiments, the 3' UTR comprises an L1 sequence. In some embodiments, the transgene is retrotransposed into the genomic DNA. In some embodiments, the transgene is retrotransposed in trans. In some embodiments, the transgene is retrotransposed in cis. In some embodiments, the transgene is retrotransposed at a specific genomic locus. In some embodiments, the method further comprises one or more stop codons adjacent to the 3'end of the transgene. In some embodiments, the one or more stop codons adjacent to the 3'end of the transgene, operably linked to the transgene. In some embodiments, the one or more stop codons adjacent to the 3'end of the transgene is arranged in tandem. In some embodiments, the one or more stop codons adjacent to the 3'end of the transgene is arranged in separate reading frames. In some embodiments, the method further comprises introducing to the myeloid cell a nucleic acid encoding L1-ORF2.

In some embodiments, the recombinant CAR comprises an extracellular domain comprising an antigen binding domain comprises a receptor domain, antibody domain, wherein the antibody domain comprises a functional antibody fragment, a single chain variable fragment (scFv), a Fab, a single-domain antibody (sdAb), a nanobody, a $V_H$ domain, a $V_L$ domain, a VNAR domain, a VHH domain, a bispecific antibody, a diabody, or a functional fragment or a combination thereof.

In some embodiments, the antigen is selected from the group consisting of Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), Mesothelin, EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin receptor, PRSS21, VEGFR2, PDGFR-beta, SSEA-4, EGFR, NCAM, prostase, PAP, ELF2M, GM3, TEM7R, CLDN6, TSHR, GPRC5D, ALK, IGLL1 and combinations thereof. In some embodiments, the phagocytic or tethering receptor further comprises an intracellular domain comprising an intracellular signaling domain. the transmembrane domain is operably linked to the intracellular domain. In some embodiments, the transmembrane domain is functionally linked to the intracellular domain via dimerization or oligomerization. In some embodiments, the transmembrane domain dimerizes with an Fc receptor transmembrane domain. In some embodiments, the transmembrane domain is an FcR domain, selected from a group consisting of FcR-alpha, FcR-beta and FcR-gamma transmembrane domain. In some embodiments, the transmembrane domain comprises a domain selected from a group consisting of, T Cell Receptor subunit, CD3 epsilon, CD3 gamma and CD3 delta, CD45, CD2 CD4, CD5, CD8, CD9, CD16, CD19, CD22, CD33, CD28, CD30, CD37, CD64, CD80, CD86, CD134, CD137 and CD 154 transmembrane domain, or a functional fragment thereof, or an amino acid sequence having at least one, two or three modifications but not more than 20, 10 or 5 modifications from any of the above. In some embodiments, the intracellular signaling domain is derived from a phagocytic receptor selected from the group consisting of lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CR3, CR4, Tim-1, Tim-4 and CD169. In some embodiments, the intracellular signaling domain comprises a phagocytosis enhancement domain. In some embodiments, the intracellular signaling domain comprises a PI3K recruitment domain.

In some embodiments the method described herein comprises introducing to the myeloid cell a nucleic acid encoding a chimeric antigen receptor protein, and one or more additional nucleic acids encoding one or more additional proteins or peptides. For example, the method comprises introducing to the myeloid cell a nucleic acid encoding a CAR, and a second nucleic acid encoding a second protein or a peptide. For example, the method comprises introducing to the myeloid cell a nucleic acid encoding a CAR, and a second nucleic acid encoding a second protein or a second peptide; and a third nucleic acid encoding a third protein or a third peptides. In some embodiments one or more additional nucleic acids encoding one or more additional proteins or peptides may be further introduced into the myeloid cell to facilitate increase of CAR expression. In some embodiments, the one or more additional nucleic acids may encode a growth factor for the myeloid cell, or enhance a phagocytic function, or any other related function. In some embodiments, the one or more additional nucleic acids may encode a protein that positively regulates chemotaxis. In some embodiments, the one or more additional nucleic acids may encode a protein that enhances the expression of the transgene incorporated in the myeloid cell.

In one embodiment, the one or more additional nucleic acids comprise a nucleic acid that encodes a gap junction protein. In on embodiment, coexpression of the gap junction protein enhances the expression of the CAR transgene incorporated in the myeloid cell. Gap junctions are dynamic structures, consisting of hundreds to thousands of channels, made up of connexins, organized in quasi-crystalline arrays. These intercellular structures permit adjacent cells to engage in direct communication by allowing the passage of ions and small metabolite and also nucleic acids. In some embodiments, the one or more additional nucleic acid encodes an adhesion molecule. Cell adhesion molecules have the ability to allow cells to adhere to each other and to the extracellular matrix and also allows cells to interact and communicate with each other and their environment and, in doing so, regulates a range of cell functions, including proliferation, gene expression, differentiation, apoptosis, and migration. Exemplary adhesion molecules include but are not limited to members of the integrin family, selectins, cadherins, members belonging to the immunoglobulin superfamily, and members of the CD44 family. In some embodiments, a second nucleic acid sequence encoding, for example, an ICAM-1 is introduced into the myeloid cell, co-expressed with a CAR in the same cell. In some embodiments, a second nucleic acid sequence encoding a VCAM-1 is co-expressed, in the myeloid cell along with a CAR. In some embodiments the second nucleic acid encodes a selectin. In some embodiments the second nucleic acid encodes a selectin. In some embodiments the second nucleic acid encodes a CD49a/CD29, or a CD49b/CD29, or a CD49c/CD29, or a CD49d/CD29, or a CD49e/CD29, or a CD49f/CD29. In some embodiments, the second nucleic acid, and/or any additional nucleic acids encoding the second protein or peptide or the additional protein peptide is comprised in a vector, for example, an expression vector, wherein the expression vector has regulatory elements which can be designed for controlled expression, for example, expression controlled by a transcriptional “on-off” switch. Exemplary vectors with transcriptional on-off switch may include tetracycline regulated systems (Tet-on, Tet-off systems) known to one of skill in the art or can be easily conceived by a skilled artisan.

In some embodiments, the one or more additional nucleic acids, for example the second nucleic acids comprises a nucleic acid sequence that encodes a connexin. In some embodiments, the one or more additional nucleic acids comprise a nucleic acid that encodes connexin 43. In some embodiments, the nucleic acid encoding connexin 43 is packaged in an expression vector, the vector comprising a promoter, optionally an enhancer, a 5'-UTR, and 3'-UTR, a stabilizing moiety in the 3'UTR such as a BGH3' region, and poly A polynucleotides, operably linked to the nucleic acid region encoding the connexin. In some embodiments, connexin 43 is overexpressed in the cell. In some embodiments, the nucleic acid encoding the connexin is separate from the nucleic acid encoding the chimeric antigen receptor, CAR. In some embodiments, the nucleic acid encoding CAR is in a different vector that CAR. In some embodiments the CAR is delivered into the myeloid cell as naked nucleic acid, while the one or more nucleic acids comprising the one nucleic acid encoding the CAR is expressed in an expression vector. In some embodiments, the expression vector comprises a CMV promoter. In some embodiments, the embodiments connexin 43 is overexpressed. In some embodiments, the second nucleic acid, and/or any additional nucleic acids encoding the second protein or peptide or the additional protein peptide is comprised in a vector, for example, an expression vector, wherein the expression vector has regulatory elements which can be designed for controlled expression, for example, expression controlled by a transcriptional "on-off" switch. Exemplary vectors with transcriptional on-off switch may include tetracycline regulated systems (Tet-on, Tet-off systems) known to one of skill in the art or can be easily conceived by a skilled artisan.

In some embodiments, the CAR expressing cell may be further manipulated to reduce the expression of one or more endogenous genes. In some embodiments, the manipulation may comprise editing an endogenous gene at the genome level of the myeloid cell, either prior to following introducing the nucleic acid encoding a CAR. For example, a gene or a regulatory fragment thereof may be edited in the myeloid cell to enhance one or more functions of the myeloid cell. In some embodiments, an In some embodiments, a cell expressing the CAR exhibits an increase in production of a cytokine and chemokines compared to a cell not expressing the CAR. In some embodiments, wherein the cytokine is selected from the group consisting of IL-1, IL3, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon and combinations thereof.

In some embodiments, a cell expressing the CAR exhibits an increase in effector activity compared to a cell not expressing the CAR.

In some embodiments, a cell expressing the CAR exhibits an increase in resistance to CD47 mediated inhibition of phagocytosis compared to a cell not expressing the CAR.

In some embodiments, a cell expressing the CAR exhibits an increase in resistance to LILRB1 mediated inhibition of phagocytosis compared to a cell not expressing the CAR.

In some embodiments, the extracellular domain comprises an Ig binding domain.

Myeloid Cells for Infectious Disease Therapy

In one aspect, the myeloid cells described herein is used for developing therapeutically effective cells for treating infectious diseases. Myeloid cells can be a powerful tool in treating infections such as bacterial infections, viral infections, fungal infections, certain protozoal infections. In one embodiment, a myeloid cell isolated as described in the invention is further manipulated or modified to express a chimeric antigenic receptor (CAR) that has an extracellular antigen binding domain that can bind to an antigen on a pathogenic bacteria, and an intracellular domain that triggers and/or augments phagocytosis, and/or activates an inflammasome component within the myeloid cell.

In some embodiments CAR may be designed having an extracellular binding domain specific for a bacterial surface antigen, such as lipoarabinomannan (LAM), may be useful in phagocytosing *Mycobacterium tuberculosis*. Myeloid cells that effectively phagocytose a pathogen, such a *M. tuberculosis* can also present the antigen to lymphocytes and generate long term immune response and immune memory. CAR may be designed having an extracellular binding domain specific for an antigen from e.g. *S. pneumonia*, H influenza, or N meningitis that is operably linked to an intracellular signaling domain that upon activation augments phagocytosis by the myeloid cell.

In some embodiments, a CAR may comprise a binding domain directed against a virus, targeted against a viral antigen. In some embodiments the viral antigen is an influenza antigen, such as an HA (hemagglutinin) antigen (e.g., H1, H2, H3, H5,), a neuraminidase antigen (e.g. N1, N2, N3 and so on), or a matrix protein antigen (M1), ion channel protein (M2). A myeloid cell expressing the CAR directed against an exemplary antigen as described herein may be useful as a myeloid cell based vaccine against influenza.

In some embodiments, a CAR may comprise a binding domain directed against an HBV protein, and the myeloid cell expressing the CAR may be useful in the development of a myeloid cell based HBV vaccine. Exemplary HBV antigens include but not limited to M-HbsAg, S-HBsAg and L-HBsAg. In some embodiments, a CAR may comprise a binding domain directed against a capsid protein of HPV16 or HPV 18.

In some embodiments, a myeloid cell therapy expressing a CAR directed towards a pathogen can help orchestrate a strong B cell response in the host, while reducing the initial pathogen burden by phagocytosis and elimination.

In some embodiments, a myeloid cell therapy expressing a CAR directed towards a pathogen can help orchestrate a strong T cell response in the host, while reducing the initial pathogen burden by phagocytosis and elimination.

In one embodiment, a strong T cell response may be generated against a coronavirus, including but not limited to novel coronavirus-19 or nCOV-2, that causes the COVID pandemic. Contemplated herein is a myeloid cell expressing a CAR that is directed towards an nCOV-2 antigen such as an S protein antigen, a NSP protein antigen, an E protein antigen, an M protein antigen, an N protein antigen or a NSP antigen.

Method of Making Therapeutically Effective Myeloid Cells

Isolation and/or Enrichment of Myeloid Cells

Myeloid cells may be isolated from human peripheral blood. In some embodiments, myeloid cells may be isolated from a subject by direct draw of peripheral blood. In some embodiments, myeloid cells may be isolated from leukapheresis samples available in containers. In some embodiments, peripheral blood from healthy donors is used as a source of the myeloid cells. In some embodiments, PBMCs are isolated from a healthy donor's blood sample.

In some embodiments, the PBMC are isolated in a aseptic, closed system.

In some embodiments, PBMCs may be contacted with an antibody that binds to a cell surface molecule on a monocyte or a monocyte progenitor cell, and the antibody is used to isolate the cell of interest. In some embodiments, the PBMC cells are contacted with antibody coated beads which bind to specific cells within the PBMC, cells that express the specific cell surface markers to which the antibodies bind to. In some embodiments, the antigen may be immobilized, for example, adhered to the surface of a container, or a column, or may be attached on a bead, which when passed through a PBMC cell suspension, captures the cell expressing the cell surface molecule that the antibody binds to. This method is referred to a positive selection method. In some embodiments, the PBMC are contacted with an anti-CD14 antibody or anti-CD14 antibody coated beads. In some embodiments, one or more of the following antibodies are used for positive selection, which may bind to one or more of the surface markers that are expressed on a myeloid cell of interest as described herein, but such markers are not limited to the list, consisting of: CD64, CD192 (CCR2), CD195 (CCR5), CD120a (TNFR1) and CD120b (TNFR2). In some embodiments, any antibodies as used herein may be complete antibodies or functional fragments thereof, Fab', recombinant antibodies, engineered antibodies, scFv, diabodies, triabodies or other engineered capture molecules. In some embodiments, antibodies may be engineered that do not activate one or more cell surface molecules upon binding and/or does not lead to tonic signaling in the myeloid cell.

Cells bound to antibody coated beads may be separated by means of density gradient centrifugation; by magnetic separation (where the beads are magnetic beads); or by any other suitable means, for example using beads that are pre-immobilized on a surface, and passing the PBMCs over the bed of immobilized beads as a mobile phase. Following separation of unbound cells from the bead-bound cells, and washing with suitable buffer, the cells are eluted from the beads by a suitable method, for example by uncoupling the ligand-antibody binding by using a suitable buffer, or using a peptidase or any other suitable enzymes or compounds that uncouples the bond between the cell to the antibody coated bead. The cells are recovered for further analysis.

In some embodiments, PBMCs may be contacted with an antibody that binds to a cell surface molecule that is expressed on a cell that is not a monocyte or a monocyte progenitor cell, and the antibody is used to remove undesired cells from the PBMC, and isolate the leftover cell of interest. This is termed a negative selection method. In some embodiments, this method may be preferred for example, in consideration of the fact that monocytes may become activated upon contact with a cell surface binding molecule, such as an antibody. Premature activation can be avoided by negative selection. In some embodiments, the negative selection in the context of the invention may be achieved by removing one or more of lymphocytes, NK cells, dendritic cells, mature macrophages, and/or exhausted phagocytes. In some embodiments, the method encompasses selective depletion of one or more of lymphocytes, NK cells, dendritic cells, mature macrophages, and/or exhausted phagocytes from any biological sample such that the remaining cells that are finally harvested are monocytes or progenitor monocytic cells as described herein. In some embodiments, one or more antibodies are suitably used to remove said cells listed above may include, but are not limited to CD3 antibody, CD 16 antibody, CD19 antibody, CD56 antibody In some embodiments, for example, a negative selection is performed to obtain the cells of interest by contacting the PBMCs with anti-CD3 antibody beads. In some embodiments, for example, a negative selection is performed to obtain the cells of interest by contacting the PBMCs with anti-CD16 antibody beads. In some embodiments, an anti-CD19 antibody is used, for example, anti-CD19 antibody-coated beads are used. In some embodiments, an anti-CD56 antibody may be used for negative selection. In some embodiments, an anti-TNFR2 antibody may be used for negative selection. In some embodiments, any one, or any number of combination of the antibodies may be used from a selection comprising CD3-binding antibody, CD8-binding antibody, CD16-binding antibody, CD19-binding antibody, CD56-binding antibody, CX3CR1 (fractalkine)-binding antibody, and TNFR2-binding antibody.

One critical issue is the need for a density gradient to obtain PBMC, since density gradients are not readily available for GMP-purposes and/or cannot be easily performed in a closed system. Whereas methods relying on plastic adherence are relatively cheap, other approaches like positive selection via anti-huCD14-Microbeads or negative selection may not be cost effective. Furthermore, with positive selection, there is the additional concern over the use of xenogeneic antibodies. In some embodiments, monocytes are isolated untouched to avoid activating the cells prematurely. This process is negative selection, and may be performed by elutriation.

Elutriation of monocytes can be performed with Elutrak, which allows for a fast and inexpensive isolation of untouched monocytes in large quantities within a closed system. Peripheral blood monocytes may be enriched directly from unmobilized leukapheresis products using a cell separator (Elutrak, Gambro BCT, Lakewood, Colo., USA) and single-use, functionally sealed disposable sets, containing 40-ml elutriation chamber. Cells separation occurs on the basis of sedimentation velocity, which is dependent on cell size and, or the density. Leukapheresis product may be loaded into the elutriation chamber using the cell inlet pump and subjected to a centrifugation at a speed of 2400 rpm. Thereafter, the centrifuge speed may be held constant, and the flow of elutriation media (PBS; Bio Whittaker, Walkersville, USA, supplemented with 1% human serum albumin; Aventis-Behring, Marburg, Germany) contained in two 3-1 pooling bags (T3006, Cell-Max GmbH, Munich, Germany), may be increased step-wise to allow for the elutriation of the specific cell fractions into the pre-attached collection bags.

In some embodiments, at least 10ˆ8 to about 10ˆ12 PBMCs are needed, from which cells of interest are isolated (enriched). In some embodiments, the cells of interest are CD14+ cells. In some embodiments the cells of interest are CD14+/CD16− cells. In some embodiments, the cells of interest are CD14+/CD16− cells, that may express high levels of a cell surface protein, other than CD14 or CD16. In some embodiments the cells of interest may express high levels of CCR2. In some embodiments, total cells prior to isolation of cells of interest may be about 10ˆ8, 5×10ˆ8, 10ˆ9, 5×10ˆ9, 10ˆ10, 5×10ˆ10, 10ˆ11, 5×10ˆ11, 10ˆ12, 5×10ˆ12 cells, or more. In some embodiments, the total number of PBMCs before isolation of cells of interest may be at least 10ˆ9 to about 10ˆ12 cells. In some embodiments, total cells prior to isolation of cells of interest may be about 2×10ˆ9, 3×10ˆ9, 4×10ˆ9, 5×10ˆ9, 6×10ˆ9, 7×10ˆ9, 8×10ˆ9, 9×10ˆ9, or 10ˆ10 cells; about 2×10ˆ10, 3×10ˆ10, 4×10ˆ10, 5×10ˆ10, 6×10ˆ10, 7×10ˆ10, 8×10ˆ10, 9×10ˆ10 cells or 10ˆ11 cell; about 2×10ˆ11, 3×10ˆ11, 4×10ˆ11, 5×10ˆ11, 6×10ˆ11, 7×10ˆ11, 8×10ˆ11, 9×10ˆ11, or 10ˆ12 cells; about 5×10ˆ12, or more.

In some embodiments, the cells of interest that are recovered following an isolation procedure, for example using an antibody coated beads as described above may be a fraction of the total PBMCs counted at a time prior to isolation. In some embodiments, the cells of interest after isolation may be at least 10ˆ7 cells. In some embodiments, the cells of interest after isolation may be at least 10ˆ8 cells. In some embodiments, the cells of interest after isolation may be at least 10ˆ9 cells. In some embodiments, the cells of interest after isolation may be at least 10ˆ10 cells. In some embodiments, the cells of interest after isolation may be about 2×10ˆ7 cells. In some embodiments, the cells of interest after isolation may be about 3×10ˆ7 cells. In some embodiments, the cells of interest after isolation may be about 4×10ˆ7 cells. In some embodiments, the cells of interest after isolation may be about 5×10ˆ7 cells. In some embodiments the cells of interest after isolation may be about 6×10ˆ7 cells. In some embodiments, the cells of interest after isolation may be about 7×10ˆ7 cells. In some embodiments, the cells of interest after isolation may be about 8×10ˆ7 cells. In some embodiments, the cells of interest after isolation may be about $9\times10^7$ cells. In some embodiments, the cells of interest after isolation may be about $10^8$ cells. In some embodiments, the cells of interest after isolation may be about $2\times10^8$ cells. In some embodiments, the cells of interest after isolation may be about $3\times10^8$ cells. In some embodiments, the cells of interest after isolation may be about $4\times10^8$ cells. In some embodiments, the cells of interest after isolation may be about $5\times10^8$ cells. In some embodiments, the cells of interest after isolation may be about $6\times10^8$ cells. In some embodiments, the cells of interest after isolation may be about $7\times10^8$ cells. In some embodiments, the cells of interest after isolation may be about $8\times10^8$ cells. In some embodiments, the cells of interest after isolation may be about $9\times10^8$ cells. In some embodiments, the cells of interest after isolation may be about $10^9$ cells. In some embodiments, the cells of interest after isolation may be about $2\times10^9$ cells. In some embodiments, the cells of interest after isolation may be about $5\times10^9$ cells. In some embodiments, the cells of interest after isolation may be about $8\times10^9$ cells. In some embodiments, the cells of interest after isolation may be about $9\times10^9$ cells. In some embodiments, the cells of interest after isolation may be about $10^{10}$ cells. In some embodiments, the cells of interest after isolation may be about $5\times10^{10}$ cells. In some embodiments, the cells of interest after isolation may be about $10^{11}$ cells. In some embodiments, the cells of interest after isolation may be about $5\times10^{11}$ cells, or more.

In some embodiments, the isolation process may enrich the cells of interest by greater than 2-fold. In some embodiments, the isolation process may enrich the cells of interest by greater than 3-fold. In some embodiments, the isolation process may enrich the cells of interest by greater than 4-fold. In some embodiments, the isolation process may enrich the cells of interest by greater than 5-fold. In some embodiments, the isolation process may enrich the cells of interest by greater than 6-fold. In some embodiments, the isolation process may enrich the cells of interest by greater than 7-fold. In some embodiments, the isolation process may enrich the cells of interest by greater than 8-fold. In some embodiments, the isolation process may enrich the cells of interest by greater than 9-fold. In some embodiments, the isolation process may enrich the cells of interest by greater than 10-fold. In some embodiments, the isolation process may enrich the cells of interest by greater than 12-fold. In some embodiments, the isolation process may enrich the cells of interest by greater than 14-fold. In some embodiments, the isolation process may enrich the cells of interest by greater than 15-fold. In some embodiments, the isolation process may enrich the cells of interest by greater than 20-fold. In some embodiments, the isolation process may enrich the cells of interest by greater than 25-fold.

Characterization of Isolated Cells

Following isolation of cells of interest, cells are characterized. In most cases, an aliquot from the recovered cells of interest are carried through further assays for sampling the nature and functional characteristics. Cells are examined for cell viability using a suitable cell viability assay. Exemplary assays include trypan blue exclusion assay, LDH release assay, and NC200 assays. In some embodiments, automated viable cell counters such as the NucleoCounter NC 200 (Chemometec) are used, where only viable cells are counted and the total cell counts are equal to total viable cell counts.

In some embodiments, greater than at least 50% of the isolated cells may be CD14+ as determined by a suitable assay, such as a flow cytometry assay using an aliquot of the recovered cells. In some embodiments, greater than at least 60% of the isolated cells may be CD14+. In some embodiments, greater than at least 70% of the isolated cells may be CD14+. In some embodiments, greater than at least 71%, 72%, 73%, 74%, 75%, 76%, 77%, 78%, 79% or 80% of the isolated cells may be CD14+. In some embodiments, greater than 81%, 82%, 83%, 84%, 85%, 86%, 87%, 88%, 89%, or 90% of the isolated cells may be CD14+. In some embodiments, greater than 91% of the isolated cells may be CD14+. In some embodiments, greater than 92% of the isolated cells may be CD14+. In some embodiments, greater than 93% of the isolated cells may be CD14+. In some embodiments, greater than 94% of the isolated cells may be CD14+. In some embodiments, greater than 95% of the isolated cells may be CD14+. In some embodiments, greater than 96% of the isolated cells may be CD14+. In some embodiments, greater than 97% of the isolated cells may be CD14+. In some embodiments, greater than 98% of the isolated cells may be CD14+. In some embodiments, greater than 99% of the isolated cells may be CD14+.

Isolated cells may be CD16− as determined by a flow cytometry assay using an aliquot of the recovered cells. In some embodiments, at least 50% of the isolated cells may be CD16− as determined by a flow cytometry assay using an aliquot of the recovered cells. In some embodiments, at least 60% of the isolated cells may be CD16−. In some embodiments, at least 70% of the isolated cells may be CD16−. In some embodiments, greater than at least 71%, 72%, 73%, 74%, 75%, 76%, 77%, 78%, 79% or 80% of the isolated cells may be CD16−. In some embodiments, greater than 81%, 82%, 83%, 84%, 85%, 86%, 87%, 88%, 89%, or 90% of the isolated cells may be CD16−. In some embodiments, greater than 91% of the isolated cells may be CD16−. In some embodiments, greater than 92% of the isolated cells may be CD16−. In some embodiments, greater than 93% of the isolated cells may be CD16−. In some embodiments, greater than 94% of the isolated cells may be CD16−. In some embodiments, greater than 95% of the isolated cells may be CD16−. In some embodiments, greater than 96% of the isolated cells may be CD16−. In some embodiments, greater than 97% of the isolated cells may be CD16−. In some embodiments, greater than 98% of the isolated cells may be CD16−. In some embodiments, greater than 99% of the isolated cells may be CD16−.

In some embodiments, at least 70% of the isolated cells may be CD14+/CD16−. In some embodiments, at least 75% of the isolated cells may be CD14+/CD16−. In some embodiments, at least 80% of the isolated cells may be CD14+/CD16−. In some embodiments, at least 85% of the isolated cells may be CD14+/CD16−. In some embodiments, at least 90% of the isolated cells may be CD14+/CD16−. In some embodiments, at least 95% of the isolated cells may be CD14+/CD16−.

Isolated cells may comprise at least less than 5% CD3+ cells as determined by a flow cytometry assay using an aliquot of the recovered cells. Isolated cells may comprise at least less than 4% CD3+ cells. Isolated cells may comprise at least less than 3% CD3+ cells. Isolated cells may comprise at least less than 2% CD3+ cells. Isolated cells may comprise at least less than 5% CD19+ cells, as determined by a flow cytometry assay using an aliquot of the recovered cells. Isolated cells may comprise at least less than 4% CD19+ cells. Isolated cells may comprise at least less than 4% CD3+ cells. Isolated cells may comprise at least less than 3% CD19+ cells. Isolated cells may comprise at least less than 2% CD19+ cells. At least 5% of the isolated cells may be CD56− cells, as determined by a flow cytometry assay using an aliquot of the recovered cells. At least 4% of the isolated cells may be CD56− cells. At least 3% of the isolated cells may be CD56− cells. At least 2% of the isolated cells may be CD56− cells.

Following isolation cells may be further characterized by functional assays, such as phagocytosis assay, or chemotaxis assay. In some embodiments, cells having the above characteristics are further carried forward for developing into therapeutically effective myeloid cells. Cells may be frozen after isolation or advanced into the next steps for preparation of a pharmaceutical composition. In some embodiments, the myeloid cell is not transformed or activated prior to administering to a subject in need thereof.

In some embodiments, the myeloid does not exhibit tonic signaling at the time of administering to the subject.

In some embodiments, the myeloid cell exhibits low phagocytosis prior to administering to a subject, or prior to activating ex vivo by an external stimulus, such as, with a cytokine, or a growth factor, or in presence of a target for phagocytosis. In some embodiments, the myeloid cell exhibits moderate phagocytosis prior to administering to a subject, or prior to activating ex vivo by an external stimulus, such as, with a cytokine, or a growth factor, or in presence of a target for phagocytosis. In some embodiments, the myeloid cell exhibits responsiveness to any one or more of: GMCSF, GCSF, IL-4, IL-1b, IL-6, TNF, CCL2, CCL5, CXCL1 or a combination thereof.

In some embodiments, the myeloid cell exhibits enhanced phagocytosis upon activating ex vivo by an external stimulus, such as, with a cytokine, or a growth factor, or in presence of a target for phagocytosis. In some embodiments, the myeloid cell exhibits about 1.1 fold, 1.2 fold, 1.5 fold, 1.7 fold, 2 fold, 3 fold, 4 fold, 5 fold, 6 fold, 7 fold, 8 fold, 9 fold, 10 fold, 11 fold, 12 fold, 13 fold, 14 fold, 14 fold, 17 fold, 20 fold or more enhanced phagocytosis upon activating ex vivo by an external stimulus, such as, with a cytokine, or a growth factor, or in presence of a target for phagocytosis, compared to an activated, terminally differentiated myeloid cell such as mature post activation macrophage. In some embodiments, the myeloid cell exhibits responsiveness to cytokines or chemokines, exemplified by any one or more of: GMCSF, GCSF, IL-4, IL-1b, IL-6, TNF, CCL2, CCL5, CXCL1 or a combination thereof.

In some embodiments, the myeloid cell isolated from a biological sample can further be differentiated into an M1 or M2 lineage. It is desirable that the myeloid cell upon isolation retains the potential for further differentiation into an M1 cell after administration in vivo.

Modification of Myeloid Cells:

In some embodiments, myeloid cells may be further modified or manipulated to develop a therapeutically effective myeloid cells. Isolated cells can be manipulated by expressing a gene or a fragment thereof in the cell, without altering its functional and developmental plasticity, differential potential and cell viability.

In some embodiments, myeloid cells may be further modified or manipulated to develop a therapeutically effective myeloid cells by expressing a non-endogenous polynucleotide into the cell. A non-endogenous polynucleotide may encode for a protein or a peptide. Alternatively, a non-endogenous polypeptide may be a non-coding sequence, such as an inhibitory RNA, or a morpholino.

In some embodiments, myeloid cells may be further modified or manipulated to develop a therapeutically effective myeloid cells by stably altering the genomic sequence of the cell. In some embodiments, the myeloid cell is manipulated by editing the myeloid cell genome using a CRISPR-CAS system. In some embodiments, one or more genes may be edited to silence the gene expression. In some embodiments, the myeloid cell is manipulated to delete a gene. In some embodiments, one or more genes may be edited to enhance the gene expression.

In some embodiments, the genetic material is introduced into a myeloid cell in the form of a messenger RNA, wherein the messenger RNA encodes a protein or a peptide, thereby rendering the myeloid cell therapeutically effective. In some embodiments, naked DNA or messenger RNA (mRNA) may be used to introduce the nucleic acid inside the myeloid cell. In some embodiments, DNA or mRNA encoding the chimeric antigen receptor is introduced into the phagocytic cell by lipid nanoparticle (LNP) encapsulation. mRNA is single stranded and may be codon optimized. In some embodiments the mRNA may comprise one or more modified or unnatural bases such as 5'-Methylcytosine, or Pseudouridine. mRNA may be 50-10,000 bases long. In one aspect the transgene is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long. In some embodiments, the mRNA comprises a transgene sequence that encodes a fusion protein. LNP encapsulated DNA or RNA can be used for transfecting a macrophage or can be administered to a subject.

In some embodiments, a polynucleotide may be introduced into a myeloid cell in the form of a circular RNA (circRNAs). In circular RNAs (circRNAs) the 3' and 5' ends are covalently linked. CircRNA may be delivered inside a cell using LNPs. In some embodiments, a stable integration of transgenes into macrophages and other phagocytic cells may be accomplished via the use of a transposase and transposable elements, in particular, mRNA-encoded transposase. In one embodiment, Long Interspersed Element-1 (L1) RNAs may be contemplated for retrotransposition of the transgene and stable integration into a macrophage or a phagocytic cell. Retrotransposon may be used for stable integration of a recombinant nucleic acid encoding a phagocytic or tethering receptor (PR) fusion protein (PFP).

In some embodiments, the myeloid cell may be modified by expressing a transgene via incorporation of the transgene in a transient expression vector. In some embodiments expression of the transgene may be temporally regulated by a regulator from outside the cell. Examples include the Tet-on Tet-off system, where the expression of the transgene is regulated via presence or absence of tetracycline.

In some embodiments, the myeloid cell may be modified to develop a therapeutically effective cell by contacting the cell with a compound, which compound may be an inhibitor or an activator of a protein or enzyme within the myeloid cell.

In some embodiments, a polynucleotide encoding a chimeric antigen receptor may be introduced into an isolated myeloid cell that is obtained by the method described in the preceding section, where the chimeric antigen receptor upon expression in the myeloid cell augments an innate immune response function of the myeloid cell. In some embodiments, the chimeric antigen receptor expression can direct a myeloid cell to a specific target in vivo or in vitro. In some embodiments, the chimeric antigen receptor may increase the phagocytic potential of the myeloid cell. In some embodiments, the chimeric antigen receptor increases the immunogenicity of the myeloid cell. In some embodiments, the chimeric antigen receptor may increase augment intracellular signaling. In some embodiments, the chimeric antigen receptor may function cooperatively with one or more proteins within the cell. In some embodiments, the chimeric antigen receptor may dimerize or multimerize with a second receptor or transmembrane protein inside the myeloid cell, where the second receptor or transmembrane protein is an endogenous protein. In some embodiments, the method provided herein comprises isolation and manipulation of a myeloid cell in less than 72 hours, 70 hours, 65 hours, 60 hours, 55 hours, 50 hours, 45 hours, 40 hours, or 35 hours, or 30 hours, or 28 hours, or 26 hours or 24 hours. In some embodiments, the myeloid cell may be culture for less than 24 hours, or less than 20 hours or less than 16 hours, or less than 14 hours, or less than 12 hours, or less than 10 hours, or less than 8 hours, or less than 6 hours or less than about 4 hours. The myeloid cell following isolation and manipulation may be cultured briefly and frozen till further use. In some embodiments, the myeloid cell is thawed once or at the most twice.

Pharmaceutical Composition

Provided herein is a pharmaceutical composition comprising a population of cells comprising a recombinant polynucleic acid, wherein the recombinant polynucleic acid comprises a sequence encoding a chimeric fusion protein (CFP) or a sequence encoding an antigenic peptide. The population of cells comprises effector myeloid cells. In some embodiments, the effector myeloid cells are isolated and enriched from a population of PBMCs isolated from a biological sample, and the pharmaceutical composition comprises (i) at least 50% of the cells in the population of cells are CD14+ and CD16−, and (ii) less than 10% of the cells in the population of cells are dendritic cells; and a pharmaceutically acceptable excipient.

In some embodiments, the recombinant polynucleic acid comprises a sequence encoding a CFP, wherein the CFP comprises: (a) an extracellular domain comprising an antigen binding domain, and (b) a transmembrane domain operatively linked to the extracellular domain. In some embodiments the recombinant polynucleic acid comprising the sequence encoding a CFP, wherein the CFP comprises: (a) an extracellular domain comprising an antigen binding domain, and (b) a transmembrane domain and (c) one or more intracellular signaling domains, all of which are operatively linked to each other, such that when the extracellular domain binds to a target antigen, the intracellular domain is activated, activates intracellular signaling and activates the myeloid cell. An activated myeloid cell exhibits one or more of: higher phagocytosis activity, higher chemotaxis, increased inflammatory function, and higher killing of a phagocytosed cell or organism.

In some embodiments, the pharmaceutical composition is a therapeutic composition for an infectious disease, wherein the pharmaceutical composition comprises a population of cells comprising a CFP that has an extracellular antigen binding domain that binds a pathogenic antigen or an antigen displayed on an infected cell, for example, an antigen on a bacteria, a viral antigen, a fungal antigen, a protozoan antigen, etc.

In some embodiments, the pharmaceutical composition is a cancer therapeutic composition, wherein the pharmaceutical composition comprises a population of cells comprising a CFP that has an extracellular antigen binding domain that binds a cancer antigen. In some embodiments, the cancer antigen is a lymphoma antigen. In some embodiments, the pharmaceutical composition comprises effector myeloid cells that express a recombinant CFP, wherein, the antigen binding domain is a CD5 binding domain or a HER2 binding domain.

In some embodiments, the pharmaceutical composition comprises effector myeloid cells that express a recombinant CFP having a CD5 or HER2 antigen binding domain, and further comprises an intracellular domain derived from a phagocytic receptor or a scavenger receptor. In some embodiments the pharmaceutical composition as described above expresses a CFP, wherein the CFP comprises: (a) an extracellular domain comprising: (i) a scFv that specifically binds CD5 or HER2, and (ii) a hinge domain derived from CD8, or CD28 or an extracellular domain of CD68 or a portion thereof; (b) a CD8 transmembrane domain, a CD28 transmembrane domain or a CD68 transmembrane domain; and (c) an intracellular domain comprising at least two intracellular signaling domains, wherein the at least two intracellular signaling domains comprise: (i) a first intracellular signaling domain derived from FcγR or FcεR, and (ii) a second intracellular signaling domain that: (A) comprises a PI3-kinase (PI3K) recruitment domain, or (B) is derived from CD40. In some embodiments, the recombinant polynucleic acid comprises a sequence encoding an antigenic peptide, wherein the antigenic peptide is a CMVpp65 peptide.

In some embodiments, the therapeutically effective myeloid cells are directly formulated into a pharmaceutical composition for administration into a subject in need thereof. Alternatively, stored myeloid cells (frozen) are thawed once and tested for viability, stabilized in a nutrient rich medium for at least 1-4 hours, and then formulated in a pharmaceutical composition. The pharmaceutical composition comprises the myeloid cells and at least one excipient. In some embodiments, the excipient comprises a sterile buffer, (e.g. HEPES or PBS) at neutral pH. In some embodiment, the pH of the pharmaceutical composition is at 7.5. In some embodiments, the pH may vary within an acceptable range. In some embodiments, the engineered cells may be comprised in sterile enriched cell suspension medium comprising complement deactivated or synthetic serum. In some embodiments the pharmaceutic composition further comprises cytokines, chemokines or growth factors for cell preservation and function. In some embodiments, a single therapeutic dose may be suspended in a total volume of 1 ml-100 ml. In some embodiments, the single therapeutic dose may be suspended in a total volume of 1-25 ml, or 1-20 ml, or 1-15 ml, or 1-10 ml, or 1-5 ml. In some embodiments, the suspension volume is about 1 ml. In some embodiments, the suspension volume is about 5 ml. In some embodiments, the suspension volume is about 10 ml. In some embodiments, the pharmaceutical composition comprises about 10^6 effector myeloid cells to about 10^12 effector myeloid cells. In some embodiments, the pharmaceutical composition comprises about 10^6 effector myeloid cells per ml to about 10^8 effector myeloid cells per ml.

In some embodiments, the pharmaceutical composition may comprise additional therapeutic agents, co-administered with the engineered effector myeloid cells that express a CFP.

Treatment Methods

Provided herein are methods for treating an immunological disease, for example an infectious disease or cancer. In some embodiments the methods are useful for treating a bacterial disease. In some embodiments the methods are useful for treating a viral for treating a viral disease. In some embodiments the methods are useful in treating an immunological disease.

In some embodiments, the pharmaceutical composition comprises a population of cells comprising therapeutically effective dose of the myeloid cells. In some embodiments, the population of cells:

a. differentiate into effector cells in the subject after administration;
b. infiltrate into a diseased site of the subject after administration or migrate to a diseased site of the subject after administration; or
c. have a life-span of at least 5 days in the subject after administration.

Provided herein are methods for treating cancer in a subject using a pharmaceutical composition comprising engineered phagocytic cells, particularly macrophages, expressing recombinant nucleic acid encoding a phagocytic receptor (PR) fusion protein (PFP), which is specifically designed to target, attack and kill cancer cells. The PFP is also designated as a chimeric antigenic receptor for phagocytosis (CAR-P), and both the terms may be used interchangeably herein. The engineered phagocytic cells are also designated as CAR-P cells in the descriptions herein.

Cancers include, but are not limited to T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells. In some aspects a patient or a subject having cancer, is treated with autologous cells, the method comprising, isolation of PBMC-derived macrophages, modifying the macrophages ex vivo to generate highly phagocytic macrophages capable of tumor lysis by introducing into the macrophages a recombinant nucleic acid encoding chimeric antigenic receptor for phagocytosis which is a phagocytic receptor fusion protein (PFP), and administering the modified macrophages into the patient or the subject.

In one aspect, a subject is administered one or more doses of a pharmaceutical composition comprising therapeutic phagocytic cells, wherein the cells are allogeneic. An HLA may be matched for compatibility with the subject, and such that the cells do not lead to graft versus Host Disease, GVHD. A subject arriving at the clinic is HLA typed for determining the HLA antigens expressed by the subject, prior to determining a therapeutic or therapeutic regimen.

In some embodiments a therapeutically effective dose ranges between 10^7 cells to 10^12 myeloid cells for one infusion. The cell number may vary according to the age, body weight and other subject-related parameters and can be determined by a medical practitioner. In some embodiments, a therapeutically effective dose is about 10^7 myeloid cells. In some embodiments, a therapeutically effective dose is about 2×10^7 myeloid cells. In some embodiments, a therapeutically effective dose is about 3×10^7 myeloid cells. In some embodiments, a therapeutically effective dose is about 4×10^7 myeloid cells. In some embodiments, a therapeutically effective dose is about 5×10^7 myeloid cells. In some embodiments, a therapeutically effective dose is about 6×10^7 myeloid cells. In some embodiments, a therapeutically effective dose is about 7×10^7 myeloid cells. In some embodiments, a therapeutically effective dose is about 8×10^7 myeloid cells. In some embodiments, a therapeutically effective dose is about 9×10^7 myeloid cells. In some embodiments, a therapeutically effective dose is about 10^8 myeloid cells. In some embodiments, a therapeutically effective dose is about 2×10^8 myeloid cells. In some embodiments, a therapeutically effective dose is about 3×10^8 myeloid cells. In some embodiments, a therapeutically effective dose is about 4×10^8 myeloid cells. In some embodiments, a therapeutically effective dose is about 5×10^8 myeloid cells. In some embodiments, a therapeutically effective dose is about 6×10^8 myeloid cells. In some embodiments, a therapeutically effective dose is about 7×10^8 myeloid cells. In some embodiments, a therapeutically effective dose is about 8×10^8 myeloid cells. In some embodiments, a therapeutically effective dose is about 9×10^8 myeloid cells. In some embodiments, a therapeutically effective dose is about 10^9 myeloid cells. In some embodiments, a therapeutically effective dose is about 2×10^9 myeloid cells. In some embodiments, a therapeutically effective dose is about 3×10^9 myeloid cells. In some embodiments, a therapeutically effective dose is about 4×10^9 myeloid cells. In some embodiments, a therapeutically effective dose is about 5×10^8 myeloid cells. In some embodiments, a therapeutically effective dose is about 6×10^8 myeloid cells. In some embodiments, a therapeutically effective dose is about 7×10^8 myeloid cells. In some embodiments, a therapeutically effective dose is about 8×10^8 myeloid cells. In some embodiments, a therapeutically effective dose is about 9×10^8 myeloid cells. In some embodiments, a therapeutically effective dose is about 10^9 myeloid cells. In some embodiments, a therapeutically effective dose is about 5×10^9 myeloid cells. In some embodiments a therapeutically effective dose is about 10^10 myeloid cells. In some embodiments a therapeutically effective dose is about 5×10^10 myeloid cells. In some embodiments a therapeutically effective dose is about 10^11 myeloid cells. In some embodiments a therapeutically effective dose is about 5×10^11 myeloid cells. In some embodiments a therapeutically effective dose is about 10^12 myeloid cells.

Embodiments

1. A composition comprising a population of CD14+/CD16− cells, wherein the population of CD14+/CD16− cells is an engineered population of cells and/or comprises an exogenous agent.

2. A composition comprising a population of cells, wherein the population of cells is an engineered population of cells and/or comprises an exogenous agent, wherein the population of cells is CD14+ and/or CD16−, and wherein (a) the population of cells expresses CCR2 and/or CCR5;

(b) the population of cells is CD63+;

(c) the population of cells is CD56−, CD3−, and/or CD19−;

(d) the population of myeloid cells comprises less than 40% macrophage cells and/or less than 10% dendritic cells (DCs); and/or (e) the exogenous agent comprises a recombinant nucleic acid comprising a sequence encoding a chimeric antigen receptor (CAR) and the population of cells lacks tonic signaling through the CAR.

3. A composition comprising a population of cells, wherein the population of cells is an engineered population of cells and/or comprises an exogenous agent, wherein the population of cells is CD14+ and/or CD16−, and wherein (a) the population of cells is unpolarized myeloid cells;

(b) the population of cells differentiates into effector cells in the subject after administration;

(c) the population of cells infiltrates into a diseased site of the subject after administration or migrates to a diseased site of the subject after administration; or (d) the population of cells have a life-span of at least 5 days in the subject after administration.

4. A pharmaceutical composition comprising the composition of any one of the embodiments above and a pharmaceutically acceptable excipient.

5. A method of treating a disease or condition in a subject in need thereof, comprising: administering the pharmaceutical composition of the embodiment in paragraph 4 to the subject.

6. A method of treating a disease or condition in a subject in need thereof, comprising: administering to the subject a pharmaceutical composition comprising a population of cells, wherein the population of cells is an engineered population of cells and/or comprises an exogenous agent, wherein the population of cells is CD14+ and/or CD16−, and wherein (a) the pharmaceutical composition is administered to the subject within 72 hours after (i) the exogenous agent has been introduced into the population of cells or (ii) the population of cells has been engineered;

(b) the population of myeloid cells has been cultured for less than 48 days ex vivo prior to administration;

(c) the population of cells is obtained by a method that does not comprise stem cell mobilization; and/or (d) the population of cells is obtained by negative selection.

7. A method of treating a disease or condition in a subject in need thereof, comprising: administering to the subject a composition comprising a myeloid cell, wherein the myeloid cell (a) is characterized by one or more of:

(i) having a strong CD14 expression;

(ii) having a low or undetectable CD16 expression;

(iii) expressing CCR2 and/or CCR5;

(iv) having an ability to differentiate into multiple myeloid lineage subtypes upon receiving one or more suitable stimuli;

and, (b) comprises an exogenous agent, wherein when modified by the exogenous agent ex vivo, the exogenous agent does not alter differentiation or polarization state of the myeloid cell.

8. The composition or method of any one of the above embodiments, wherein the myeloid cell is CD16− (CD16 negative) or CD16low (CD16 low).

9. The composition or method of any one of the above embodiments, wherein the myeloid cell is CD14+ (CD14 positive).

10. The composition or method of any one of the above embodiments, wherein the myeloid cell is CCR2+ (CCR2 positive) and/or CCR5+ (CCR5 positive).

11. The composition or method of any one of the above embodiments, wherein the myeloid cell is capable of differentiating into an effector cell in the subject after administering the pharmaceutical composition.

12. The composition or method of any one of the above embodiments, wherein the myeloid cell is capable of migrating to a diseased site of the subject after administering the pharmaceutical composition.

13. The composition or method of any one of the above embodiments, wherein the myeloid cell is capable of infiltrating into a diseased site of the subject after administering the pharmaceutical composition.

14. The composition or method of any one of the above embodiments, wherein the myeloid cell is CD14+/CCR2+.

15. The composition or method of any one of the above embodiments, wherein the myeloid cell is CD14+/CCR5+.

16. The composition or method of any one of the above embodiments, wherein the myeloid cell is CD14+/CCR2+/CCR5+.

17. The composition or method of any one of the above embodiments, wherein the myeloid cell is CD63+.

18. The composition or method of any one of the above embodiments, wherein the exogenous agent is a recombinant nucleic acid, a peptide, a carbohydrate, a lipid or a small molecule.

19. The composition or method of any one of the above embodiments, wherein the exogenous agent comprises a recombinant nucleic acid comprising a sequence encoding a peptide, wherein the peptide is a chimeric antigen receptor (CAR).

20. The composition or method of any one of the above embodiments, wherein the myeloid cell has been cultured for less than 2 days in vitro at the time of administering the pharmaceutical composition.

21. The composition or method of any one of the above embodiments, wherein the myeloid cell retains cellular plasticity at the time of administering the pharmaceutical composition.

22. The composition or method of any one of the above embodiments, wherein at the time of administering the myeloid cell expresses a CAR.

23. The composition or method of any one of the above embodiments, wherein at the time of administering the pharmaceutical composition, the myeloid cell does not exhibit a tonic signaling by the CAR.

24. The composition or method of any one of the above embodiments, wherein the population of myeloid cells is obtained by a method comprising subjecting an isolated plurality of myeloid cells to a manipulation in vitro.

25. The composition or method of any one of the above embodiments, wherein the population of myeloid cells is obtained by a method that does not comprise stem cell mobilization.

26. The composition or method of any one of the above embodiments, wherein the plurality of myeloid cells are isolated from a biological sample by a negative selection using antibody-mediated binding of one or more myeloid cells in the biological sample.

27. The method of the embodiment in paragraph 26, wherein the negative selection is performed using flow cytometry.

28. The method of the embodiment in paragraph 26, wherein the plurality of isolated myeloid cells are (i) CD3− (negative), (ii) CD16− (negative) or CD16low, (iii) CD19− (negative); (iv) CD56− (negative); and (v) CD14+ (positive).

29. The composition or method of any one of the above embodiments, wherein the population of myeloid cells are CD16-CD56-CD3-CD19− cells that are obtained by a negative selection of a plurality of myeloid cells isolated from a biological sample.

30. The method of the embodiment in paragraph 29, wherein the biological sample is a peripheral blood sample.

31. The method of the embodiment in paragraph 29, wherein the biological sample is an apheresis sample.

32. The method of the embodiment in paragraph 24, wherein the biological sample is heterologous or autologous to the subject.

33. The composition or method of any one of the above embodiments, wherein at least 50% of myeloid cells of the population of myeloid cells is undifferentiated.

34. The composition or method of any one of the above embodiments, wherein the population of myeloid cells comprises M0 monocytes.

35. The composition or method of any one of the above embodiments, wherein the population of myeloid cells comprises M1 monocytes.

36. The composition or method of any one of the above embodiments, wherein the population of myeloid cells comprises M2 monocytes.

37. The composition or method of any one of the above embodiments, wherein at least 50% of myeloid cells of the population of myeloid cells are unpolarized.

38. The composition or method of any one of the above embodiments, wherein the subject is human.

39. The composition or method of any one of the above embodiments, wherein the disease or condition is selected from a cancer, an infection, an autoimmune disease, an inflammatory disease, a metabolic disease, a neurodegenerative disease and a monogenic, polygenic or multifactorial disease or disorder.

40. The composition or method of any one of the above embodiments, wherein the disease or condition is a cancer.

41. The composition or method of any one of the above embodiments, wherein the disease or condition is a bacterial, viral, mycological or parasitic infection.

42. The composition or method of any one of the above embodiments, wherein the disease or condition is neurodegeneration.

43. A method for isolating therapeutically effective myeloid cells, comprising:

(a) negatively selecting therapeutically effective myeloid cells from a biological sample comprising myeloid cells, by (i) contacting the biological sample with one or more antibodies selected from anti-CD16 antibody, anti-CD56 antibody, anti-CD3 antibody, and anti-CD19 antibody, and (ii) eliminating the cells in the biological sample that are bound by the one or more antibodies, thereby isolating therapeutically effective myeloid cells that are relatively unperturbed in the process.

44. The method of the embodiment in paragraph 43, wherein the isolated therapeutically effective myeloid cells are CD14+.

45. The method of the embodiment in paragraph 43, wherein the isolated therapeutically effective myeloid cells are CD14hi.

46. The method of the embodiment in paragraph 43, wherein the isolated therapeutically effective myeloid cells are CD16− or CD16low.

47. The method of the embodiment in paragraph 43, wherein the isolated therapeutically effective myeloid cells retain the ability to differentiate into myeloid lineage subsets in response to a suitable stimulus.

48. The method of the embodiment in paragraph 43, wherein the isolated therapeutically effective myeloid cells are capable of further differentiating into polarized monocytes, macrophages, DC1, DC2, DC3, DC4, DC5 DC6 dendritic cells, or any combination thereof.

49. The method of the embodiment in paragraph 43, wherein the isolated therapeutically effective myeloid cells retain the ability to polarize towards M1 and M2 phenotypes in response to a suitable stimulus.

50. A method for generating a population of myeloid cells for treating a subject in need thereof, the method comprising:

(i) isolating a plurality of myeloid cells from a biological sample, wherein the plurality of myeloid cells exhibits cellular plasticity;

(ii) subjecting the plurality of myeloid cells isolated from the biological sample to a manipulation in vitro using an exogenous agent, and obtaining the population of myeloid cells; wherein the manipulation in vitro does not alter the cellular plasticity of the plurality of myeloid cells; and (iii) preparing a therapeutic composition comprising the population of myeloid cells and an acceptable excipient.

51. The method of the embodiment in paragraph 50, wherein the subject is human.

52. The method of the embodiment in paragraph 50, wherein the biological sample is a peripheral blood sample, an apheresis sample, a leukapheresis sample, or an umbilical cord blood sample.

53. The method of the embodiment in paragraph 50, wherein the biological sample is derived from the subject.

54. The method of the embodiment in paragraph 50, wherein the biological sample is derived from a suitable human donor.

55. The method of the embodiment in paragraph 50, wherein isolating a plurality of myeloid cells from a biological sample comprises isolating CD14+ cells by a negative selection.

56. The method of the embodiment in paragraph 55, wherein the negative selection is achieved by contacting cells in the human sample with one or more antibodies selected from a group consisting of anti-CD16 antibody, anti-CD56 antibody, anti-CD3 antibody, and anti-CD19 antibody, and immobilizing or eliminating the cells in the human sample that are bound by the one or more antibodies.

57. The method of the embodiment in paragraph 55, wherein the negative selection is performed by flow cytometry.

58. The method of the embodiment in paragraph 50, wherein the plurality of myeloid cells isolated from the biological sample are CD14+, and do not express CD3, CD19, CD56 and/or CD16.

59. The method of any one of the embodiments 43-58, wherein the myeloid cells are undifferentiated, or unpolarized.

60. The method of the embodiment in paragraph 50, wherein the exogenous agent is a recombinant nucleic acid, a peptide, a carbohydrate, a lipid or a small molecule.

61. The method of the embodiment in paragraph 50, wherein the manipulation comprises genetically engineering the plurality of myeloid cells.

62. The method of the embodiment in paragraph 50 or 61, wherein the manipulation comprises introducing a recombinant nucleic acid comprising a sequence encoding a peptide to the plurality of myeloid cells.

63. The method of the embodiment in paragraph 60, wherein the recombinant nucleic acid is an RNA.

64. The method of the embodiment in paragraph 63, wherein the recombinant nucleic acid is an mRNA.

65. The method of the embodiment in paragraph 63, wherein the population of myeloid cells, upon introduction of the nucleic acid comprising a sequence encoding a peptide, expresses the peptide.

66. The method of the embodiment in paragraph 63, wherein the peptide is a chimeric antigen receptor (CAR).

67. The method of the embodiment in paragraph 66, wherein the peptide comprises: (i) a transmembrane domain; (ii) an extracellular region comprising at least a target-binding domain that binds to a surface component of a second cell; and (iii) an intracellular region comprising one or more signaling domains.

68. The method of the embodiment in paragraph 67, wherein the second cell is a diseased cell or a cancer cell.

69. The method of the embodiment in paragraph 67, wherein the peptide comprises at least one intracellular phagocytosis signaling domain.

70. The method of any one of the embodiments 61-69, wherein the intracellular phagocytic signaling domain is operably linked to the extracellular target-binding domain and is configured to be activated upon binding of the extracellular target-binding domain to the surface component of the second cell.

71. The method of any one of the embodiments 61-70, wherein the introducing a recombinant nucleic acid comprises introducing via electroporation or nucleoporation.

72. The method of any one of the embodiments 61-70, wherein the introducing a recombinant nucleic acid comprises introducing via chemical delivery.

73. The method of any one of the embodiments 61-72, wherein the recombinant nucleic acid is stably incorporated into the genome of the cell.

74. The method of the embodiment in paragraph 73, wherein the incorporating is via activation of one or more of a transposase, an integrase, an endonuclease, a recombinase, and a reverse transcriptase.

75. The method of the embodiment in paragraph 50, wherein the preparing of the composition comprises suspending the cells in a pharmaceutically acceptable excipient.

76. The method of any one of the embodiments 61-75, wherein the population of myeloid cells retain cellular plasticity and ability to differentiate into multiple myeloid lineages following suitable stimuli.

77. The method of any one of the embodiments 61-76, wherein the population of myeloid cells do not exhibit a tonic signaling by the CAR.

78. The method of any one of the embodiments 61-77, wherein the population of myeloid cells express a functional CAR, and are capable of exhibiting CAR-mediated antigen specific response.

79. The method of the embodiment in paragraph 50 or 75, wherein the acceptable excipient is a buffer, a cell culture medium comprising nutrients, DMSO, glycerol, or a combination thereof.

80. The method of the embodiment in paragraph 50, wherein the composition is frozen until further use.

81. The method of the embodiment in paragraph 50, wherein the method is able to be conducted in less than 12 hours, less than 10 hours, less than 8 hours, less than 6 hours, less than 4 hours, or less than 2 hours.

82. The method of the embodiment in paragraph 50, wherein the method is completed in 2 hours or less.

83. The method of the embodiment in paragraph 50, wherein the plurality of myeloid cells is subjected to gene modification and/or editing, thereby obtaining the population of myeloid cells.

84. The method of the embodiment in paragraph 50, wherein the plurality of myeloid cells is subjected contacting with one or more antigenic peptides, thereby obtaining the population of myeloid cells that are antigen-loaded.

85. A method of manufacturing a population of myeloid cells using a method in any one of the embodiments 43-84, wherein the method is able to be conducted in about 6 hours or less; and wherein the population of myeloid cells are undifferentiated or unpolarized, exhibit cellular plasticity and lack tonic signaling.

86. The method of any of the embodiments 50-84, wherein the population of myeloid cells for cell therapy comprises any one or more of:

(a) greater than about 50% of live cells in the population that are CD14+ CD16−;

(b) greater than about 50% of live cells in the population that are CCR2+ and/or CCR5+;

(c) less than at least 50% of live cells in the population that express one or more of CD64, CD68, CD80, CD86, CD163, CD206, CD200R, CD31, CD71, CLEC9A, CD1C, and AXL/SIGLEC6;

(d) an M0 monocyte, (e) an M1 monocyte, (f) an M2 monocyte, (g) a dendritic cell, and (h) a pre-dendritic cells or a dendritic precursor cell.

87. A population of myeloid cells for use in cell therapy comprising undifferentiated or unpolarized cells, that have been isolated from a biological sample, and further manipulated in vitro using an external agent selected from a recombinant nucleic acid, a peptide, a carbohydrate, a compound and a small molecule, wherein, a myeloid cell in the population of myeloid cells are CD14+ CD16−; or are CD14hi and CD16lo; and exhibit one or more of the following:
(i) a cellular plasticity,
(ii) an ability to differentiate into multiple myeloid lineages,
(iii) an ability to migrate in vivo to a diseased tissue,
(iv) an ability to infiltrate a diseased tissue, and
(v) an ability sequester and/or destroy a disease-causing cell, tissue or organism.
88. The population of myeloid cells of the embodiment in paragraph 87 that are isolated via negative selection.
89. The method of the embodiment in paragraph 80, wherein the exogenous agent is a recombinant nucleic acid, a peptide, a carbohydrate, a lipid or a small molecule.
90. The population of myeloid cells of the embodiment in paragraph 87, wherein a cell of the population of myeloid cells comprises a recombinant nucleic acid having a sequence encoding a peptide.
91. The population of myeloid cells of the embodiment in paragraph 87, wherein a cell of the population of myeloid cells comprises a recombinant nucleic acid having a sequence encoding a CAR.
92. The population of myeloid cells of the embodiment in paragraph 87, wherein a cell of the population of myeloid cells expresses a CAR that exhibits CAR mediated activation.
93. The population of myeloid cells of the embodiment in paragraph 87, wherein a cell of the population of myeloid cells expresses a CAR, and does not exhibit tonic signaling by the CAR.
94. The population of myeloid cells of the embodiment in paragraph 87, wherein a cell of the population of myeloid cells is CD14+.
95. The population of myeloid cells of the embodiment in paragraph 87, wherein a cell of the population of myeloid cells is CD16−.
96. The population of myeloid cells of the embodiment in paragraph 87, wherein a cell of the population of myeloid cells is CD14highCD16low.
97. The population of myeloid cells of the embodiment in paragraph 87, wherein a cell of the population of myeloid cells is CD56−.
98. The population of myeloid cells of the embodiment in paragraph 87, wherein a cell of the population of myeloid cells is CD3−.
99. The population of myeloid cells of the embodiment in paragraph 87, wherein a cell of the population of myeloid cells is CD19−.
100. The population of myeloid cells of the embodiment in paragraph 87, wherein a cell of the population of myeloid cells expresses one or more chemokine receptors.
101. The population of myeloid cells of the embodiment in paragraph 87, wherein a cell of the population of myeloid cells expresses CCR2.
102. The population of myeloid cells of the embodiment in paragraph 87, wherein a cell of the population of myeloid cells expresses CCR5.
103. The population of myeloid cells of the embodiment in paragraph 87, wherein a cell of the population of myeloid cells expresses CCR2 and CCR5.
104. The population of myeloid cells of the embodiment in paragraph 87, wherein a cell of the population of myeloid cells is CD16-CD56-CD3-CD19−.
105. A pharmaceutical composition comprising the population of myeloid cells of the embodiment in paragraph 87-104.
106. The population of myeloid cells of the embodiment in paragraph 87, for use in a cancer therapy.
107. The population of myeloid cells of the embodiment in paragraph 87, for use in a therapy for neurodegeneration.
108. The population of myeloid cells of the embodiment in paragraph 87, wherein a cell in the population exhibit enhanced immunogenicity following administration as a cell therapy, compared to a cell that has not been manipulated in vitro.
109. The population of myeloid cells of the embodiment in paragraph 87, wherein a cell in the population exhibit enhanced cellular migration to a diseased tissue following administration as a cell therapy, compared to a cell that has not been manipulated in vitro.
110. The population of myeloid cells of the embodiment in paragraph 87, wherein a cell in the population exhibit enhanced phagocytic ability following administration as a cell therapy, compared to a cell that has not been manipulated in vitro.
111. The population of myeloid cells of the embodiment in paragraph 87, wherein a cell in the population exhibit enhanced cytotoxicity following administration as a cell therapy, compared to a cell that has not been manipulated in vitro.
112. The population of myeloid cells of the embodiment in paragraph 87, for use as a monotherapy.
113. The population of myeloid cells of the embodiment in paragraph 87, for use as a combination therapy.
114. A method for making a human myeloid cell for treating a human subject in need thereof, comprising:
(i) obtaining a plurality of myeloid cells comprising undifferentiated or unpolarized myeloid cells from an allogeneic or autologous biological sample via a negative selection using a plurality of antibodies comprising at least anti-CD16 antibody, anti-CD3 antibody, anti-CD56 antibody and anti-CD19 antibody;
(ii) engineering, culturing, stabilizing, activating, enriching and/or expanding the cells from step (i); and
(iii) administering the cells from step (ii) to the subject;
wherein the time lapse from obtaining in (i) to administering in (iii) is less than about 3 days.
115. The method of the embodiment in paragraph 103, wherein the biological sample is a peripheral blood sample.
116. The method of the embodiment in paragraph 103, wherein the biological sample is an apheresis sample.
117. The method of the embodiment in paragraph 103, wherein the cells from step (ii) are CD14+ CD16− or CD14hi and CD16lo.

EXAMPLES

Example 1. Isolation and Characterization of CD14+ Myeloid Cells

Figure 5A:
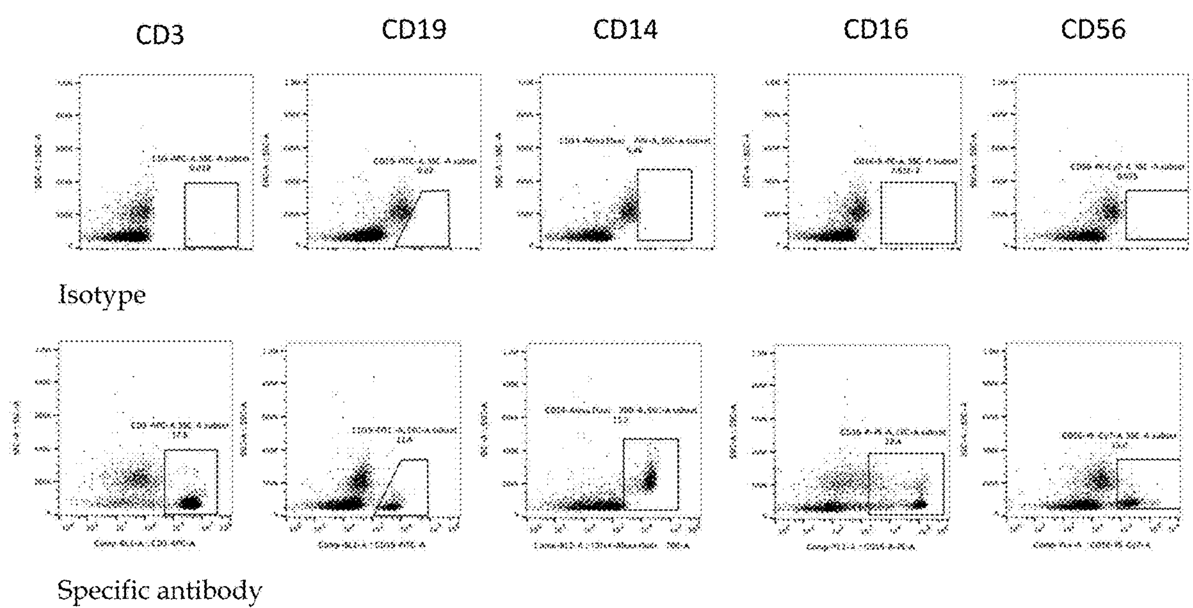
FIG. 5A shows flow cytometry analysis data before CD14+ cell isolation. Cells were analyzed for CD14, CD16, CD19 and CD56 markers.
Figure 5B:
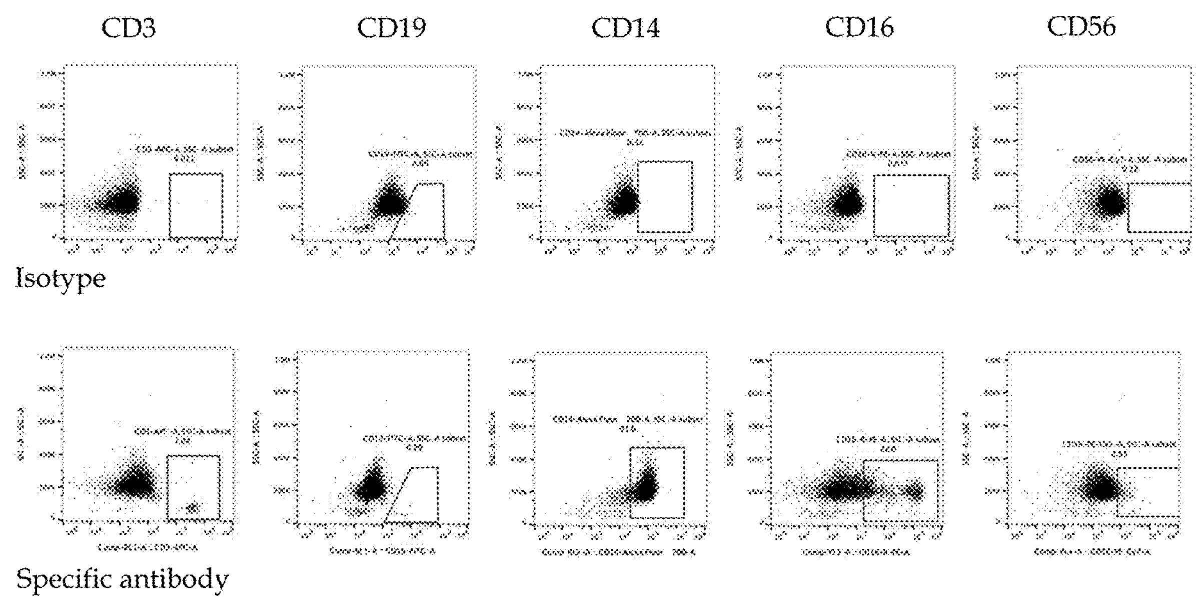
FIG. 5B shows flow cytometry analysis data after CD14+ cell isolation. Cells were analyzed for CD14, CD16, CD19 and CD56 markers.
Figure 6:
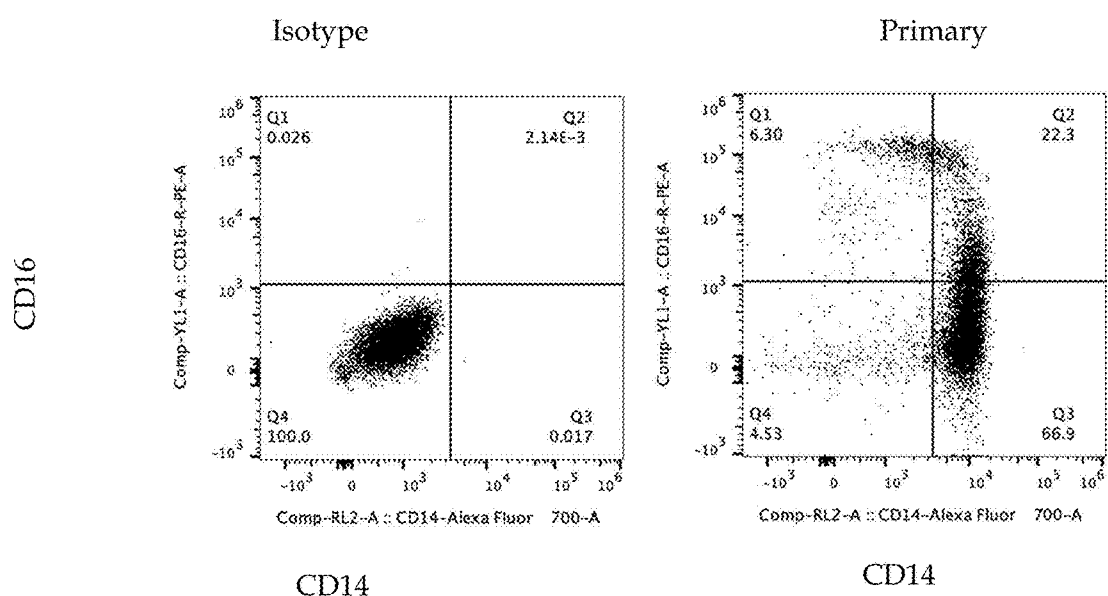
FIG. 6 shows flow cytometry analysis data after CD14+ isolation. Cells were analyzed for CD14 ansCD56 markers.

In this example, myeloid cells of interest were isolated to from leukapheresis sample, for preparation of myeloid effector cells for therapeutic use. Monocytes were isolated from commercial leukapheresis sample from human peripheral blood (Leukopak, Hemacare.com) using CD14 antibody mediated selection, and characterization of the cells pre- and post-isolation using antibodies to detect cell-specific surface markers. The positive selection using anti-CD14 antibody was performed in a cell separator column (LS Column. Miltenyi Biotec). Results shown in FIG. 4-FIG. 6 indicate that cells enriched from leukapheresis sample using CD14 antibody binding are largely monocytes that are substantially free from cells expressing various lymphocyte lineage markers CD3, CD19 and CD56. FIG. 4 upper and lower panels indicate the relative compositions of cell subtypes based on the indicated surface marker expression before (upper panel) and after (lower panel) isolation of CD14+ monocytes. Using specific markers and flow cytometric analysis, greater than 95% of the cells were found to be viable; and 91.6% of cells from the leukopak sample were CD14+ cells indicating high recovery. The leukapheresis sample before CD14 antibody mediated cell isolation comprised 57.8% CD3+ cells. The CD14+ antibody pulled a population of monocyte-enriched cells having only 2% cells that were CD3+, 2.53% cells that were CD56+ positive, and 0.29 cells that were CD19+ positive. 66.9% cells were CD14% and CD16−, and 22% cells were both CD14 and CD16 positive. FIGS. 5A and 5B show flow cytometry data of the pre- and post-isolation respectively, upper panels: flow cytometry using isotype control; lower panels: flow cytometry using the respective antibodies. FIG. 6 shows cytometric data of CD14+ post-isolation, stained with CD14 and CD16 antibodies: 6% CD14-CD16+; 22% CD14+ CD16+; and 66.9% CD14+ CD16− cells.

Isolated cells were cultured briefly in vitro and stimulated with exogenous agents to determine if the isolated CD14+ cells had the potential to be further differentiated into M0, M1 and M2 polarized macrophages. The exogenous agents used for stimulation are listed in Table 1 below.

TABLE 1

| Stimulus for inducing monocyte | |
|---|---|
| Phenotype | Stimulus |
| M0 | Regular medium (TexMACS/MCSF) |
| M1-1 (Low LPS) | Regular medium with 1 ng/ml LPS, 10 ng/ml IFNgamma |
| M1-2 (Medium LPS) | Regular medium with 10 ng/ml LPS, 10 ng/ml IFNgamma |
| M1-3 (High LPS) | Regular medium with 50 ng/ml LPS, 10 ng/ml IFNgamma |
| M2-1 (Low Cytokine) | Regular medium with 10 ng/ml IL4, IL10, TGFbeta |
| M2-2 (High Cytokine) | Regular medium with 20 ng/ml IL4, IL10, TGFbeta |

Figure 7:
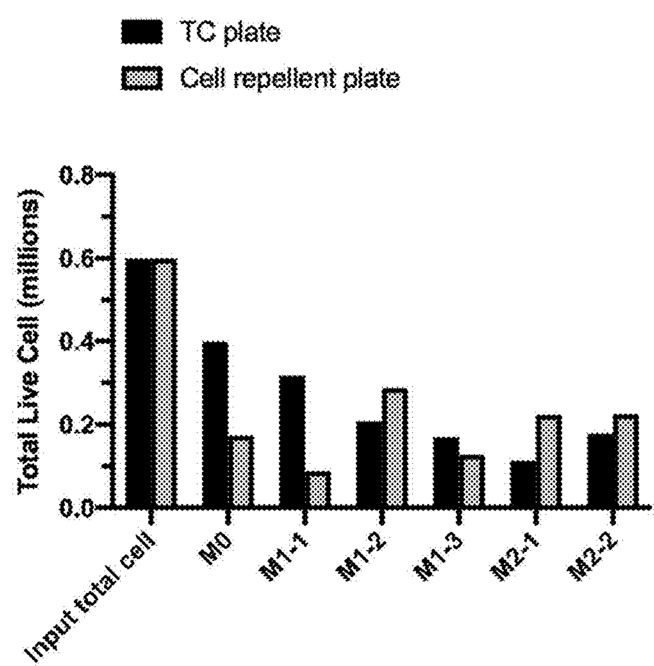
FIG. 7 shows data demonstrating differentiation of CD14+ cells into M0, M1 and M2 cells in presence of polarization stimuli.
Figure 8A:
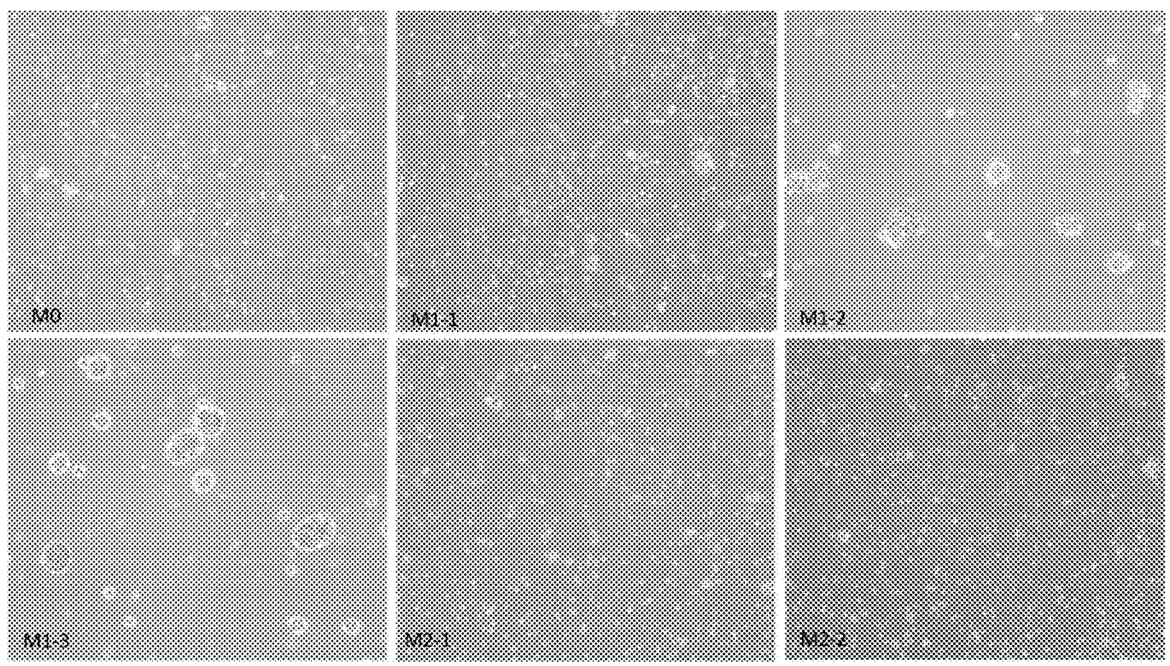
FIG. 8A shows photomicrographs of M0, M1 and M2 polarized CD14+ cells in culture for 24 hours in presence of polarizing stimuli.
Figure 8B:
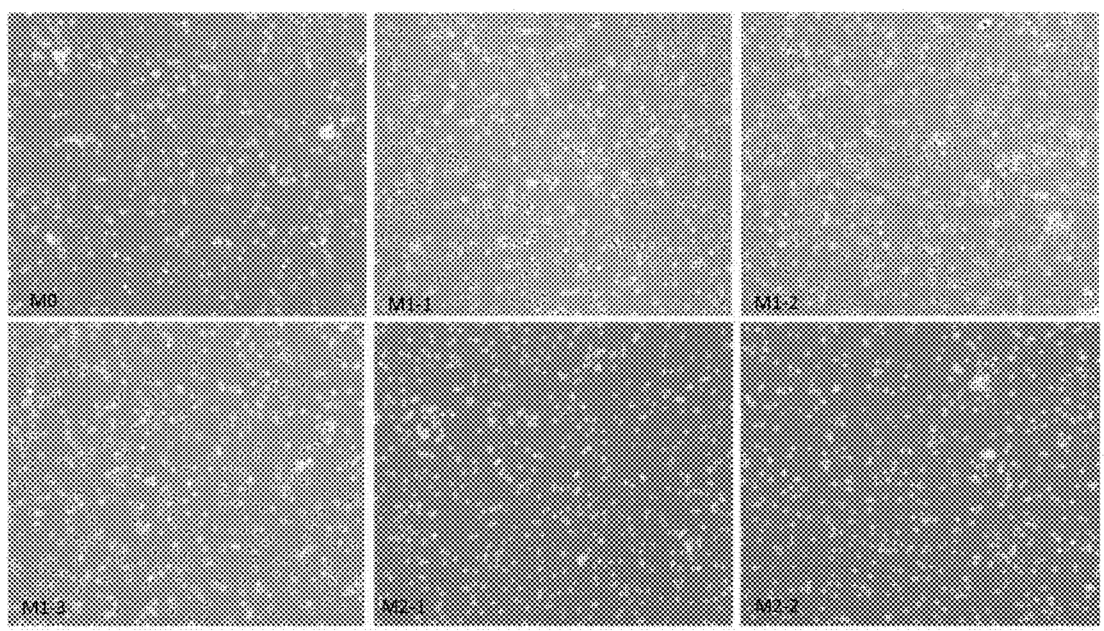
FIG. 8B shows photomicrographs of M0, M1 and M2 polarized CD14+ cells in culture for 48 hours in presence of polarizing stimuli.
Figure 9A:
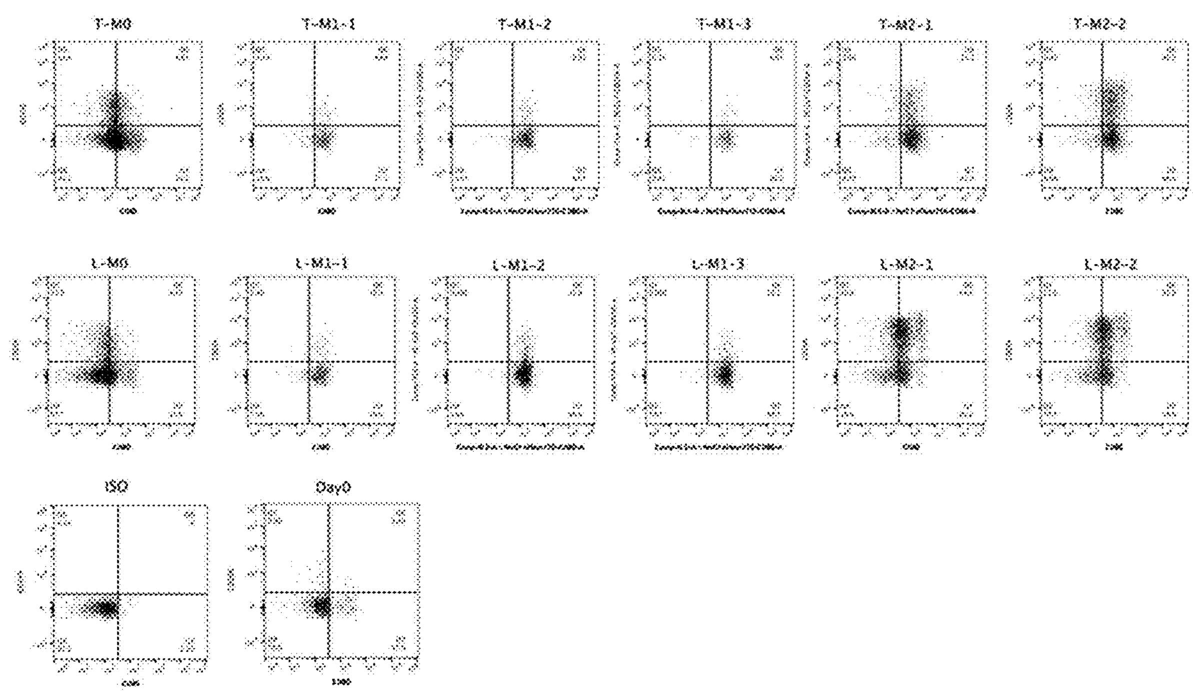
FIG. 9A shows flow cytometry data of CD206 expression in CD14+ cells in presence of polarizing stimuli.
Figure 9B:
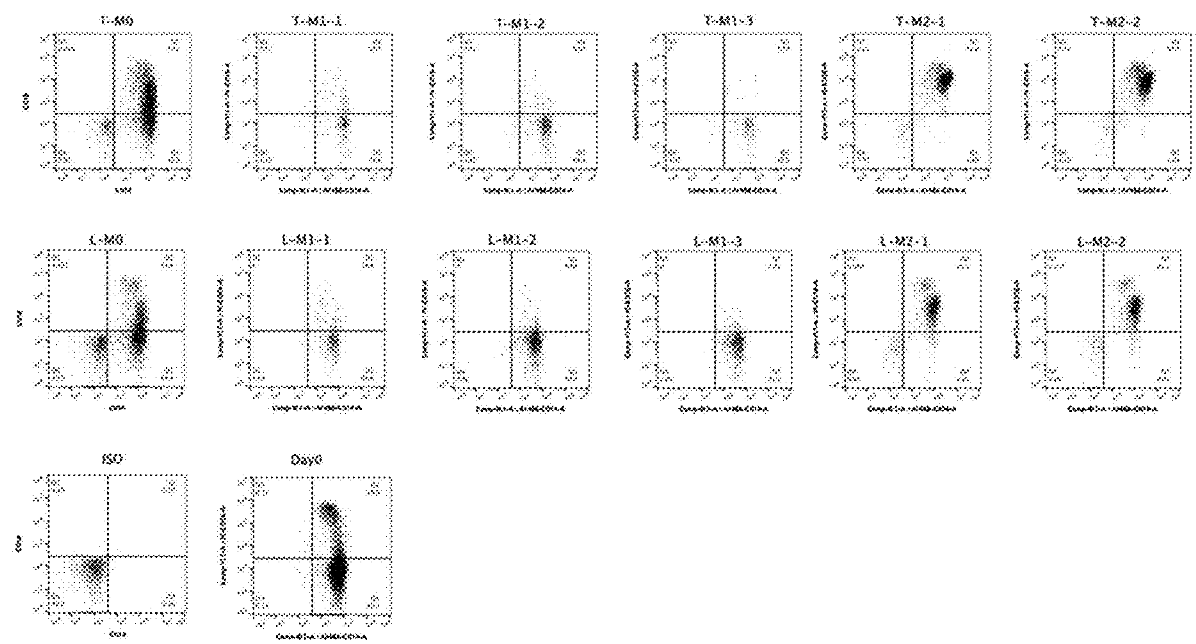
FIG. 9B shows flow cytometry data of CD14 and CD16 expression in CD14+ cells in presence of polarizing stimuli.
Figure 9C:
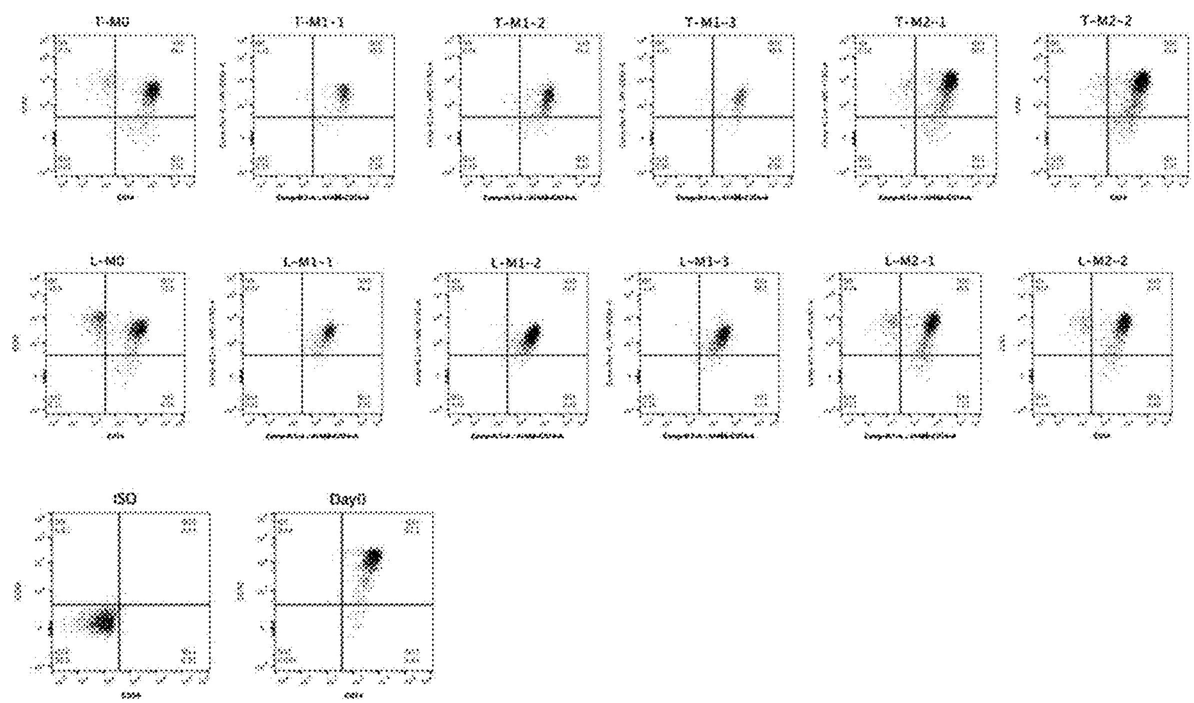
FIG. 9C shows flow cytometry data of CCR2 expression in CD14+ cells in presence of polarizing stimuli.

Cell culture was performed on regular tissue culture plates, or on low adhesion plates (cell repellant culture plates) (FIG. 7). Cells readily differentiated into M0, M1, M2 cells in response to the given stimuli as shown in FIG. 7, and cells cultured on cell repellant plates responded slightly better to M2 lineage polarization as compared to cells cultured on regular tissue culture plates. FIG. 8A and FIG. 8B show cellular phenotypes observed under light microscopy at 24 and 48 hour respectively. Both M1 or M2 polarizing stimuli led to an alteration of CD206 and CD80 expressions. CD206 was readily increased in M2 cells. M0 or M1 cells on the other hand did not show elevated CD206 expression. CD80 expression on the other hand was upregulated in M1 cells, and not in M2 cells (FIG. 9A). CD16 expression analysis shows that it is readily upregulated in culture, and is the upregulation is significantly higher in response to M2 stimuli. M1 polarized cells do not show upregulation of CD16 expression (FIG. 9B). CCR2 expression level is high in CD14+ cells. It is elevated in M1 and M2 phenotypes, indicating that the cells are capable of undergoing chemotactic migration to the site of inflammation or infection, or to a tumor site (FIG. 9C).

Example 2. Myeloid Cell (CAR-Expressing Effector Myeloid Cells) Manufacturing Process In this example, a process for isolation and development of therapeutically effective myeloid cells (also termed CAR-expressing effector myeloid cells) is described, which could be followed for scale. The process involves CD14+ cell isolation from a biological sample, altering the isolated cells by introducing a nucleic acid encoding a peptide to the cells, and preparing a therapeutic composition for delivery into a subject in need of a myeloid cell based therapy.

Figure 10:
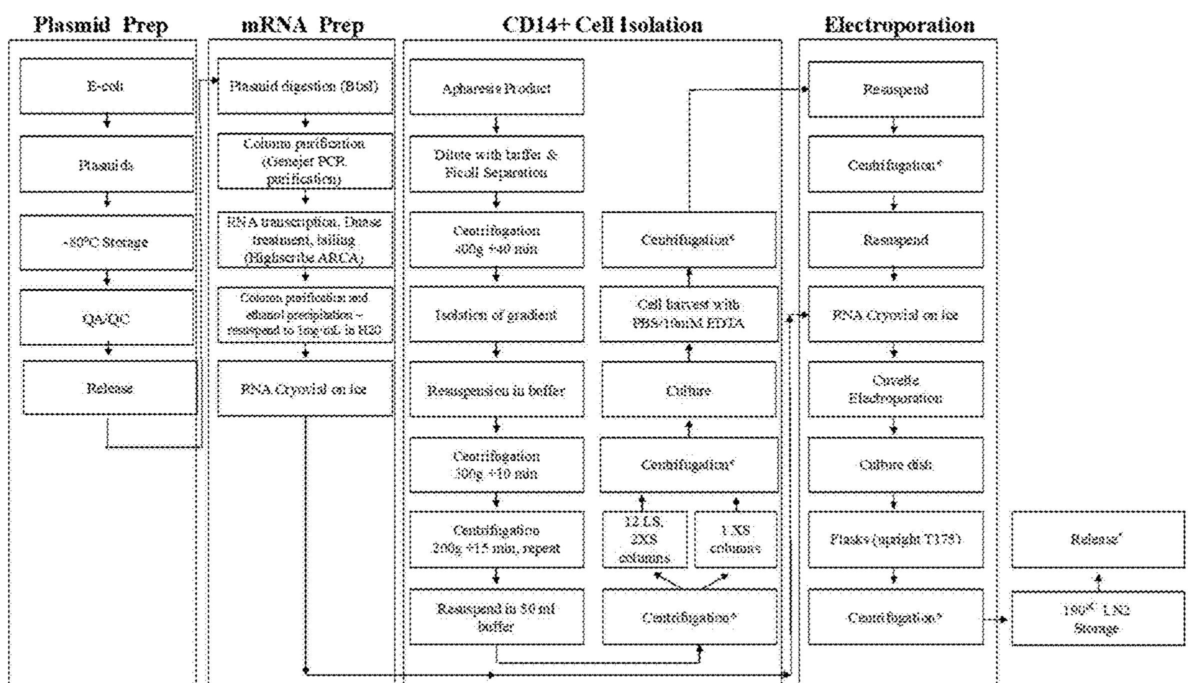
FIG. 10 is a diagrammatic representation of effector myeloid cell manufacturing.

FIG. 10 shows a schematic diagram of the process workflow.

Prior to isolation of cells, the recombinant nucleic acid for introducing into the cells is prepared. In this example, messenger RNA is introduced.

Preparation of Recombinant Nucleic Acid Encoding CAR:

Recombinant nucleic acid constructs are prepared that encode chimeric antigen receptor (CAR) and are incorporated in plasmid vectors for amplification and/or testing expression in an eukaryotic cell. In this example, several recombinant chimeric antigen receptors (CAR) are prepared. The recombinant CARs are constructed using molecular cloning techniques known in the art. A recombinant CAR protein comprises an intracellular domain, a transmembrane domain and an extracellular domain. Each domain or subsection of a domain can be encoded by a nucleic acid sequence that is generated by PCR from heterologous source sequences, and pieced together by cloning individually into the vector, or ligated into a longer nucleic acid that is then inserted into the multi-cloning sites of a suitable plasmid or vector with appropriate promoter and 3'-regulatory elements for amplification. Briefly, an exemplary CAR is prepared by incorporating a nucleic sequence encoding one or more signaling domains, (e.g., a PI3Kinase recruiting domain), a nucleic acid sequence encoding the CD8 hinge and transmembrane domain, a nucleic acid sequence encoding an extracellular domain, having a sequence encoding HER2 binding scFv (HER2 scFv) at the extracellular end. Certain constructs include a FLAG peptide sequence at the extracellular end designed such that it does not pose hindrance to the scFv binding to its target, for instance in this case, HER2. These components are ligated together into a sequence that encode a fully functional transmembrane CAR. The nucleic acid subunits encoding individual domains of the recombinant protein is designed to include intervening short flexible linker sequences between two domains. The construct is ligated in a plasmid having a promoter and 3' stabilizing structural units. In one variation, the construct is placed within an Alu retrotransposon element that encodes ORF2p and has the respective 5'- and 3'-UTR sequences, a CMV promoter. The plasmid is amplified in *E. coli*, validated by sequencing or stored in (−) 80° C.

mRNA Preparation mRNA was prepared by in vitro transcription using the digested plasmid as template and purified to remove contaminant DNA and polyadenylated. The RNA product is purified, resuspended to 1 mg/ml in RNase free water and stored in cryovials.

CD14+ Cell Isolation

Cells from an leukapheresis containers (Leukopak, Miltenyi Biotec) were diluted and subjected to Ficoll Separation. Centrifugation was performed at 400 g for 40 minutes. The monocyte enriched buffy layer was removed, washed in buffer, centrifuged lightly and resuspended in buffer and subjected to negative selection using a mixture of antibodies that bind CD3, CD16, CD19, CD56 and passing through cell separator column (LS Column. Miltenyi Biotec). The columns are designed to retain antibody bound cells, and the eluted cells were substantially free of cells expressing CD3, CD16, CD19, CD56. After repeated passage through the columns, cells were centrifuged, washed and cultured overnight prior to stabilization.

Electroporation and Storage/Release

The mRNAs sample encoding CAR was thawed on ice for electroporation. Cells were electroporated with mRNA using cuvette electroporation. Cells were cultured for a few hours before subjecting them to characterization or validation for release, or cryopreservation or processing for administration.

The steps from cell isolation to storage/release took place within 72 hours.

Figure 11:
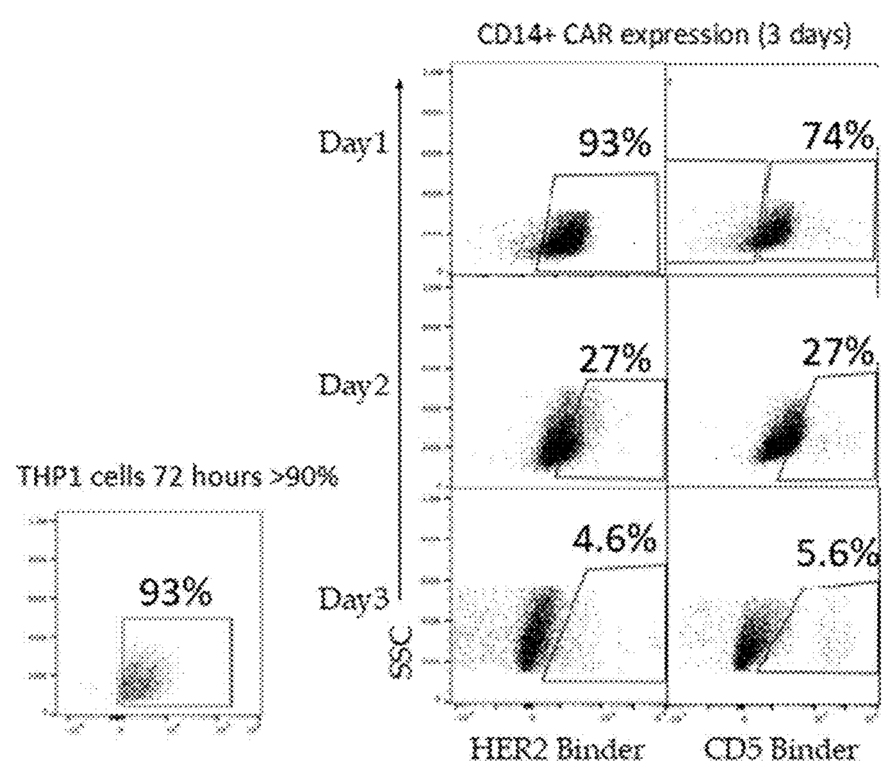
FIG. 11 shows flow cytometry data demonstrating CAR expression in CD14+ cells at indicated time after introducing recombinant nucleic acid.

A three day expression profile of the CAR in CD14+ cells is demonstrated in FIG. 11. The expression level is highest at day 1, and although CAR expression is detectable at 72 hours, it is reduced gradually from peak expression. These expression profiles suggest a lack of tonic signaling by the CAR in these cells.

For the purpose of description in the rest of the Examples section, these cells may be referred to as effector myeloid cells.

Figure 12:
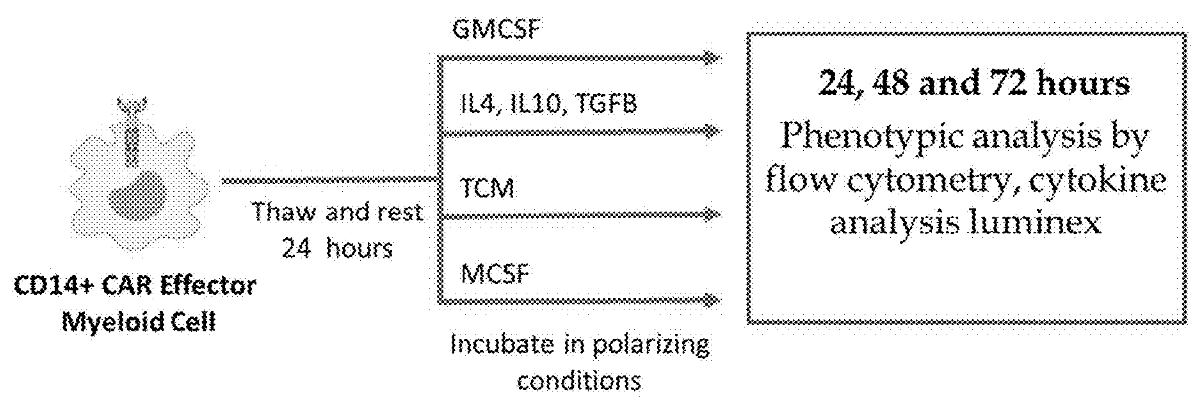
FIG. 12 is a schematic diagram of treating CD14+ cells with polarization stimulus to test polarization potential of cells.
Figure 13A:
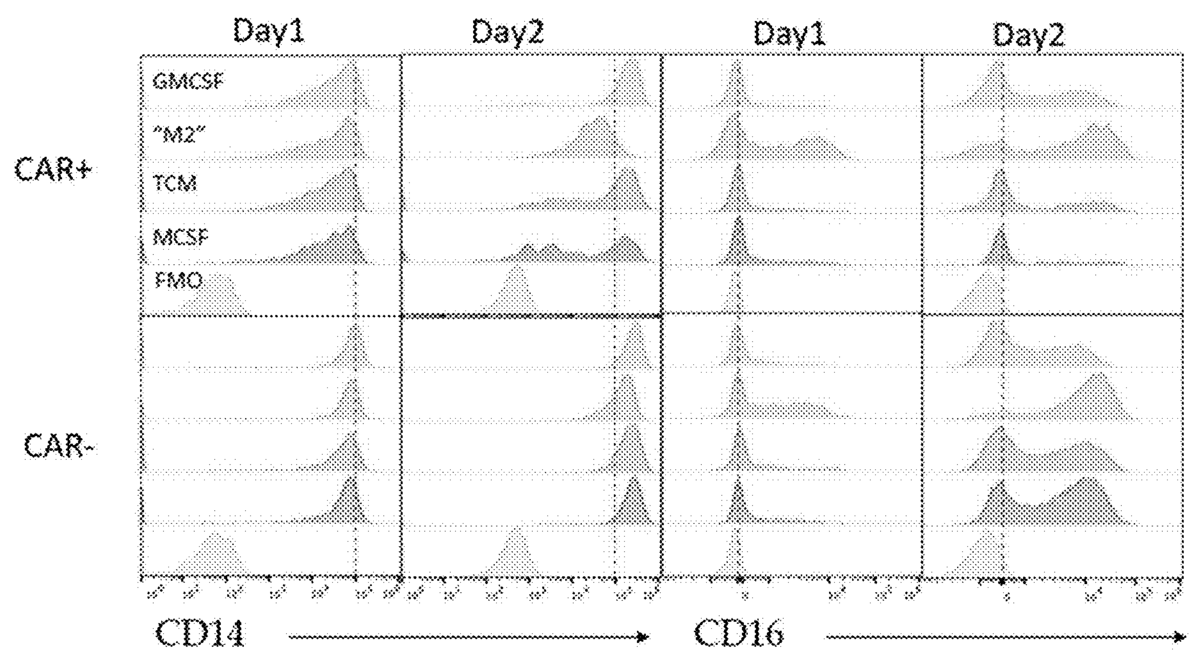
FIG. 13A shows flow cytometry data demonstrating changes in CD14 (left) and CD16 (right) expression levels of cells expressing or not expressing CARs, and in presence of a polarization stimulus.

Example 3. Characterizing Polarizing Potential of Isolated CD14+ Cells Expressing CAR This example demonstrates characterization of the potential of the isolated CD14+ cells expressing CAR (effector myeloid cells) to differentiate into different myeloid cell lines, as determined by expression of cell surface markers. Cells that were prepared and frozen as described in, e.g., Example 2, are thawed and cultured for 24 hours. These effector myeloid cells were then subject to polarizing stimuli, for example, as shown in FIG. 12, (i) GMCSF (ii) IL4, IL10, and TGFbeta (M2 stimuli), (iii) activated T cell conditioned media (TCM) and (iv) MCSF. Cells were analyzed at 24, 48 and 72 hours by flow cytometry, and cytokine analysis was performed by Luminex. CD14 expression was unaltered by CAR expression at day 1 after thawing, and increased with most polarizing stimuli at day 2, but was slightly lower in M2 cells (FIG. 13A, left). At day 1, CD16 levels in CAR expressing or non-expressing cells were unchanged, except for M2 cells, in which CD16 expression was unregulated. At day 2, however, CD16 expression levels were induced in most lines expressing or not expressing CARs, with GMCSF, IL4, IL10, and TGFbeta, and TCM, except in CAR-expressing cells induced with MCSF (FIG. 13A).

Figure 13B:
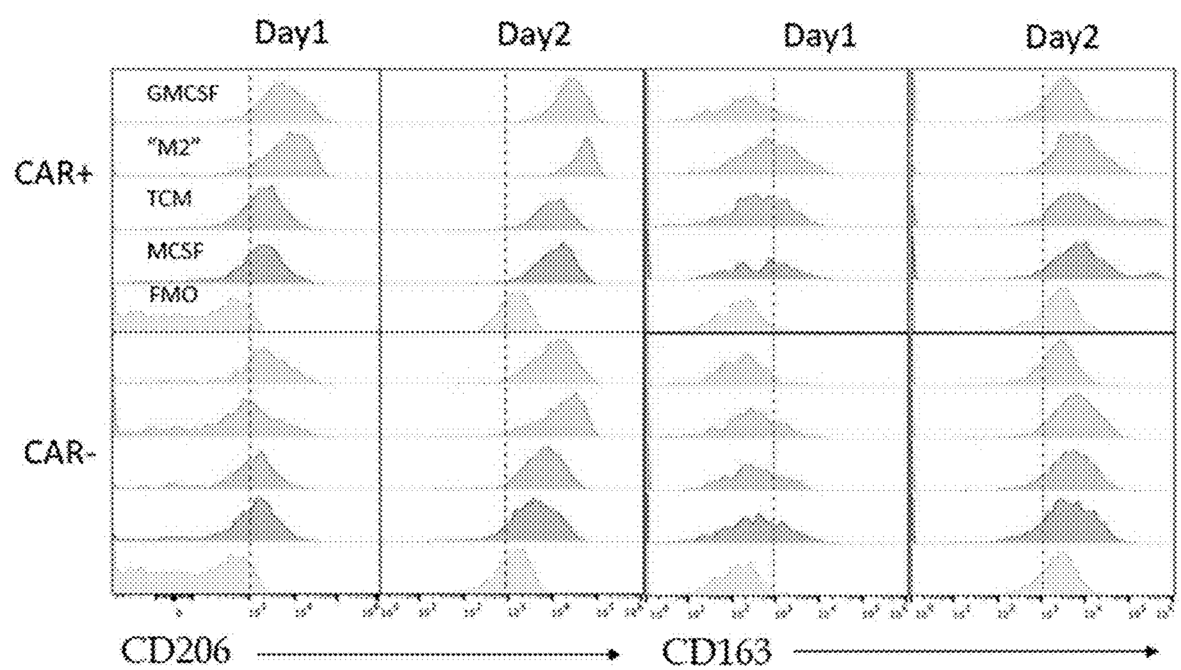
FIG. 13B shows flow cytometry data demonstrating changes in CD206 (left) and CD163 (right) expression levels of cells expressing or not expressing CARs, and in presence of a polarization stimulus.
Figure 13C:
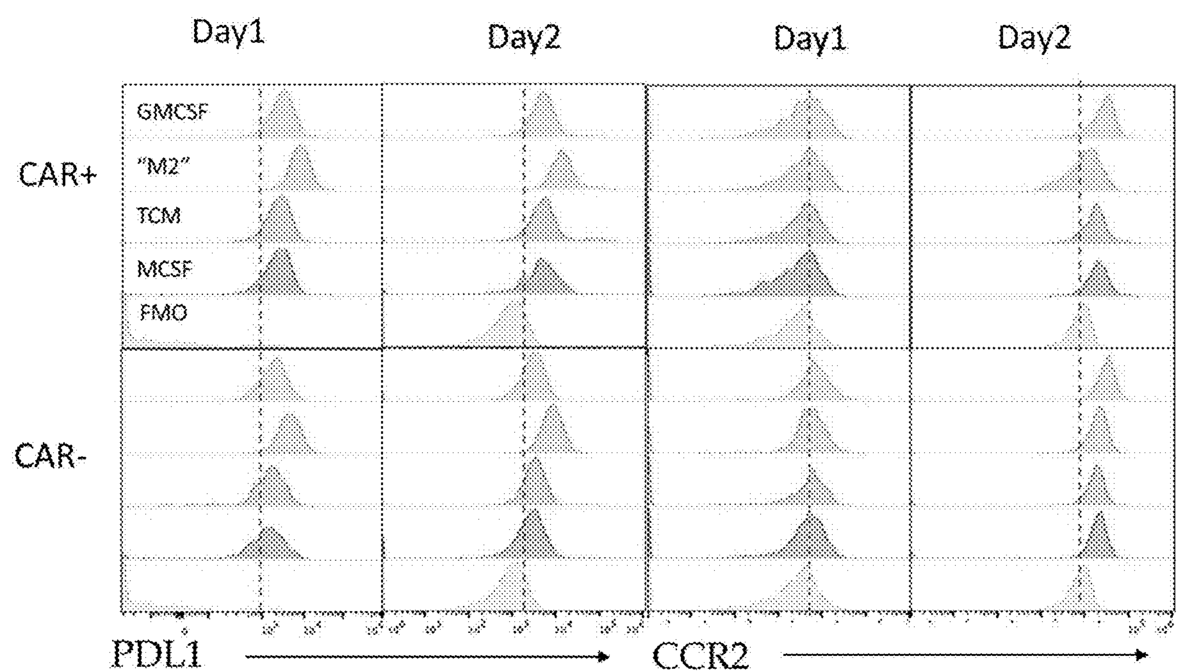
FIG. 13C shows flow cytometry data demonstrating changes in PDL1 (left) and CCR2 (right) expression levels of cells expressing or not expressing CARs, and in presence of a polarization stimulus.
Figure 13D:
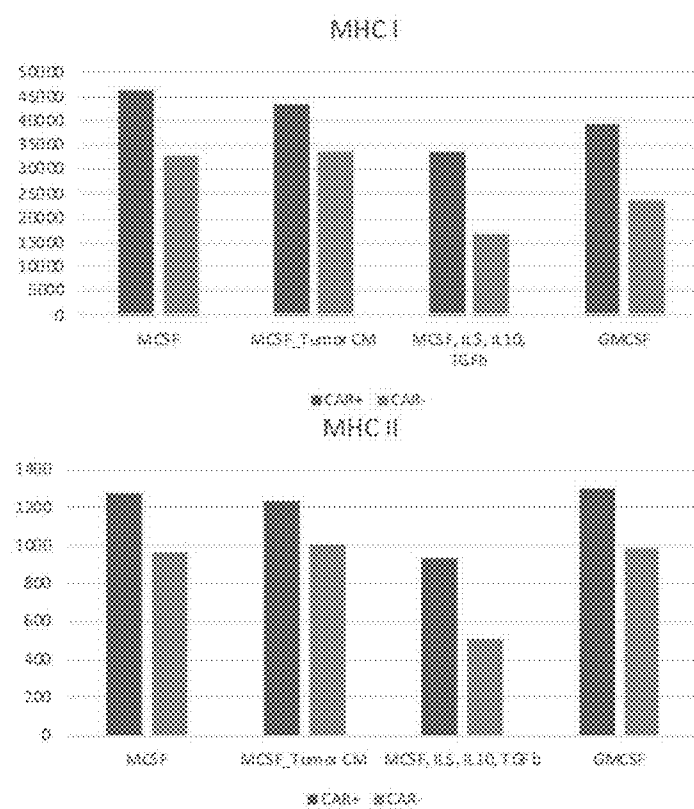
FIG. 13D shows flow cytometry data demonstrating changes in MHCI (top) and MHCII (bottom) expression levels of cells expressing or not expressing CARs, and in presence of a polarization stimulus.

As shown in FIG. 13B, CD206 is induced readily with any of the stimuli and the change was higher in the CAR expressing cells compared CAR non-expressing cells, while CD163 had little change over day 1, and the changes were uniform in CAR-expressing and non-expressing cells and in response to the various stimuli. Both CD206 and CD163 are macrophage activation markers. Increased CD206, or mannose receptor indicates higher phagocytic activity, and increased CD163 indicates higher inflammatory response. PDL1 expression was higher in M2 cells relative to other stimuli on day 1, and increased in all sets on day 2. CCR expression is high in CD14 cells with or without CAR expression, and generally increased further on day 2 (FIG. 13C). MHCI and MHCII expressions were analyzed in the variously stimulated CAR expressing and control cells. In each case CAR expressing cells have slightly higher MHC I and MHCII expression levels compared to the control (CAR-) cells.

Figure 14A:
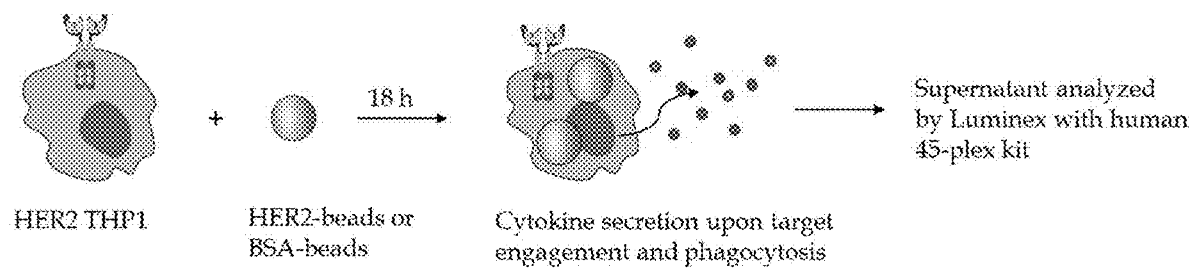
FIG. 14A depicts a schematic workflow diagram for an exemplary functional assay: THP-1 cells expressing a HER-2 specific CAR were stimulated with polarization stimulus, contacted with HER2 coated beads, and cytokine and chemokine release by the THP-1 cells were assayed using Luminex multiplex assay kit.
Figure 14B:
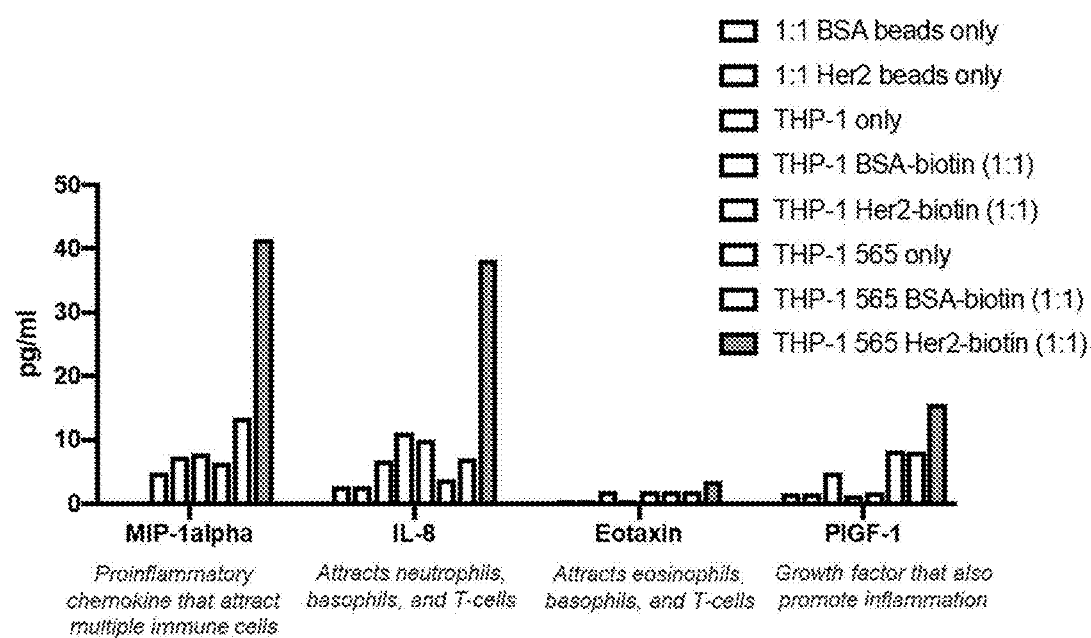
FIG. 14B shows data from Luminex assay of THP-1 cells in an exemplary experiment as described in FIG. 14A for the chemokines indicated.

Example 4. CAR Expressing Cells have High Target Specificity and are Responsive to Target Recognition HER2-CAR encoding mRNA was expressed in THP-1 cells, a human monocyte cell line, and incubated with HER2 coated beads. The HER2-THP-1 cells responded by secreting inflammatory cytokines that were detected by analyzing the supernatant using Luminex assay kits (FIG. 14A and FIG. 14B). As shown in FIG. 14B, the HER2-THP-1 cells express release MIP-1 alpha, IL-8, Eotaxin and PIGF-1 only in response to HER2 coated beads, and not BSA coated beads.

Figure 14C:
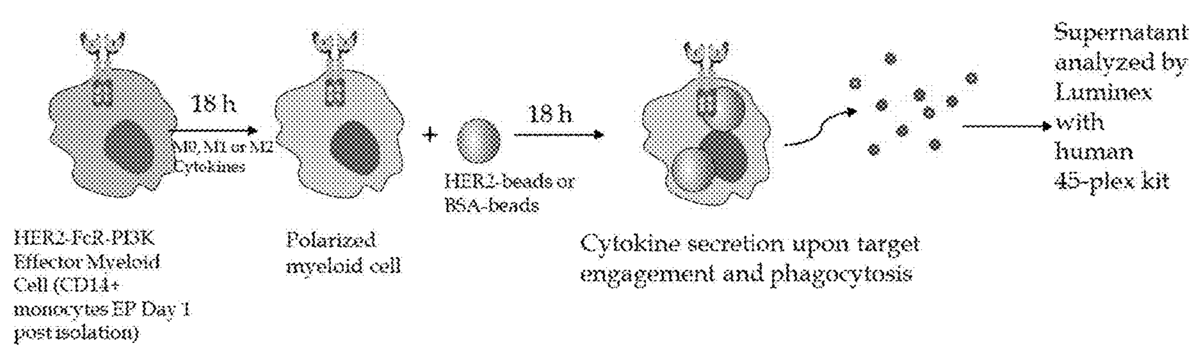
FIG. 14C depicts a schematic workflow diagram for an exemplary assay using myeloid cells expressing a HER-2 specific CAR having an intracellular domain comprising a PI3K recruitment domain, subjected to cytokines that direct M0, M1 or M2 polarization, and contacted with HER2 coated beads or control beads (coated with BSA) and cytokine and chemokine release by the THP-1 cells were assayed using Luminex multiplex assay kit.
Figure 14D:
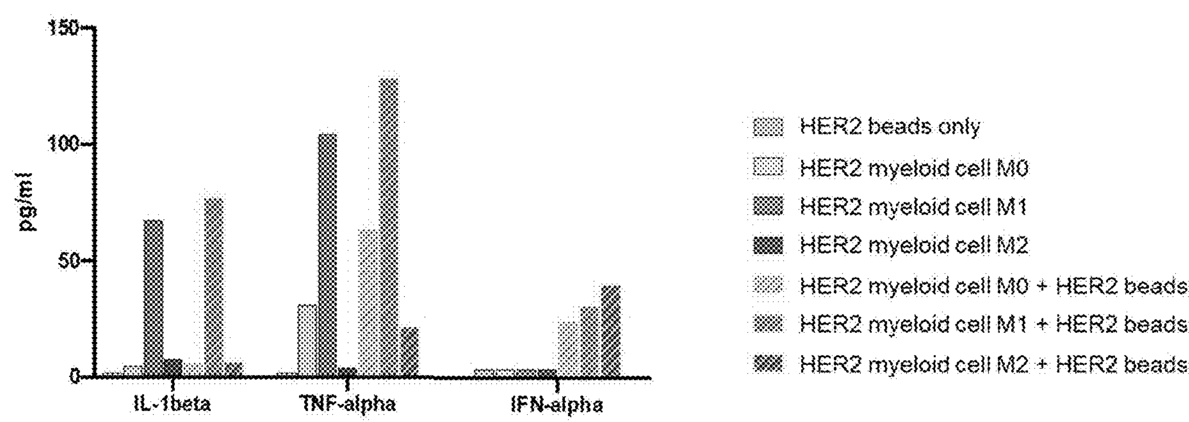
FIG. 14D shows data from Luminex assay of THP-1 cells in an exemplary experiment as described in FIG. 14C for the chemokines indicated.

Next, HER2-FCR-PI3K expressing effector myeloid cells were subjected to polarization stimuli after thawing, following the protocol described in Example 3. The CAR-mediated activation potential and specificity were tested in these cells by culturing the cells with a polarizing stimulus (Table 1), then contacting the cells with HER2 beads or control BSA beads. After 18 hours, cytokine secretion was analyzed by Luminex multiplex kits (FIG. 14C). Results are shown in FIG. 14D. HER2-targeting CD14+ CAR cells that were further polarized with M1 stimuli, when treated with HER2 beads expressed and secreted the highest levels of IL1beta and TNFalpha, compared to M0 or M2 polarized HER2-CAR expressing myeloid cells treated with HER2 beads. M2 polarized HER2-CAR expressing effector myeloid cells when contacted with HER2 beads, secreted high levels of IFN-gamma, which was higher than M1 or M0 cells that similarly express HER2-CAR and were activated by the HER2 beads. In absence of the target, tonic inflammatory cytokine expression was not observed.

Figure 15A:
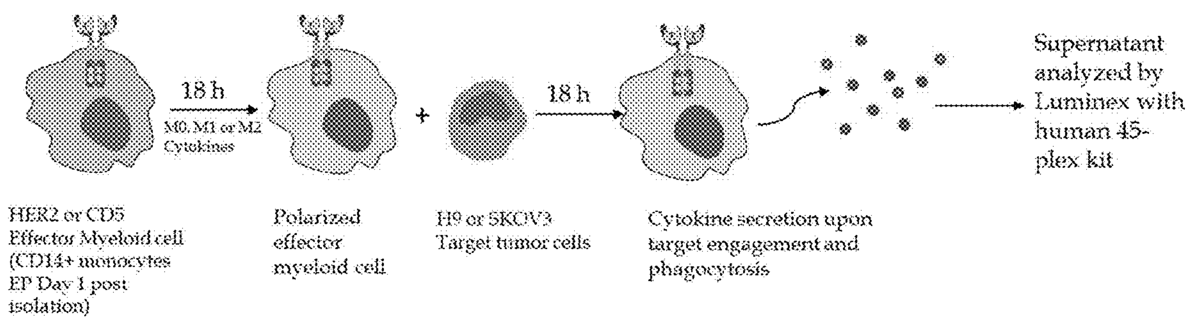
FIG. 15A depicts a schematic workflow diagram for an exemplary functional assay: Effector myeloid cells expressing a HER-2 specific CAR were stimulated with polarization stimulus, contacted with HER2 expressing tumor or non-HER-2 expressing tumor cells (e.g. H9 cells), and cytokine and chemokine release by the HER-2-CAR-myeloid cells were assayed using Luminex multiplex assay kit. As an alternative, C5-CAR expressing effector myeloid cells are subjected to the same treatment, and contacted with H9 T cell lymphoma or non-lymphoma cells (e.g. HER-1 expressing tumor cells) and analyzed as described above.
Figure 15B:
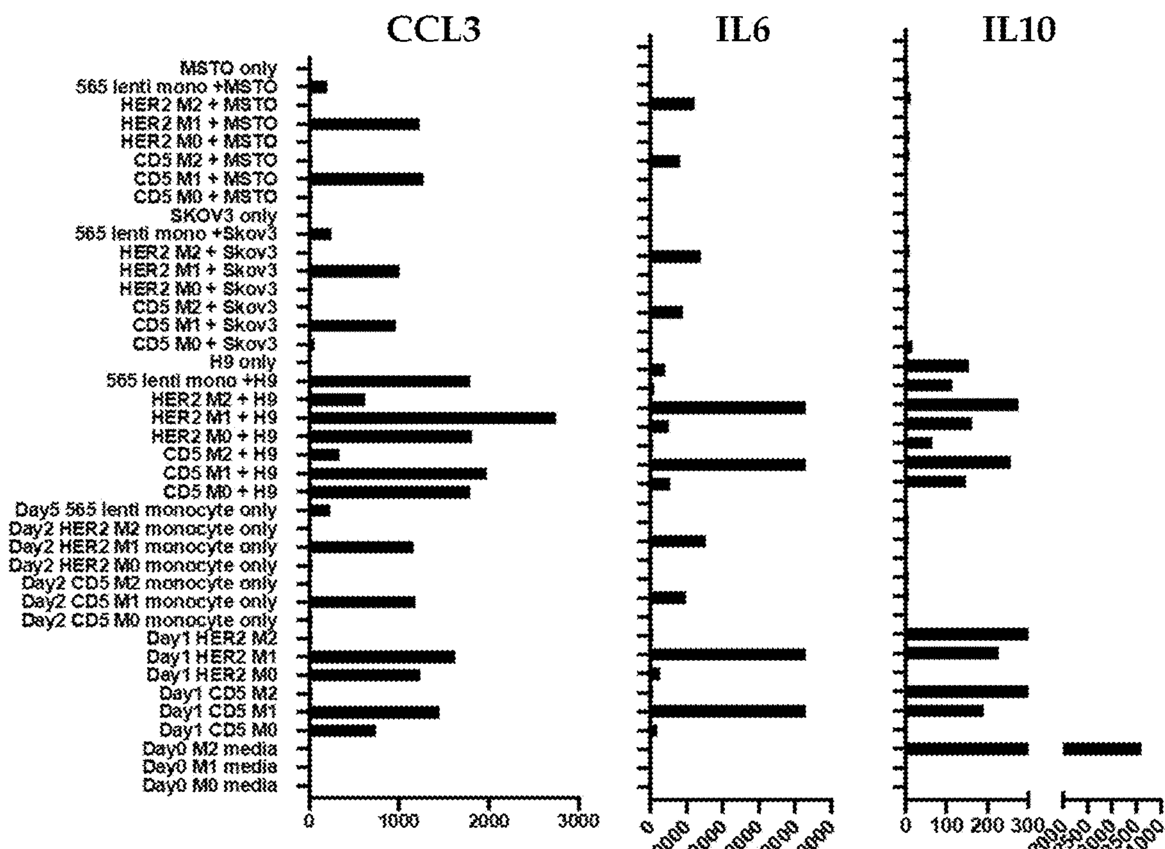
FIG. 15Bi shows data from Luminex assays from experiment described in FIG. 15A, for CCL3, IL6 and IL10 secretion.

To further understand the effect of these effector myeloid cells to tumor cells or non-tumor control cells HER2-specific and CD5-specific CAR expressing myeloid cells were subjected to M0, M1 or M2 polarization signal and incubated in the presence of tumor cells or non-tumor control cells in culture for 18 hours (FIG. 15A). Cytokine and chemokine profiles are shown in FIG. 15Bi and CD80 or CD206 expression profile are shown in FIG. 15Bii. M1 cells expressing HER2-CAR or C5-CAR, when incubated in the presence of SKOV3 or MSTO cell lines readily secreted CCL3, which indicates that the cells were activated. CCL3 chemokine helps in the migration of monocytes towards tumor cells. M2 differentiated cells released high levels of IL10 in absence of the tumor or control cells (FIG. 15Bi). All cells respond with elevated levels of chemokine CCL3, or IL6 or IL10 in the presence of H9 (lymphoma cells). Without wishing to be bound by a theory, the observation related to elevated CCL3 in some cases in response to H9 cells may be attributed to the interaction of a myeloid cell with a lymphoma cell. The expression levels of CD80 and CD206 did not alter in these cells despite the various treatments, indicating that the cells maintain the plasticity and do not express mature cell markers.

The results discussed in this example demonstrate that the CD14+ cells expressing a CAR are active and responsive to the specific tumor cells that express the target that the CAR is designed to recognize and bind (e.g. HER2).

Example 5. Phagocytic Potential of CD14+ Myeloid Cells

Figure 16A:
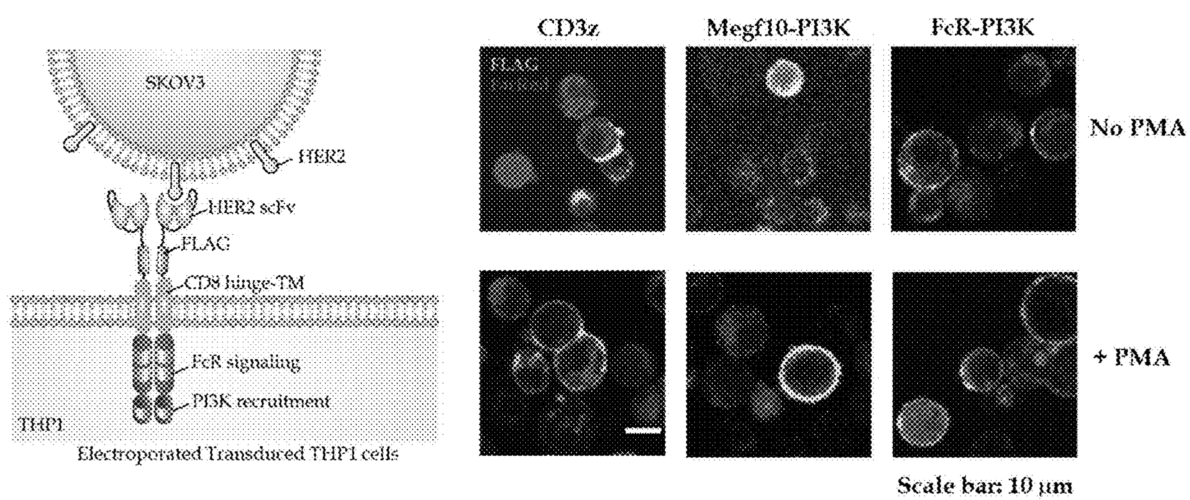
FIG. 16A shows data results from a phagocytosis assay. THP-1 cells were transduced with a HER-2-specific CAR that comprises an extracellular FLAG subunit, and contacted of HER-2 expressing SKOV3 (ovarian cancer cell line) cells which expresses a red-fluorescent protein. The design of the CAR is graphically represented in the image on the left side. THP-1 cells were stimulated with PMA or control. Imaging was performed after conjugating FLAD with a fluorescent antibody.

In this example, first THP-1 cells expressing a CAR having an extracellular HER2-binding domain and a FLAG sequence for labeling; and active intracellular signaling domains e.g., CD3z intracellular domain, or Megf10-PI3Kinase recruitment domains; or FcR signaling and PI3Kinase recruitment domains were used. The cells were incubated with labeled tumor cells, and phagocytosis was monitored which stimulated with PMA or control, by imaging. Phagocytosis of HER2 expressing tumor cells was observed in all groups (FIG. 16A).

Figure 16B:
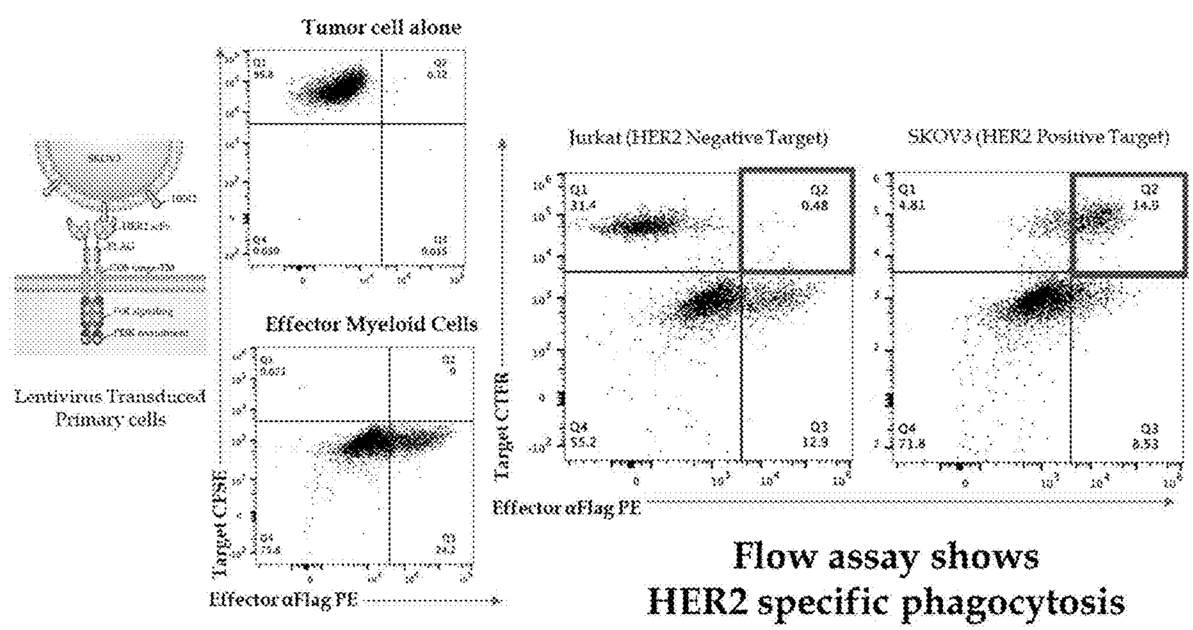
FIG. 16B shows results of a phagocytosis assay using lentivirus transduced primary effector myeloid cells expressing HER-2-specific CAR and flow cytometry was performed to quantify tumor engulfed myeloid cells.
Figure 16C:
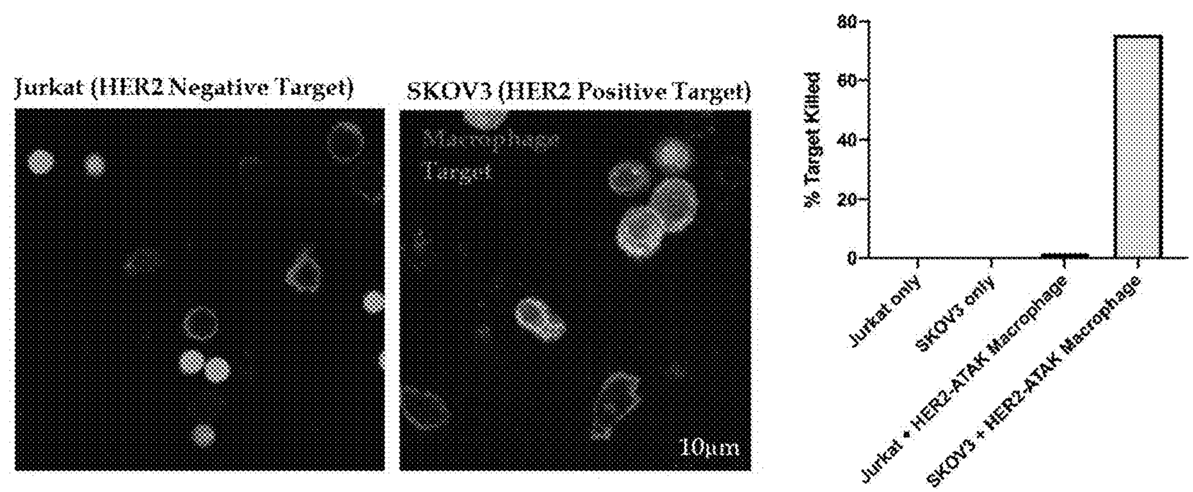
FIG. 16C shows confocal imaging data of Jurkat or SKOV3 engulfment in the experiment described in FIG. 16B. The graph on the right is a quantitative data generated from the imaging experiment.

Lentivirus transduced myeloid cells expressing a HER2 CAR as described above was incubated with HER2 positive tumor cells (target cells) or HER2 negative Jurkat cells and phagocytosed cells were quantified by flow cytometry (FIG. 16B). HER2 expressing myeloid cells specifically phagocytosed HER2 positive SKOV3 cells and not the Jurkat cells. FIG. 16C shows imaging results in agreement with the cytometry data.

Figure 17A:
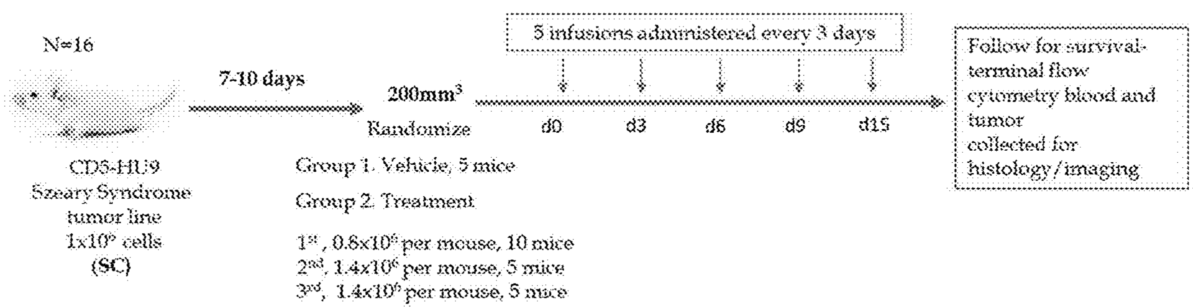
FIG. 17A depicts a schematic workflow diagram for an in vivo tumor model establishment in mice followed by five infusions of the effector myeloid cells expressing a tumor specific CAR, and survival studies, cytometric analysis and imaging studies were performed. In one representative experiment, the mice are grouped as shown.
Figure 17B:
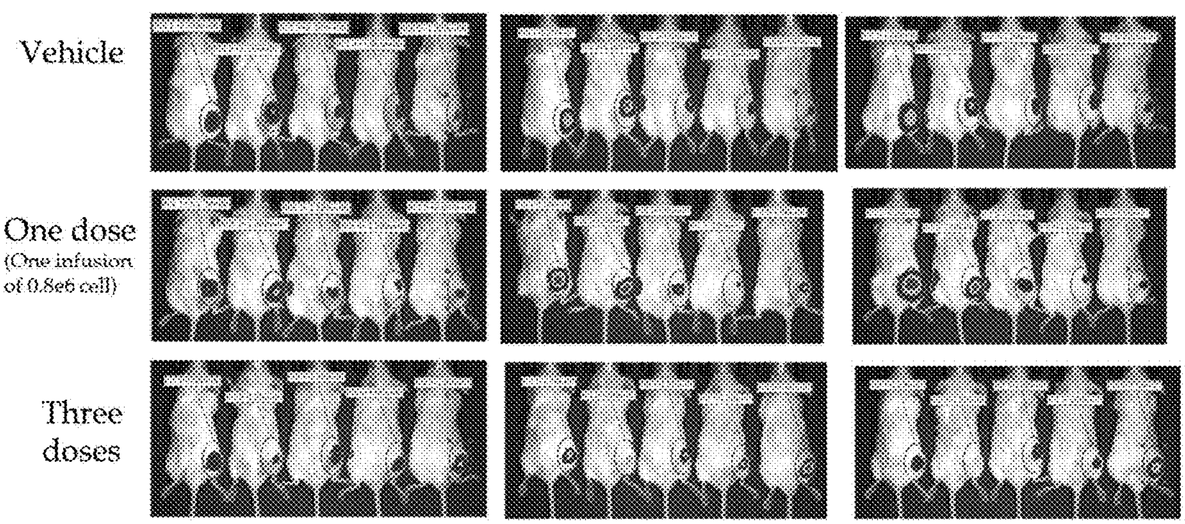
FIG. 17B shows bioimaging results showing tumor regression in mice in a representative experiment after one or three doses of myeloid cell infusion in a scheme as shown in FIG. 17A.
Figure 17C:
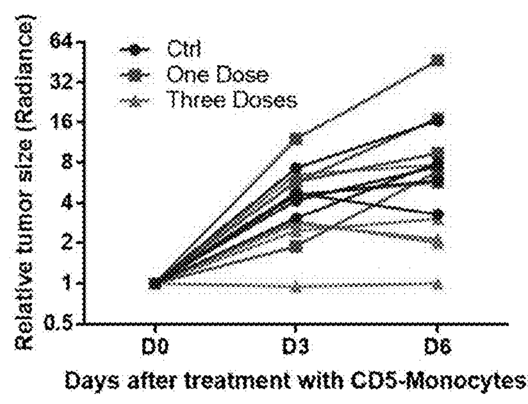
FIGS. 17C and 17D are quantitative assessments of tumor regression in an experimental set up as shown in FIGS. 17A and 17B.
Figure 17D:
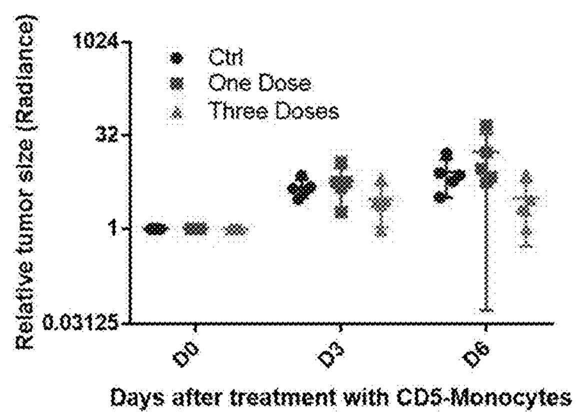

Example 6. Effect of Specific CAR-Expressing Effector Myeloid Cells on Mouse Tumor Model In this example, the in vivo effect of CAR-expressing effector myeloid cells was investigated. The objective was to set up a mouse tumor model, inject the mice with suitable myeloid cells, monitor outcome and determine effective dose levels. 1×10^6 cells of a CD5-HU9 Szeary Syndrome tumor cell line was subcutaneously introduced into healthy mice, which develop a tumor of about 200 mmA3 at the site in about 7-10 days. This tumor model was used for the experiment. Mice were divided into four groups, (a) Vehicle, (b) Treatment Groups: I (0.8×10^6 effector myeloid cells/mouse); (c) II (0.1.4×10^6 effector myeloid cells/mouse); and (d) III (0.1.4×10^6 effector myeloid cells/mouse). Five infusions were administered every 3 days as shown in FIG. 17A, and the mice were monitored for survival, and terminal assays including flow cytometry and bioimaging. FIG. 17B shows imaging data in one week, after 3 treatment doses. Surprisingly, tumor regression was observed in a few mice even after a single dose, and complete remission was observed in a couple of mice after three doses (FIG. 17B). Quantitative tumor regression data are provided in FIG. 17C and FIG. 17D.

Example 7. Myeloid Cell Isolation and Generation of CAR+ Myeloid Cells

In this example, myeloid cells for generation of CAR+ myeloid cells were isolated and enriched from peripheral blood sample, isolated from healthy donors or from Leukopak containers using either Protocol 1 or Protocol 2.

Protocol 1. Peripheral blood mononuclear cells (PBMC) were isolated from Leukopak collected from a healthy donor using Ficoll-Paque density centrifugation. Classical monocytes were isolated (enriched) by using an antibody cocktail (commercially available anti-human antibodies against CD3, CD7, CD16, CD19, CD56, CD123, and CD235a) to deplete multiple cell populations.

Protocol 2. Peripheral blood mononuclear cells (PBMC) were isolated from Leukopak collected from a healthy donor using Ficoll-Paque density centrifugation. CD14+ monocytes were isolated (enriched), by using an anti-human antibody to label and isolate CD14+ cells.

Cell viability and total counts were tested for each sample, both at pre-isolation and post-isolation. Myeloid cells for generation of CAR+ myeloid cells (CD14+/CD16−) were counted in each sample. Monocytes enriched using Protocol 1 and Protocol 2 were stained with anti-human antibodies against CD14, CD16 and analyzed by flow cytometry. Both protocols showed high enrichment of CD14+/CD16− cells. Shown in Table 2, Donor samples 1, 2, 3, 5 and 6 showed 4.74 fold, 7.06 fold, 7.6 fold, 24.96 fold and 9.61 fold enrichment of CD14+/CD16− cells respectively, using Protocol 1; with greater than 90% cell viability in each case. Donor samples 4, 8, 9, and the two leukapheresis samples showed 5.14 fold, 4.51 fold, 5.49 fold, 4.3 fold and 3.02 fold enrichment of CD14+/CD16− cells respectively, using Protocol 2; and also, with greater than 90% cell viability in each case.

TABLE 2 shows Pre-isolation and Post-isolation cell counts, viability and CD14+/CD16− population using Protocol 1 and Protocol 2.

| | Pre-Isolation | | | Post Isolation | | |
|---|---|---|---|---|---|---|
| Donor | Total Cells | CD14+/CD16− cells (% nucleated cells) | Enrichment method | Total Cells | Viability | CD14+/CD16− cells (% nucleated cells) |
| 1 | 3.60E+09 | 20% | Protocol 1 | 3.00E+08 | 94% | 94.80% |
| 2 | 3.60E+09 | 20% | Protocol 1 | 3.00E+08 | 94% | 94.80% |
| 3 | 1.40E+09 | 11% | Protocol 1 | 1.40E+09 | 95% | 83.7% |
| 4 | 5.50E+09 | 13% | Protocol 2 | 9.30E+08 | 95% | 66.9% |
| 5 | 2.10E+09 | 3% | Protocol 1 | 2.54e8 | 97% | 74.9% |
| 6 | 2.85E+09 | 8% | Protocol 1 | 3.85E+08 | 95% | 76.9% |
| Miltenyi Leukopak | n/a | n/a | Protocol 1 | 2.40E+08 | 98% | 82.8% |
| 7 | Huge aggregates, difficult to analyze | | | | | |
| 8 | 4.95E9 | 16.4% | Protocol 2 | 2.32e8 | 97.7% | 74% |
| 9 | 6.8E+09 | 14.2% | Protocol 2 | 8.58E+08 | — | 78% |
| Miltenyi Leukopak | 1.0E+10 | 17.3% | Protocol 2 | 1.20E+09 | — | 74.5% |
| Astarte 12.5 L Leukopak | 9.0E+10 | 25% | Protocol 2 | 2.0E+09 | — | 75.3% |

Figure 18A:
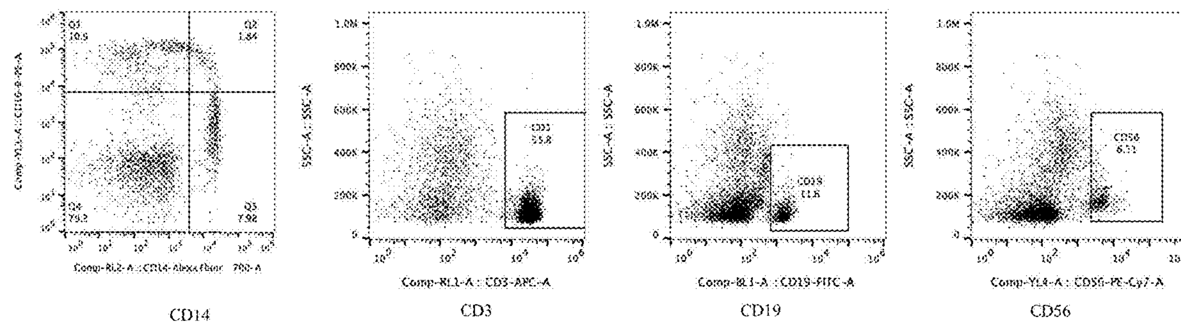
FIG. 18A (upper panel) shows PBMC cell population from human donor sample expressing CD14, CD3, CD19 and CD56 markers.
Figure 18A:
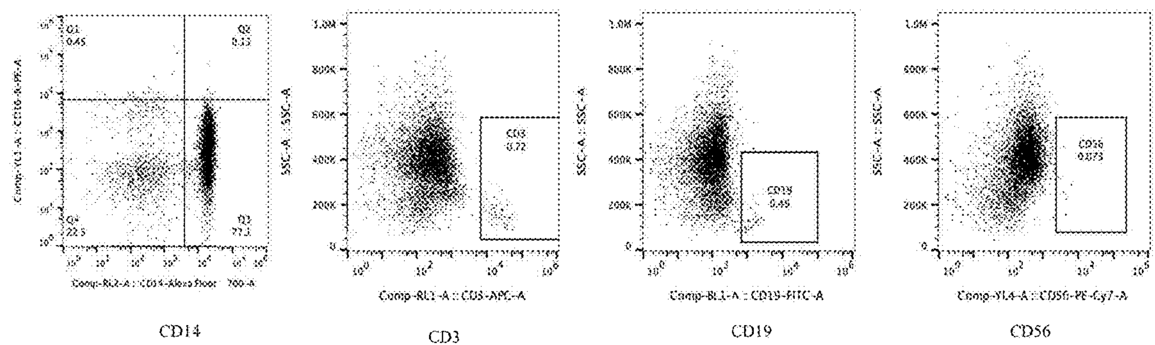
Figure 19A:
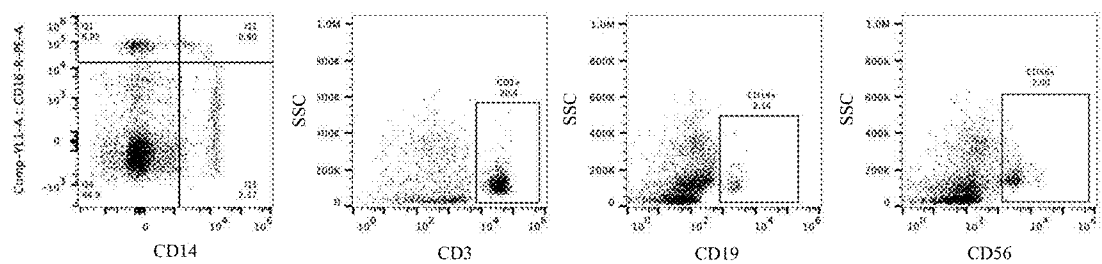
FIG. 19A (upper panel) shows PBMC cell population from a different human donor sample expressing CD14, CD3, CD19 and CD56 markers.
Figure 19A:
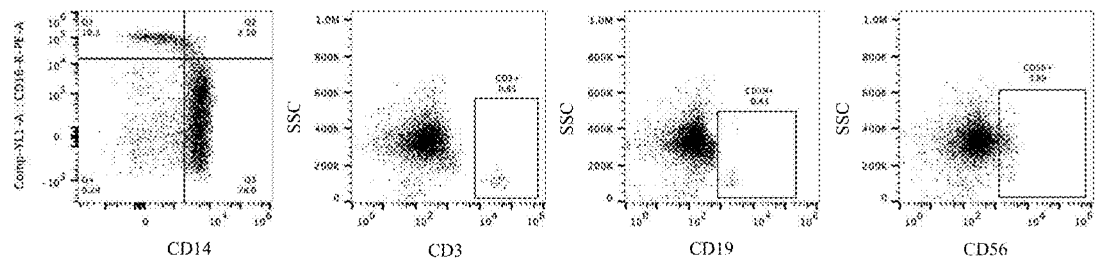

The immunophenotype of PBMC and Protocol 1 and Protocol 2-enriched monocytes were stained with anti-human antibodies against CD14, CD16, CD3, CD19 and CD56 and analyzed by flow cytometry. Shown in FIG. 18A is one representative assay using Donor sample 6 of Table 2, Less than 1% of CD3, CD19 and CD56 positive cells were present in the sample, showing efficient recovery and enrichment of CD14+/CD16− cells with negligible T cell, B cell and NK cell contaminations. Similarly, FIG. 19A shows a representative immunophenotyping of Donor sample 9 of PBMC using Protocol 2 of selected monocytes further stained with anti-human antibodies against CD14, CD16, CD3, CD19 and CD56 and analyzed by flow cytometry. Selected monocytes from this experiment are 78% CD14+ CD16−, with less than 5% of CD3, CD19 and CD56 positive cells.

Following recovery and enrichment of CD14+/CD16− monocytes as shown in the example, the cells were electroporated with mRNA encoding CD5 CAR recombinant construct.

Figure 18B:
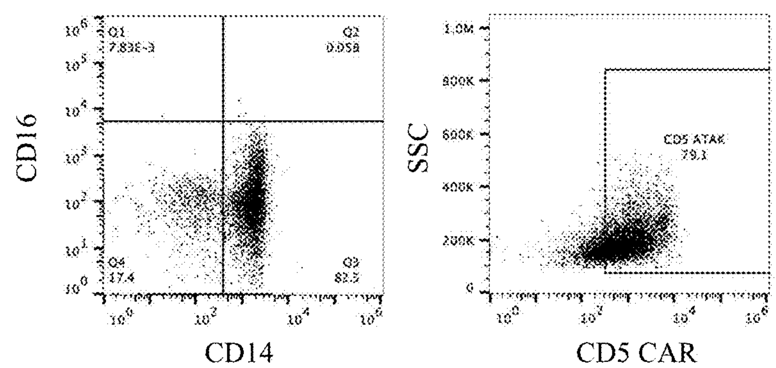
FIG. 18B shows monocytes isolated in FIG. 18A examined 18 h after incorporating nucleic acid encoding CD5-CAR. Flow cytometry data show CD14/CD16 expression (left) and CD5-CAR expression (right).
Figure 19B:
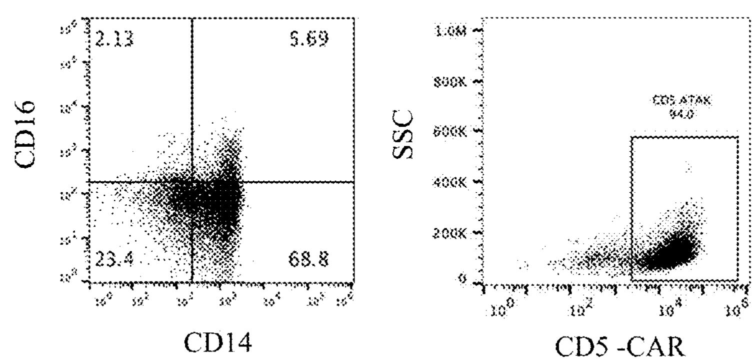
FIG. 19B shows monocytes isolated in FIG. 19A examined 18 h after incorporating nucleic acid encoding CD5-CAR. Flow cytometry data show CD14/CD16 expression (left) and CD5-CAR expression (right).

18 h after electroporation, monocytes were stained with anti-human antibodies against CD14 and CD16 as well as reagent to detect CD5-CAR transgene expression, and the cells were analyzed by flow cytometry. Result shows the cells are 82.5% CD14+ CD16− and 79.1% cells have CD5 CAR expression using Protocol 1 (FIG. 18B); and 68.8% CD14+ CD16− and 94% cells have CD5 CAR expression using Protocol 2 (FIG. 19B).

Representative CD5-CAR and HER2-CAR amino acid sequences are provided below.

CD5-FcR-PI3K (SEQ ID NO: 1)

MWLQSLLLLGTVACSISEIQLVQSGGGLVKPGGSVRISCAASGYTF

TNYGMNWVRQAPGKGLEWMGWINTHTGEPTYADSFKGRFTFSLDDS

KNTAYLQINSLRAEDTAVYFCTRRGYDWYFDVWGQGTTVTVSSGGG

GSGGGGSGGGGSDIQMTQSPSSLSASVGDRVTITCRASQDINSYLS

WFQQKPGKAPKTLIYRANRLESGVPSRFSGSGSGTDYTLTISSLQYE

DFGIYYCQQYDESPWTFGGGTKLEIKSGGGGSGALSNSIMYFSHFVP

VFLPAKPTTTPAPRPPTPAPTIASQPLSLRPEACRPAAGGAVHTRGL

-continued

DIYIWAPLAGTCGVLLLSLVITLYCRRLKIQVRKAAITSYEKSDGVY

TGLSTRNQETYETLKHEKPPQGSGSYEDMRGILYAAPQLRSIRGQPG

PNHEEDADSYENM

CD5-FcR-CD40

(SEQ ID NO: 2)

MWLQSLLLLGTVACSISEIQLVQSGGGLVKPGGSVRISCAASGYTFT

NYGMNWVRQAPGKGLEWMGWINTHTGEPTYADSFKGRFTFSLDDSKN

TAYLQINSLRAEDTAVYFCTRRGYDWYFDVWGQGTTVTVSSGGGGSG

GGGSGGGGSDIQMTQSPSSLSASVGDRVTITCRASQDINSYLSWFQQ

KPGKAPKTLIYRANRLESGVPSRFSGSGSGTDYTLTISSLQYEDFGI

YYCQQYDESPWTFGGGTKLEIKSGGGGSGALSNSIMYFSHFVPVFLP

AKPTTTPAPRPPTPAPTIASQPLSLRPEACRPAAGGAVHTRGLDIYI

WAPLAGTCGVLLLSLVITLYCRLKIQVRKAAITSYEKSDGVYTGLST

RNQETYETLKHEKPPQKKVAKKPTNKAPHPKQEPQEINFPDDLPGSN

TAAPVQETLHGCQPVTQEDGKESRISVQERQ

HER2-FcR-PI3K (SEQ ID NO: 3)

MWLQSLLLLGTVACSISDIQMTQSPSSLSASVGDRVTITCRASQDVN

TAVAWYQQKPGKAPKLLIYSASFLYSGVPSRFSGSRSGTDFTLTISS

LQPEDFATYYCQQHYTTPPTFGQGTKVEIKRTGSTSGSGKPGSGEGS

EVQLVESGGGLVQPGGSLRLSCAASGFNIKDTYIHWVRQAPGKGLEW

VARTYPTNGYTRYADSVKGRFTISADTSKNTAYLQMNSLRAEDTAVY

YCSRWGGDGFYAMDVWGQGTLVTVSSSGGGGSGALSNSIMYFSHFVP

VFLPAKPTTTPAPRPPTPAPTIASQPLSLRPEACRPAAGGAVHTRGL

DIYIWAPLAGTCGVLLLSLVITLYCRRLKIQVRKAAITSYEKSDGVY

TGLSTRNQETYETLKHEKPPQGSGSYEDMRGILYAAPQLRSIRGQPG

PNHEEDADSYENM

What is claimed is:

1. A pharmaceutical composition comprising (a) an ex vivo population of human cells comprising a recombinant polynucleic acid, wherein the recombinant polynucleic acid comprises a sequence encoding a chimeric fusion protein (CFP), wherein:
  (i) at least 50% of the cells in the ex vivo population of human cells are CD14+ and CD16−, and
  (ii) less than 10% of the cells in the ex vivo population of human cells are dendritic cells; and (b) a pharmaceutically acceptable excipient.

2. The pharmaceutical composition of claim 1, wherein at least 50% of the cells in the ex vivo population of human cells are CCR2+ and/or CCR5+.

3. The pharmaceutical composition of claim 1, wherein at least 50% of the cells in the ex vivo population of human cells are CD63+.

4. The pharmaceutical composition of claim 1, wherein at least 50% of the cells in the ex vivo population of human cells are CD56−, CD3−, and/or CD19−.

5. The pharmaceutical composition of claim 1, wherein less than 40% of the cells in the ex vivo population of human cells are macrophage cells.

6. The pharmaceutical composition of claim 1, wherein:

(a) at least 50% of the cells in the ex vivo population of human cells are CCR2+ and/or CCR5+;

(b) at least 50% of the cells in the ex vivo population of human cells are CD63+;

(c) at least 50% of the cells in the ex vivo population of human cells are CD56−, CD3−, and/or CD19−; and (d) less than 40% of the cells in the ex vivo population of human cells are macrophage cells.

7. The pharmaceutical composition of claim 1, wherein the recombinant polynucleic acid comprises RNA.

8. The pharmaceutical composition of claim 1, wherein the recombinant polynucleic acid comprises a sequence encoding a CFP, and the ex vivo population of human cells lacks tonic signaling through the CFP.

9. The pharmaceutical composition of claim 1, wherein the CFP comprises:

(a) an extracellular domain comprising an antigen binding domain, and (b) a transmembrane domain operatively linked to the extracellular domain.

10. The pharmaceutical composition of claim 9, wherein the antigen binding domain is a CD5 binding domain or a HER2 binding domain.

11. The pharmaceutical composition of claim 9, wherein the CFP further comprises an intracellular domain derived from a phagocytic receptor or a scavenger receptor.

12. The pharmaceutical composition of claim 9, wherein the CFP comprises:

(a) an extracellular domain comprising:
  (i) a scFv that specifically binds CD5 or HER2, and
  (ii) a hinge domain derived from CD8, or CD28 or an extracellular domain of CD68 or a portion thereof;

(b) a CD8 transmembrane domain, a CD28 transmembrane domain or a CD68 transmembrane domain; and (c) an intracellular domain comprising at least two intracellular signaling domains, wherein the at least two intracellular signaling domains comprise
  (i) a first intracellular signaling domain derived from FcγR or FcεR, and
  (ii) a second intracellular signaling domain that:
    (A) comprises a PI3-kinase (PI3K) recruitment domain, or
    (B) is derived from CD40.

13. A method of treating a disease or condition in a human subject in need thereof comprising: administering the pharmaceutical composition of claim 1 to the human subject.

14. The method of claim 13, wherein cells of the ex vivo population of human cells:

(a) differentiate into effector cells in the subject after administration;

(b) infiltrate into a diseased site of the subject after administration or migrate to a diseased site of the subject after administration; or (c) have a life-span of at least 5 days in the subject after administration.

15. The method of claim 13, wherein the ex vivo population of human cells is from the human subject.

16. The method of claim 13, wherein the pharmaceutical composition is administered to the human subject within 72 hours after the recombinant polynucleic acid has been introduced into the ex vivo population of human cells.

17. The method of claim 13, wherein the ex vivo population of human cells has been cultured for less than 48 hours ex vivo prior to administration.

18. A method of negatively selecting cells for preparing the pharmaceutical composition of claim 1, the method comprising: (a) contacting a biological sample from a human subject with an anti-CD16 antibody and one or more antibodies selected from anti-CD56 antibody, anti-CD3 antibody and anti-CD19 antibody, (b) collecting cells in the biological sample that are not bound by the anti-CD16 antibody and not bound by the one or more antibodies, and (c) introducing a recombinant polynucleic acid comprising a sequence encoding a CFP into cells collected from (b), thereby forming a population of cells, wherein: (i) at least 50% of the cells in the population of cells are CD14+ and CD16, and (ii) less than 10% of the cells in the population of cells are dendritic cells.

19. The method of claim 18, wherein the method comprises flow cytometry.

20. The pharmaceutical composition of claim 1, wherein the ex vivo population of human cells comprises at least $1\times10^7$ cells.

21. The pharmaceutical composition of claim 1, wherein the antigen binding domain is a cancer antigen binding domain.

* * * * *

UNITED STATES PATENT AND TRADEMARK OFFICE

CERTIFICATE OF CORRECTION

PATENT NO. : 10,980,836 B1
APPLICATION NO. : 16/826708
DATED : April 20, 2021
INVENTOR(S) : Daniel Getts and Yuxiao Wang It is certified that error appears in the above-identified patent and that said Letters Patent is hereby corrected as shown below:

In the Claims

Claim 18, Column 69, Lines 21 and 22:
"cells are CD14+ and CD16" should read -- cells are CD14+ and CD16- --

Signed and Sealed this
Ninth Day of April, 2024

Katherine Kelly Vidal

Katherine Kelly Vidal
*Director of the United States Patent and Trademark Office*

SEQUENCE LISTING

```
<160> NUMBER OF SEQ ID NOS: 3

<210> SEQ ID NO 1
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45
```

```
Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Leu Lys Ile Gln Val Arg Lys Ala Ala Ile Thr Ser Tyr Glu Lys Ser
        355                 360                 365

Asp Gly Val Tyr Thr Gly Leu Ser Thr Arg Asn Gln Glu Thr Tyr Glu
    370                 375                 380

Thr Leu Lys His Glu Lys Pro Pro Gln Gly Ser Gly Ser Tyr Glu Asp
385                 390                 395                 400

Met Arg Gly Ile Leu Tyr Ala Ala Pro Gln Leu Arg Ser Ile Arg Gly
                405                 410                 415

Gln Pro Gly Pro Asn His Glu Glu Asp Ala Asp Ser Tyr Glu Asn Met
            420                 425                 430
```

<210> SEQ ID NO 2
<211> LENGTH: 454
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 2

```
Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Lys Lys Val Ala Lys Lys Pro Thr
385                 390                 395                 400
```

```
Asn Lys Ala Pro His Pro Lys Gln Glu Pro Gln Glu Ile Asn Phe Pro
                405                 410                 415

Asp Asp Leu Pro Gly Ser Asn Thr Ala Ala Pro Val Gln Glu Thr Leu
            420                 425                 430

His Gly Cys Gln Pro Val Thr Gln Glu Asp Gly Lys Glu Ser Arg Ile
        435                 440                 445

Ser Val Gln Glu Arg Gln
    450


<210> SEQ ID NO 3
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Trp Leu Gln Ser Leu Leu Leu Leu Gly Thr Val Ala Cys Ser Ile
1               5                   10                  15

Ser Asp Ile Gln Met Thr Gln Ser Pro Ser Ser Leu Ser Ala Ser Val
            20                  25                  30

Gly Asp Arg Val Thr Ile Thr Cys Arg Ala Ser Gln Asp Val Asn Thr
        35                  40                  45

Ala Val Ala Trp Tyr Gln Gln Lys Pro Gly Lys Ala Pro Lys Leu Leu
    50                  55                  60

Ile Tyr Ser Ala Ser Phe Leu Tyr Ser Gly Val Pro Ser Arg Phe Ser
65                  70                  75                  80

Gly Ser Arg Ser Gly Thr Asp Phe Thr Leu Thr Ile Ser Ser Leu Gln
                85                  90                  95

Pro Glu Asp Phe Ala Thr Tyr Tyr Cys Gln Gln His Tyr Thr Thr Pro
            100                 105                 110

Pro Thr Phe Gly Gln Gly Thr Lys Val Glu Ile Lys Arg Thr Gly Ser
        115                 120                 125

Thr Ser Gly Ser Gly Lys Pro Gly Ser Gly Glu Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Asn Ile Lys Asp Thr Tyr Ile His
                165                 170                 175

Trp Val Arg Gln Ala Pro Gly Lys Gly Leu Glu Trp Val Ala Arg Ile
            180                 185                 190

Tyr Pro Thr Asn Gly Tyr Thr Arg Tyr Ala Asp Ser Val Lys Gly Arg
        195                 200                 205

Phe Thr Ile Ser Ala Asp Thr Ser Lys Asn Thr Ala Tyr Leu Gln Met
    210                 215                 220

Asn Ser Leu Arg Ala Glu Asp Thr Ala Val Tyr Tyr Cys Ser Arg Trp
225                 230                 235                 240

Gly Gly Asp Gly Phe Tyr Ala Met Asp Val Trp Gly Gln Gly Thr Leu
                245                 250                 255

Val Thr Val Ser Ser Ser Gly Gly Gly Gly Ser Gly Ala Leu Ser Asn
            260                 265                 270

Ser Ile Met Tyr Phe Ser His Phe Val Pro Val Phe Leu Pro Ala Lys
        275                 280                 285

Pro Thr Thr Thr Pro Ala Pro Arg Pro Pro Thr Pro Ala Pro Thr Ile
```

-continued

```
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Arg Arg Leu Lys Ile Gln Val Arg Lys Ala Ala Ile Thr Ser
        355                 360                 365

Tyr Glu Lys Ser Asp Gly Val Tyr Thr Gly Leu Ser Thr Arg Asn Gln
    370                 375                 380

Glu Thr Tyr Glu Thr Leu Lys His Glu Lys Pro Pro Gln Gly Ser Gly
385                 390                 395                 400

Ser Tyr Glu Asp Met Arg Gly Ile Leu Tyr Ala Ala Pro Gln Leu Arg
                405                 410                 415

Ser Ile Arg Gly Gln Pro Gly Pro Asn His Glu Glu Asp Ala Asp Ser
            420                 425                 430

Tyr Glu Asn Met
        435
```